(12) United States Patent
Welkie et al.

(10) Patent No.: US 7,043,406 B1
(45) Date of Patent: May 9, 2006

(54) APPARATUS AND METHODS FOR REDUCTION OF COHERENT NOISE IN A DIGITAL SIGNAL AVERAGER

(75) Inventors: David G. Welkie, Branford, CT (US); Craig M. Whitehouse, Branford, CT (US)

(73) Assignee: Analytica of Branford, Inc., Branford, CT (US)

( * ) Notice: Subject to any disclaimer, the term of this patent is extended or adjusted under 35 U.S.C. 154(b) by 0 days.

(21) Appl. No.: 10/421,590

(22) Filed: Apr. 23, 2003

Related U.S. Application Data

(60) Provisional application No. 60/374,943, filed on Apr. 23, 2002.

(51) Int. Cl.
*H04B 15/00* (2006.01)
(52) U.S. Cl. ............. 702/194; 250/308.08; 250/308.09
(58) Field of Classification Search ................ 702/194; 250/390.08, 390.07
See application file for complete search history.

(56) References Cited

U.S. PATENT DOCUMENTS 6,094,627 A * 7/2000 Peck et al. .................. 702/199

* cited by examiner

*Primary Examiner*—John Barlow
*Assistant Examiner*—Anthony T. Dougherty
(74) *Attorney, Agent, or Firm*—Levisohn, Berger & Langsam, LLP

(57) ABSTRACT

Apparatus and methods are provided for reducing coherent noise in measurements of repetitive analog signal waveforms by digital signal averagers. Coherent noise is repetitive and synchronous with the signal waveform and is therefore undiminished by conventional signal averaging techniques. A major source of coherent noise is the repetitive voltage transitions that occur within the digital signal averager itself. The apparatus and methods of the present invention introduce a known and variable phase offset during the signal averaging process between the signal waveform being measured and the internally generated coherent noise, thereby allowing such coherent noise to be averaged, and therefore reduced, during the signal averaging process. Consequently, the apparatus and methods of the present invention allow greater signal-to-noise ratio and signal dynamic range than with the prior art.

49 Claims, 33 Drawing Sheets

APPARATUS AND METHODS FOR REDUCTION OF COHERENT NOISE IN A DIGITAL SIGNAL AVERAGER

This application claims the benefit of 60/374,943.

FIELD OF THE INVENTION

The present invention relates to the measurement of repetitive electronic waveforms. More specifically, the present invention provides methods and apparatus for reducing internally generated noise for instruments in which analog-to-digital converters digitize such waveforms and wherein repeated measurements are averaged to improve the signal-to-noise ratio and the dynamic range characteristics of the measurement.

BACKGROUND OF THE INVENTION

Various kinds of signal recording technologies are employed in many different kinds of instruments for the measurement of a time-varying voltage, such as x–y recorders, oscilloscopes, and analog-to-digital converters (ADC's) combined with memory arrays. In the latter configuration, the voltage waveform is recorded by sampling the voltage at well-defined, discrete time intervals with the ADC. The resulting digital values are transferred sequentially to storage elements of a memory array, creating a digital record of the voltage waveform, which may be subsequently processed and stored using a computer. If the voltage waveform is repetitive, then the same voltage waveform may be recorded similarly a number of times. By averaging the digitized waveforms, that is, by summing data values in all records that correspond to the same relative time-phase of the waveform, and dividing the result by the number of records, the signal-to-noise ratio of the measurement may be improved. Specifically, it is well known that, if the noise can be characterized as so-called random or white, Gaussian noise, then the root-mean-square (RMS) magnitude of the noise in the spectrum decreases in proportion to the square root of the number of waveform measurements that are averaged, while the signal remains the same, so that the signal-to-noise ratio improves accordingly.

A measurement instrument specially tailored to perform such signal averaging of repetitive voltage waveforms is conventionally referred to as a digital signal averager (DSA). A generic DSA typically includes an ADC; a precision clock for timing the intervals between consecutive analog-to-digital conversions, as well as timing the repetitive sequence of data transfer, processing and storage; an array of memory elements for storing and providing access for subsequent processing of the digitized data; and hardware for performing arithmetic operations on the data in the memory array elements; as well as hardware for performing other auxiliary functions such as data processing, data transfer, etc. Often, the signal averaging process is performed in real time. That is, as each voltage waveform is digitized, each digital data value output by the ADC is added promptly to the value in the memory array element that represents the summation of all previously recorded values of the voltage waveform at this same phase position in the waveform. After a desired number of waveforms have been summed, the resulting integrated waveform may be scaled to produce a true average waveform by dividing the summed waveform values by the number of waveform measurements records, although this extra operation, if performed at all, is often performed only after the summed waveform data is transferred out of the DSA and into computer memory for so-called post-processing. In principle, it is possible to envision the signal averaging process being performed after all repeated measurements of the voltage waveform have been completed, whereby each waveform measurement had been recorded in a separate memory array or array segment. However, a large number of records is usually desired for signal averaging in practice, and the corresponding memory requirements usually, but not always, become impractical with such an approach. Hence, signal averaging is most commonly performed in real time, or approximately real time, as consecutive waveforms are recorded.

In order to signal average repetitive waveforms, it is necessary that the same phase relation is maintained among all recorded waveforms during the summation process. This simply means that the value in any particular memory location must be the summation of all repeated measurements of the signal at the same relative phase of the waveform. There are different schemes that may be employed to accomplish this, depending on the experimental situation. In one situation, it may be possible to detect a particular feature of the waveform of interest, and to trigger the start of the waveform recording process on such a feature; as is commonly done in digital oscilloscopes. In such situations, there will inevitably be an uncertainty in the relative phases between different recordings of the waveform of up to plus or minus one ADC digitization interval because of the lack of synchronization between the signal waveform and the ADC clock internal to the DSA.

Another common situation is that in which the voltage waveform to be measured may be produced on demand from the experiment in response to a trigger signal, and where the resulting voltage waveform is reproduced with the same phase relation to the trigger each time. In this case, it is advantageous, with respect to achieving the best timing accuracy and precision, to arrange for the trigger signal to be synchronous with the internal clock of the DSA. Then, the start of the waveform recording process by the DSA, commonly referred to as a 'scan', may be initiated at a time or phase relative to this so-called 'Start' signal that is the same for all recorded waveforms. Consequently, it is straightforward to ensure that the contents of any particular memory array location will always correspond to the signal at the same point on the waveform for each scan, resulting in the correct summation of consecutive scans. The complete signal waveform average of a number of scans is commonly referred to as a 'record'. Digital signal averagers that have been designed for and employed in these latter experimental situations are disclosed, for example, in U.S. Pat. Nos. 4,490,806, 5,428,357, and 6,094,627. Examples of current state-of-the-art commercial implementations of such DSA's include the FastFlight DSA from EG&G Ortec, the Eclipse DSA from EG&G Signal Recovery, and the AP100/200 from Acqiris SA.

An illustration of this latter experimental situation is shown schematically in FIG. 1, which depicts a conventional DSA 30 being used to record the time-dependent signal 5 constituting a portion of interest of an ion mass spectrum produced by a time-of-flight mass analyzer 25. In the particular configuration of a time-of-flight mass analyzer 25 illustrated in FIG. 1, ions of a sample of interest 24 are introduced, by any of a variety of different methods that are well-known to those skilled in the art (such as laser desorption/ionization from a surface, orthogonal injection from an external ion source, electron-impact ionization of resident gas molecules, etc.) into a region of the mass analyzer known as the pulsing region 23. Upon application of a voltage pulse 20 from a voltage pulse generator 21 to an electrode 22 bounding the pulsing region 23, ions are accelerated into the time-of-flight measurement chamber 26, and arrive at a detector 27 with a time dependence that is proportional to the square-root of their mass-to-charge ratio. As ions arrive at the detector 27, a signal 5, related to the number of ions present for each mass-to-charge ratio, is generated, which is introduced, usually after amplification, to the input 6 of the DSA 30 for measurement and recording. Such time-dependent signal waveforms may therefore be interpreted in terms of the types of chemical species present in the original sample, as indicated by the various mass-to-charge peaks in the spectrum, while the amplitude of such peaks provide some measure of the relative amounts of the different species. A number of such scans are typically signal averaged to improve the signal-to-noise ratio of the measurement. The voltage pulse 20 that begins each time-of-flight spectrum measurement is triggered by a signal at the DSA trigger output 4 in synchronization with the internal clock of the DSA. Therefore, each scan may easily be synchronized with all previous scans, which is necessary to achieve a valid signal average record of all the scans.

An example of such a time-of-flight spectrum is illustrated in FIG. 2. This data was obtained from a commercially available time-of-flight mass spectrometer, manufactured and sold by Amersham Biosciences as the mass spectrometer of the Ettan LC/MS system. This system utilizes a customized version of the FastFlight DSA commercially available from EG&G Ortec. The data shown in FIG. 2 was acquired from a sample of hexatyrosine (20 pmole/uL in 50/50 methanol/water, 0.1% acetic acid), which was introduced into the electrospray ion source of the Ettan TOF mass spectrometer by constant infusion at a flow rate of 10 uL/min.

The spectrum of FIG. 2 is an average of 10 scans. The DSA signal offset setting was adjusted so that the entire signal waveform as well as the noise characteristics could be observed. In fact, the signal offset setting was adjusted so that the average zero-level baseline of the spectrum more or less coincided with 1 LSB of the ADC, as indicated by the dashed line in FIG. 2. Therefore, both positive and negative excursions from the average baseline, due to both noise and negative fluctuations in the signal (provided the amplitude of negative excursions does not exceed 1 LSB per scan), could be observed and measured. In the spectrum of FIG. 2, some of the ion signal peaks are apparent, for example, at flight times corresponding to memory array bins 9,992; 18,143; 25,553; and 33,935. Noise is also clearly evident throughout the spectrum of FIG. 2. Digital signal averaging is effective at improving the signal-to-noise ratio in such measurements of repetitive waveforms, but only if the noise is not coherent with the measured waveform, as with randomly distributed noise, or white Gaussian noise. Coherent noise, that is, noise that is time-correlated with the measured signal waveform, behaves just as the waveform signal does with respect to a signal averaging process. Consequently, owing to its coherency with the waveform signal, coherent noise is not reduced at all by conventional signal averaging. Hence, coherent noise is often the most important factor that limits the signal-to-noise ratio and dynamic range that can be achieved by a digital signal averager.

Noise that is coherent with the measured repetitive waveform may originate from sources coherent with the signal source, such as cable reflections, ringing due to impedance mismatches in the signal path, partial coupling of the initial trigger stimulus to the response signal, etc. Such sources of coherent noise can be made relatively insignificant with careful engineering design. However, coherent noise may also originate from within the digital signal averager itself, often due, for example, to coupling between the signal input and voltage transitions that occur internal to the DSA. Internal voltage transitions arise, for example, from read, add, and write operations that comprise the digital signal averaging process in the DSA electronics. Because the sequence of such voltage transitions are repeated precisely for each digitization, the noise that they generate at the signal input is repetitive and synchronous with the signal waveform being averaged.

In order to minimize coherent noise, a substantial effort is typically invested during the design and development of DSA's to isolate the analog-to-digital conversion stage, and associated analog circuitry, from the digital circuitry associated with transfer and processing of the digital data produced by the ADC. With careful engineering design, it is possible to reduce internally-generated coherent noise to a fraction of 1 least significant bit (LSB) of the ADC. For example, the aforementioned FastFlight DSA from EG&G specifies that the maximum internally-generated coherent (correlated) noise to be equivalent to <0.2 mV rms noise at the ADC input. Given that 1 LSB spans 3.9 mV of input signal voltage for this instrument, the maximum coherent noise of 0.2 mV rms corresponds to an rms noise of 0.051 LSB. In this case, unless steps were taken to suppress the coherent noise, the limit to the signal-to-noise ratio that could be achieved, due to this coherent noise, would be 255/0.051=5000 for this 8-bit DSA, regardless of the number of waveforms that were included in the signal average. However, in terms of the available signal dynamic range that this would imply, if the minimum detectable signal is defined to have a signal-to-noise ratio greater than 5, say, then the maximum signal dynamic range that is possible with this coherent noise would be limited to ~1000. This assumes, of course, that enough waveforms are signal averaged so that any incoherent noise is rendered negligible.

Referring to the measurement results in FIG. 2, an illustration of the noise that is characteristic of that throughout the spectrum is shown in FIG. 3A, which portrays an expanded view of the portion of the spectrum from memory array bins 19,800 to 20,200. The noise illustrated in FIG. 3A appears to have some regularity, which is a signature of coherent noise. The measurement portrayed in FIG. 2 was repeated but with an average of 100 scans instead of 10. The noise in this spectrum, again as represented by contents of the memory array bins 19,800 to 20,200, is illustrated in FIG. 3B. The advantage of signal averaging in reducing the noise is apparent from a visual comparison of FIGS. 3A and 3B. In quantitative terms, the root-mean-square (RMS) of the noise of FIG. 3A is 0.32, while that of FIG. 3B is 0.27, a reduction by 16%. However, if this noise were random, or 'white' noise, then averaging 10 times more scans should theoretically reduce the noise by a factor equal to the square root of 10, or a factor of 3.33. Closer inspection of the noise in FIG. 3B clearly reveals a definite pattern, which is inconsistent with random noise, but which is characteristic of coherent noise, presumably originating from internal voltage transitions within the DSA itself.

Similarly, after-averaging 1000 and 10,000 scans, the noise in the same region of the spectrum is shown in FIGS. 3C and 3D, respectively. The coherent noise remains, and becomes more distinct, while the random component to the noise is reduced further, as expected, as more scans are signal averaged. The signal-to-noise ratio remains essentially the same as it was with a signal average measurement of 100 scans, due to the fact that the noise in the spectrum is dominated by the coherent noise, which is not reduced by conventional signal averaging techniques.

Various approaches have been devised in attempts to reduce coherent noise in DSA's. In the exemplary FastFlight DSA, for example, a constant voltage offset may be added to the signal input prior to the analog-to-digital conversion so that the coherent noise always falls below the minimum voltage corresponding to 1 LSB, provided that no other signal is present at the ADC input. With this approach, then, coherent noise may be eliminated in regions of the measured waveform that are very close to the baseline. However, the coherent noise is, nevertheless, fully manifest in regions of the waveform that have voltage amplitudes equal to or greater than the applied voltage offset, where the signal rises to the level of 1 LSB and above. Therefore, for signal levels in the measured waveforms that are at least as great as the applied constant voltage offset, this approach is unable to reduce the waveform distortions caused by coherent noise. Such waveform distortions due to coherent noise are especially problematic for relatively small signal levels, which are of amplitudes that are just great enough to correspond to the voltage level of 1, or several, LSB's. In these cases, the voltage excursions due to the coherent noise result in substantial noise on such small signal levels, which frustrates any attempt to obtain an accurate measurement, and limit the dynamic range of the DSA. Furthermore, such a voltage offset precludes the measurement of any signal with a magnitude less than that of the voltage offset, and therefore further limits the signal dynamic range capability of the DSA.

Another approach that has been used to reduce coherent noise in DSA's is that of noise filtering. It is well known to those skilled in the art that coherent noise in a DSA is sometimes composed of a limited and relatively well defined range of frequency components. It is sometimes advantageous, then, to apply a frequency filter, implemented either with hardware or with software, which is optimally tailored to reduce the frequency components of the coherent noise in the measured waveforms. Unfortunately, such filtering techniques unavoidably distort all features in the waveform, including the desired signal waveform characteristics, at least to some extent, and such distortion of the desired waveform is often unacceptable.

Still another approach to reducing coherent noise in DSA's is that of background subtraction. Essentially, this technique entails a measurement of the coherent noise spectrum without the presence of the signal waveform. Then, the measured coherent noise spectrum is subtracted from a measurement of a signal waveform, leaving, in principle, the signal waveform without coherent noise. This technique works well provided that the coherent noise spectrum is the same regardless of whether signal is present or not. Unfortunately, this is usually not the case. For example, for the FastFlight DSA from EG&G, the coherent noise is specified to be only a fraction of a least-significant-bit in magnitude. Therefore, without signal present, it is possible to adjust the zero-level offset to one extreme condition between two bit-transition boundaries, so that excursions from this zero-level due to the coherent noise never cross a digitizer bit transition, and, therefore, never appears in a measurement of the coherent noise spectrum. Alternatively, it is possible to adjust the zero-level offset to a voltage close to that of a bit transition, so that coherent noise produces excursions above and below the bit transition, resulting in a background spectrum that is characteristic of the coherent noise spectrum with this offset level. Clearly, the coherent noise that is manifest at any point in the spectrum of a measured signal waveform will depend strongly on the actual signal level that is present at that point in the signal waveform. Therefore, the subtraction of a background coherent noise spectrum from a signal waveform will only be effective for the portions of the signal waveform that are similar in amplitude, relative to a bit transition, as the zero-offset level with which the background coherent noise spectrum was measured, and therefore, such background subtraction is of limited utility. Even further, such background coherent noise subtraction may, in fact, result in an actual increase in coherent noise for some other portions of the measured signal spectrum, specifically, with amplitudes that correspond to voltage levels between two bit transitions, and, therefore, which would have appeared to be relatively free of coherent noise without the coherent noise background subtraction.

In summary, there has not been available a satisfactory solution to the reduction of internally-generated coherent noise in repetitive signal waveforms measured with digital signal averagers. Therefore, the signal-to-noise ratio and signal dynamic range that may be achieved with current state-of-the-art DSA's has been limited. The present invention described herein provides for the reduction of such coherent noise without any of the disadvantages of prior methods and apparatus.

Accordingly, it is one object of the present invention to provide devices and methods for the reduction of coherent noise in repetitive signal waveforms measured by digital signal averagers.

Another object of the present invention is to provide devices and methods for the reduction of coherent noise in repetitive signal waveforms measured by DSA's in real time, that is, during the signal waveform measurement and averaging process.

A still further object of the present invention is to provide devices and methods for the reduction of coherent noise in repetitive signal waveforms measured by DSA's that maintain the signal waveform fidelity for all signal levels.

Another object of the present invention is to provide devices and methods that are effective at reducing coherent noise in repetitive signal waveforms measured by DSA's at any setting of the voltage zero-offset level.

Yet another object of the present invention is to provide devices and methods for the reduction of coherent noise in repetitive signal waveforms measured by a DSA while maintaining the speed with which signal waveforms can be measured and signal averaged by the DSA.

Other objects and advantages over the prior art will become apparent to those skilled in the art upon reading the detailed description together with drawings as described as follows.

SUMMARY OF THE INVENTION

A digital signal averager (DSA) for digitizing and digital signal averaging a repetitive analog waveform is provided. Specifically, a DSA is provided that includes devices and methods which enable signal averaging to be accomplished while reducing internally-generated coherent noise without suffering any of the disadvantages associated with the prior art. Fundamentally, the apparatus and methods of the present invention provides means to introduce a known phase offset between a signal waveform being measured, and the repetitive pattern of internally generated digital voltage transitions that give rise to coherent noise in a signal waveform measured with a DSA. The known phase offset is different for different scans of the repeated waveform, such that the signal at any particular point in the waveform is digitized in each scan during a different phase of the cycle of digital data transfer, processing, and storage associated with the signal-averaging sequence. The known phase offset of each scan is properly accounted for during the summation, or signal-averaging, process, so that each scan maintains coherency with all other measured signal waveforms during the summation process. Hence, each point in the signal waveform will be sampled during each scan with a different value, that is, during a different phase, of the repetitive coherent noise background; hence, the coherent noise will be, essentially, averaged as a result of this process. Consequently, the coherent noise in the signal-averaged waveform is reduced by averaging according to apparatus and methods of the present invention, thereby improving the signal-to-noise ratio and signal dynamic range of such measurements more effectively than with previous methods.

In one preferred embodiment of the present invention, a DSA is provided which is configured to generate a trigger signal to stimulate a response signal waveform, from an external experiment, that is to be digitized and signal-averaged with the DSA. Specifically, this preferred embodiment comprises an analog-to-digital converter (ADC); a histogram memory array for recording digitized signal waveforms; a processing device for summing consecutive signal waveforms as they are digitized; a timing device for timing the ADC digitization intervals, for timing the sequence of data transfer, summation, and recording processes, for generating a Start signal output to start a new scan, and for controllably synchronizing all of these processes with each other; and a trigger delay device for generating a trigger signal after a variable time delay relative to the Start signal of the timing device. The delayed trigger signal is output to an experiment to stimulate a response signal that is to be recorded and signal averaged.

In a preferred method of operation of this embodiment of the present invention, the timing device generates a Start signal to initiate a new signal waveform measurement sequence, i.e., a new scan. In response to this Start signal, the trigger delay device generates a trigger signal after a first trigger delay time that is defined to be an integral number of ADC digitization intervals. The experiment produces a signal waveform of interest (that is, the portion of the response signal waveform that is it be recorded) in response to this delayed trigger signal, generally after a response time following the delayed trigger signal. The timing device also begins transmitting timing signals to the processing device that begins a scan sequence of ADC data transfer, summation, and storage into a memory array. These timing signals are generated by the timing device a period of time after the Start signal that is less than or equal to the sum of the first trigger delay time and the experiment response time. Therefore, for the first scan, the sequence of data transfer, summation, and storage begins at or before the time that the beginning of the signal waveform of interest appears at the ADC input. The ADC converts the analog signal at the ADC input to a digital data value every ADC interval. The processing device sums each digital data value with the current contents of the memory storage element at the memory address that corresponds to the same point in time in the signal waveform as each new ADC digital data value, respectively. This process continues for the number of ADC intervals that is necessary to capture a scan of the signal waveform of interest. Because each memory location is associated with the time at which the corresponding analog-to-digital conversion occurred, and the digital data values are added in histogram fashion therein, the memory locations of such a histogram memory array are commonly referred to as 'time bins'.

After the first scan is complete, a second scan may begin in a manner identical to the first scan, except that the trigger delay time may be changed by some integral number of ADC intervals to a second time delay. Hence, the time of arrival of the signal waveform at the ADC input, relative to the Start time, will be different for this second scan compared to that of the first scan, by an amount equal to the difference in trigger delay time between the first and the second scans. Nevertheless, according to the present invention, the timing device transmits the timing signals, which begin the sequence of ADC data transfer, summation, and storage, to the processing device, at the same time, relative to the Start signal, as in the first scan. With respect to this sequence, then, the signal waveform will be shifted in time for the second scan relative to that of the first scan, by an amount equal to the difference in the trigger delay time between the first and second scans. One aspect of the present invention is that the processing device and memory array architectures are configured so as to account for the time shifts between scans during the summation of each new ADC data value in the current scan with the sum of previous data values that correspond to the same point in time on the signal waveform. Subsequent scans of the signal averaging process may be executed similarly, that is, with different values of the trigger delay time, while the sequence of digitization, data transfer, summation, and storage is performed for each and every scan at the same time relative to the Start signal as for the first scan.

Coherent noise generated internal to the DSA will be synchronous and repetitive, and therefore always in the same relative phase, or coherent, with respect to the Start time, but not with respect to the trigger delay time, since the trigger delay time may, in general, be different, relative to the Start time, for each scan, in this embodiment of the present invention. In contrast, the repetitive signal waveform is coherent and synchronous, that is, always in the same relative phase, with respect to the delayed trigger signal, but, therefore, not with respect to the Start time, due to the different delay trigger offsets for different scans. The result is that any particular point on the repetitive signal waveform will be sampled and digitized during a different phase of the coherent noise with each scan. Consequently, the contribution to the average waveform measurement from coherent noise at any particular point in the signal waveform will tend to some average value that is the same for all points, i.e., the coherent noise will be reduced by the signal averaging methods and devices of this embodiment of the present invention.

In another preferred embodiment of the present invention, a DSA is provided which is configured to generate a trigger signal to stimulate a response signal waveform that is to be digitized and signal-averaged with the DSA. Specifically, this preferred embodiment comprises an analog-to-digital converter (ADC); a histogram memory array for recording digitized signal waveforms; a processing device for summing consecutive signal waveforms as they are digitized; a timing device for timing the ADC digitization intervals, for timing the sequence of data transfer, summation, and recording processes, for generating a Start signal output, which directly acts as the trigger signal to stimulate a response signal waveform from an experiment, and for controllably synchronizing all of these processes with each other; and a scan delay device for introducing a variable time delay which delays the timing signals output by the timing device that time the sequence of data transfer, summation, and recording processes during each scan.

In a preferred method of operation of this embodiment of the present invention, the timing device generates a Start signal that triggers an external experiment to generate a new signal waveform. The timing device then, generally after some experiment response time, begins to generate timing signals that enable the sequencing of data transfer, read, add, and write operations, which comprise a scan measurement and signal averaging process, according to conventional signal averaging methods. However, in accordance with the devices and methods of this embodiment of the present invention, these latter timing signals may be delayed by a so-called scan delay time as determined by the scan delay device. This scan delay time may be different for each scan comprising a signal average measurement; however, the scan delay time is constrained to be an integral multiple of ADC intervals. In order to ensure that each scan in a signal average measurement includes the entire signal waveform of interest, it is necessary, in this embodiment of the present invention, that the timing device begins the scan measurement process some period of time before the arrival of the signal waveform of interest during any one scan. Because the timing device generates these timing signals in the same phase relative to the Start signal for all scans comprising a signal averaging measurement, the minimum period of time required between the Start signal, and the timing signals output by the timing device that time a scan measurement sequence, is given by the maximum scan delay time that is used in the signal averaging measurement. In this case, then, when the scan delay time is the minimum delay that is used for any scan in a signal average measurement, any signal at the ADC input will be digitized and recorded for a period of time prior to the arrival of the signal waveform of interest; this period of time needs to be at least as long as the maximum scan delay time that is used for any scan of the signal average measurement. Conversely, when the scan delay time is the maximum delay that is used by any scan in the signal average measurement, the time that the ADC input is recorded prior to the arrival of the signal waveform of interest is a minimum, and may even be 0, in which case, the scan sequence begins at the point in time when the signal waveform of interest first arrives at the ADC input. The maximum scan delay time that is optimum to be used in a signal averaging measurement will depend on the number of unique noise amplitude levels that comprise the coherent noise pattern existing in a particular DSA.

In response to the Start signal, then, the experiment produces a signal waveform of interest, generally after a response time following the Start signal, i.e., the trigger signal. The timing device also begins transmitting timing signals that control the sequence of data transfer, read, add, and write operations that comprise each scan. As discussed above, the timing device begins transmitting these timing signals a period of time before the arrival of the signal waveform of interest. This period of time corresponds at least to the maximum scan delay time that will be used in the signal average measurement. These timing signals are then routed through the scan delay device, in which they are delayed by a first scan delay time that is an integral number of ADC intervals, before being routed to the processing and memory devices. The ADC converts the analog signal at the ADC input to a digital data value every ADC interval. The processing device sums each digital data value with the current contents of the memory storage element at the memory address that corresponds to the same point in time in the signal waveform as each new ADC digital data value, respectively. This process continues for the number of ADC intervals that is necessary to capture a scan of the signal waveform of interest.

After the first scan is complete, a second scan may begin in a manner identical to the first scan, except that the scan delay time may be changed by some integral number of ADC intervals to a second scan delay time. Hence, while the time of arrival of the signal waveform at the ADC input, relative to the Start time, will be the same for this second scan as that of the first scan, the scan recording and signal averaging sequence begins at a point in time relative to the Start signal that is different from that of the first scan, by an amount corresponding to the difference in the scan delay times between the first and the second scans. Therefore, the sequence of operations that comprise a scan will be shifted in time relative to the signal waveform, that is, relative to the Start signal, for the second scan relative to that of the first scan, by an amount equal to the difference in the trigger delay time between the first and second scans. One aspect of the present invention is that the processing device and memory array architectures are configured so as to account for the time shifts between scans during the summation of each new ADC data value in the current scan with the sum of previous data values that correspond to the same point in time on the signal waveform. Subsequent scans of the signal averaging process may be executed similarly, that is, with different values of the scan delay time, while the signal waveform is generated for each and every scan at the same time relative to the Start signal as for the first scan.

Coherent noise generated internal to the DSA will be synchronous and repetitive, and therefore always in the same relative phase, or coherent, with respect to the time that the scan recording sequence begins, as defined by the scan delay time, but not with respect to the Start time, since the scan delay time may, in general, be different, relative to the Start time, for each scan, in this embodiment of the present invention. In contrast, the repetitive signal waveform is coherent and synchronous, that is, always in the same relative phase, with respect to the Start, or trigger, signal, but, therefore, not with respect to the scan recording sequence, due to the different scan delay times for different scans. The result is that any particular point on the repetitive signal waveform will be sampled and digitized during a different phase of the coherent noise with each scan. Consequently, the contribution to the average waveform measurement from coherent noise at any particular point in the signal waveform will tend to some average value that is the same for all points, i.e., the coherent noise will be reduced by the signal averaging methods and devices of this embodiment of the present invention, similarly to the embodiment of the present invention discussed previously.

The signal averaging process, as described above according to the embodiments and methods of operation of the present invention, will produce the same reduction in random noise as is realized with conventional signal averaging (assuming that the same number of scans are signal averaged as with conventional signal averaging). However, in contrast to conventional DSA's, the apparatus and methods of the present invention uniquely provide means to reduce coherent noise, which originates from within the DSA, as well as random noise.

BRIEF DESCRIPTION OF THE FIGURES

FIG. 13F illustrates a timing diagram associated with one preferred method of operating a particular embodiment of a DSA of the present invention, for the $32^{nd}$ scan of a signal averaging measurement.

DETAILED DESCRIPTION OF THE INVENTION AND THE PREFERRED EMBODIMENTS

Figure 4A:
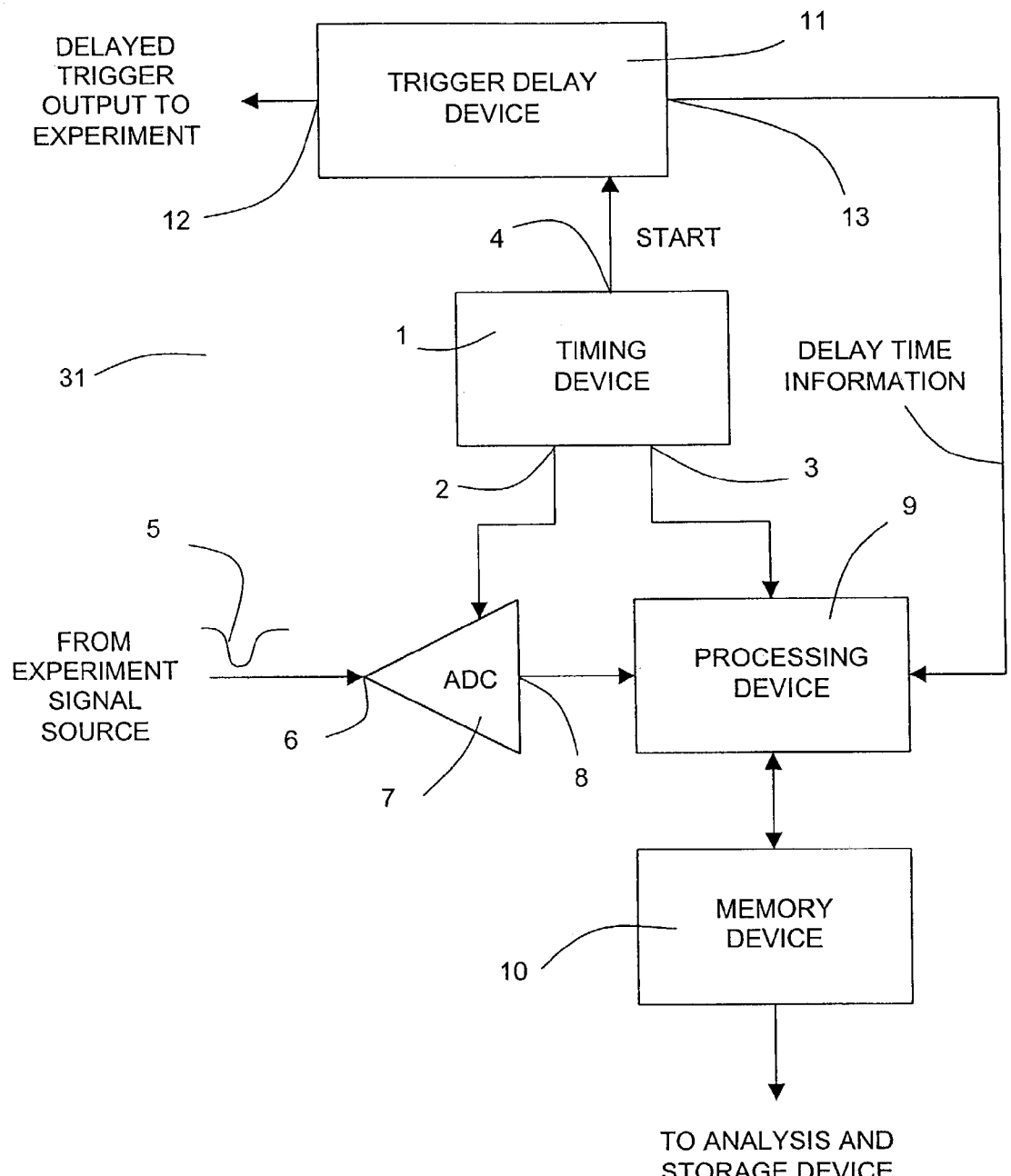
FIG. 4A is a diagram of a DSA according to one preferred embodiment of the present invention.

A digital signal averager configured according to one preferred embodiment of the present invention is shown schematically in FIG. 4A, and consists essentially of an ADC 7, a timing device 1, a processing device 9, a memory device 10, and a trigger delay device 11.

The timing device 1 includes a precision clock and auxiliary timing circuitry. One function of timing device 1 is to provide a timing signal at output 2 to control the time interval, $T_{Bin}$, between consecutive analog-to-digital conversions by the ADC 7.

A second function of timing device 1 is to provide a Start signal at output 4 that is synchronized with the ADC digitization cycle. This Start signal is generated at the initiation of a new scan measurement sequence, and is provided to the input of the trigger delay device 11. In response to this Start signal, the trigger delay device 11 produces a trigger signal at output 12, which is routed to the external experiment in order to stimulate a signal response 5 from the external experiment. This trigger signal is delayed relative to the Start signal by a time delay, $T_{Delay}$, that is constrained to be an integral number of ADC digitization intervals, that is, $T_{Delay}=N_{Delay} T_{Bin}$, where $N_{Delay}$ is an integer, which may be different for each scan.

A third function of timing device 1 is to provide timing signals at output 3, which are input to the processing device 9, that control the initiation and subsequent sequence of data transfer, summation, and storage processes, that are executed during each scan by the processing device 9. This sequence is initiated by timing device 1, generally, after a period of time, $T_{Scan-Init}$, relative to the time of the Start signal at output 4 of timing device 1. The data values that result from these operations are stored in memory storage elements of memory array device 10.

Figure 4B:
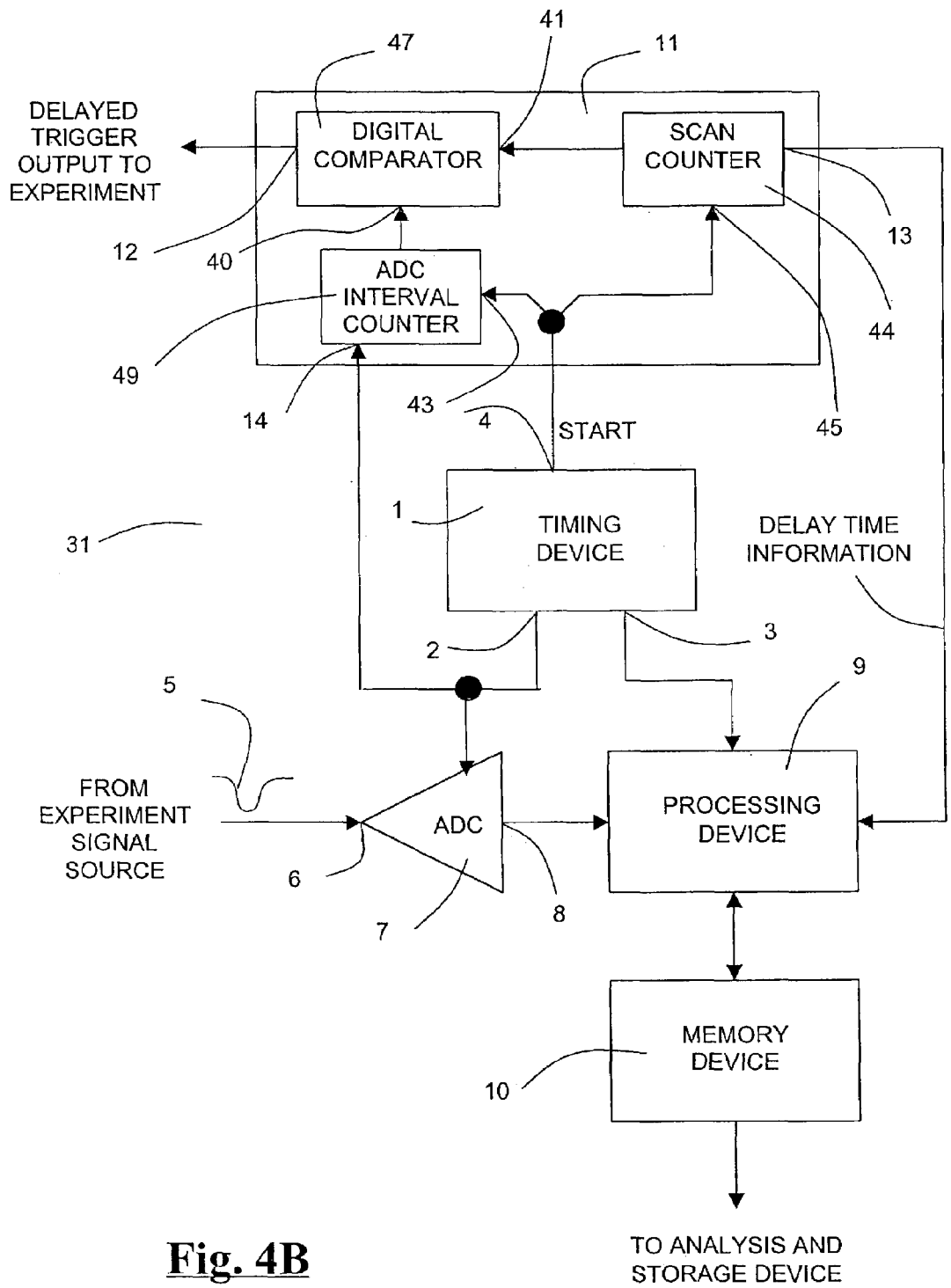
FIG. 4B is a diagram of a DSA according to one preferred embodiment of the present invention, illustrating one possible electronic arrangement that provides a variable trigger delay offset for each scan, starting from 0 nanoseconds and incrementing the trigger delay by 1 ADC interval with each subsequent scan.

Because the trigger delay is constrained to be an integral number of ADC intervals, a convenient protocol for varying the trigger delay time from one scan to the next is to increment the trigger delay time by 1 ADC interval from a minimum number of ADC intervals to some maximum number of ADC intervals, as required by the repeat period of the coherent noise pattern. Accordingly, one example implementation of a trigger delay device 11, according to one aspect of this embodiment of the present invention, is illustrated conceptually in FIG. 4B. As shown in FIG. 4B, the trigger delay device 11 may be configured essentially with an ADC interval counter 49, a scan counter 44, and a digital comparator 47. Prior to the Start signal at output 4 of timing device 1, of the first scan of a signal averaging measurement, the digital comparator 47 output 12 is kept at a logical 'false' state, inhibiting any triggers from being output to the experiment, and the scan counter 44 is reset to its maximum possible value, i.e., all digital outputs at a logical '1'. Then, when the Start signal is generated at the output 4 of timing device 1 in order to begin the first scan, the scan counter 44 registers one count, which results in the scan counter 44 output to 'rolling over' to an output of 0, which is routed to the input 41 of digital comparator 47. Simultaneously, the Start signal at output 4 of timing device 1 is also routed to the reset input 43 of the ADC interval counter 49, which results in the ADC interval counter 49 being initialized to a count of 0, which is routed to the input 40 of digital comparator 47. Therefore, the digital comparator 47 immediately outputs a logical 'true' at output 12, which is routed to the experiment to initiate the generation of a signal waveform. For this first scan, then, there is essentially 0 delay between the Start signal and the delayed trigger output to the experiment.

For the second scan, the Start signal at output 4 of timing device 1 causes the scan counter 44 to increment to 1, which appears at input 41 of digital comparator 47. The Start signal also again resets the ADC interval counter 49 to an initial count of 0, which appears at the input 40 of digital comparator 47. Because input 41 of digital comparator 47 is 1, while input 40 of digital comparator 47 is 0, no trigger signal is generated at output 12 of digital comparator 47. However, the ADC interval counter is incremented to 1 counts upon the next ADC digitization, and then the digital comparator 47 generates a trigger signal at output 12, since now both inputs are equal at 1 count. Hence, the trigger signal to the experiment is delayed by 1 ADC interval with respect to the Start signal.

For the third, and subsequent, scans, this process repeats, whereby the delayed trigger signal at output 12 of the digital comparator 47 is delayed by 1 more ADC interval for each subsequent scan than for the previous scan. Again, this is but one specific conceptual implementation according to the methods and devices of the present invention, and those skilled in the art will recognize that many variations of this arrangement will be possible with which to accomplish the same result. For instance, for a particular DSA, it may be advantageous to increment the scan counter 44 by 2 counts rather than 1 count for each scan, in order that the trigger delay remain the same for each pair of consecutive scans. This scheme may be advantageous in those situations where the pattern of coherent noise is a composite of two different patterns, each pattern possibly produced alternately with every other scan (as discussed below). This is easily accomplished, for example, by routing the 2's digit output of the scan counter 44 to the 1's digit input of the digital comparator 47, routing the 4's digit output of the scan counter 44 to the 2's digit input of the digital comparator 47, etc.

The number of scans that are optimum to sum before the trigger delay returns to 0 (or whatever the minimum trigger delay time is used) to begin the cycle again, depends on the details of the coherent noise pattern that is manifest in a particular DSA. For example, it may be only necessary, for maximum reduction in coherent noise, to sum 16 scans, each with different trigger delay value, which would be appropriate for coherent noise that has a period corresponding to 16 ADC intervals, before repeating the cycle. In this case, the scan counter may be configured as a 4-bit counter, which counts from 0 to 15 before returning to 0 on the next count, in response to the 17$^{th}$ Start signal at output 4 of timing device 1. In another example, where two different patterns of coherent noise are produced alternately with every other scan, it may be necessary to double the number of scans that would otherwise be required if only a single pattern of coherent noise was produced. In this case, if the repeat pattern for either of the coherent noise patterns is 16 ADC intervals, then the trigger delay would need to vary by 1 ADC interval from 0 to 15 ADC intervals, but the trigger delay may only be incremented every other scan, so that 32 scans would be required for maximum reduction in the coherent noise. The scan counter would then need to reset to 0 every 33$^{rd}$ scan. In this case, the scan counter may be configured as a 5-bit counter, which counts from 0 to 31 (for a total of 32 scans) before returning to 0 on the next count (the 33$^{rd}$ scan), in response to the 33$^{rd}$ Start signal at output 4 of timing device 1.

Now, in one preferred method of operation of this embodiment of the present invention, a signal averaging measurement sequence may begin by loading zeros into all memory storage locations. For the first scan, $N_{Delay}$ is set equal to a first integer value, which may arbitrarily be 0 for the sake of simplicity, in which case, for this first scan, the delayed trigger signal occurs simultaneously with the Start signal, as described in the previous discussion. In response to the delayed trigger signal, the external experiment generates a response signal waveform, which is routed to the input 6 of the ADC 7. Generally, the portion of the response signal waveform that is of interest will arrive at the input 6 of the ADC 7 a period of time, $T_{Response}$, following the receipt of the delayed trigger signal by the experiment. Therefore, in order to ensure that the portion of the digitized response signal waveform that is of interest is included in a scan, $T_{Scan-Init}$ is required to be less than or equal to the sum of the trigger delay time and the experiment response time, i.e., $T_{Scan-Init} \leq T_{Delay}+T_{Response}$. Under the assumption that, for this first scan, $T_{Delay}=0$, this requirement becomes $T_{Scan-Init} \leq T_{Response}$. In any case, the value that is chosen for $T_{Scan-Init}$ is kept constant for all subsequent scans of the signal average measurement, as well as for this first scan.

For the second scan, $N_{Delay}$ may be set equal to an integer value that is different from that of the first scan. For example, $N_{Delay}$ may be incremented by 1, in which case, for this second scan, the trigger signal to the experiment is delayed by 1 more ADC interval relative to the Start signal, than for the first scan. Therefore, the response signal waveform is generated at the input 6 of the ADC 7 at a time relative to the Start signal that is one ADC interval later in this second scan than in the first scan. However, as discussed above, the sequence of data transfer, summation, and storage operations is commenced for this second scan at the same point in time relative to the Start signal as for the first scan. Hence, it is the second ADC value of this second scan that corresponds to the same point in time on the signal waveform as the first ADC data value that was processed in the first scan. Similarly, the third ADC value of this second scan corresponds to the same point in time as the second data value of the first scan, and so on for all data values of the second scan.

In order to properly sum the second scan with the first scan, according to one aspect of the present invention, the processing device takes the relative time shift between the scans into account when summing each new ADC data value in the second scan with the data value of the first scan that corresponds to the same point in time on the signal waveform as the new data value of the second scan. This may be accomplished in a number of ways. For example, according to one aspect of this embodiment of the present invention, as illustrated in FIG. 4, the trigger delay device provides at output 13 the value of each current trigger delay that is being used in the current scan, and this information is transferred to an input of the processing device 9, which then compensates for the offset as the spectrum is summed with previously measured spectra.

In another preferred aspect of this embodiment, a fixed protocol may be established whereby the initial trigger delay time for the first scan of each signal average measurement is always the same, such as 0, with subsequent delays being incremented by a fixed number of ADC intervals, such as by 1 interval, in subsequent scans. Such a fixed protocol alleviates the requirement to communicate the value for the trigger delay in any particular scan by the trigger delay device to the processing device, since the processing device only needs to keep track of the scan number of the current signal averaging measurement to ascertain the current trigger delay. Other protocols may be envisioned that accomplish the same result of properly accounting for the time shifts between scans during the signal averaging process.

For the third and any subsequent scans, $N_{Delay}$ may similarly be set equal to an integer value that is different from that of the previous scans. For example, $N_{Delay}$ may be incremented by 1 for each subsequent scan, in which case, for each such subsequent scan, the trigger signal to the experiment is delayed by 1 more ADC interval relative to the Start signal, than for the previous scan. Therefore, the response signal waveform is generated at the input 6 of the ADC 7 at a time relative to the Start signal that is shifted by one ADC interval for each scan compared to the previous scan, relative to the Start signal. As a new data value is processed during any particular scan, then, according to one aspect of this embodiment of the present invention, the processing device compensates for the time shift of the signal waveform for that particular scan due to the delayed trigger value that was used for that scan, in order to properly sum the new data value with the sum of previous scan data values that correspond to the same point in time on the signal waveform.

Because the sequence of data transfer, summation, and storage operations is repeated with the same relative phase with respect to the Start signal for each and every scan of the signal average measurement, the noise that is generated by this sequence of operations is repeated in each scan with the same relative phase with respect to, or, in coherence with, the Start signal. However, due to the different trigger delay values that are used for each scan, each point on the signal waveform is digitized during a correspondingly different phase of this coherent noise pattern. Therefore, the level of the coherent noise that is present in any particular point on the signal waveform will tend to be an average of a number of coherent noise levels, where the number of coherent noise levels that are 'sampled', in general, corresponds to the number of different trigger delay values that were employed in the signal averaging process according to the devices and methods of the present invention. As this number increases, therefore, this averaging process reduces the coherent noise in the signal waveform accordingly.

Now, as indicated in a previous discussion, the pattern of coherent noise that is generated by the repetitive sequence of digitization, data transfer, summation, and storage processes will often have a repeat period that is much less than the time duration of a scan. Specifically, it will often be the case that the pattern of coherent noise repeats within the course of a scan every $M_{CN}$ number of sequential ADC digitization intervals, where $M_{CN}$ is much less than $M_{scan}$, the number of sequential ADC digitization intervals comprising a scan. Therefore, in such cases, it is only necessary to increment the trigger delay time parameter, $N_{Delay}$, by 1 from 0 to $(M_{CN}-1)$, in order to minimize coherent noise in the signal averaged waveform record. From another perspective, $M_{CN}$ represents the number of discrete amplitude levels of coherent noise that are present at any particular value of the waveform signal level. Therefore, by incrementing the trigger delay time parameter, $N_{Delay}$, by 1 from 0 to $(M_{CN}-1)$, each point oh the signal waveform is digitized with every value of the coherent noise that is possible for the signal level at that point in the signal waveform. In this case, the coherent noise is minimized at each point in the signal waveform.

Furthermore, it will be appreciated that, frequently, the number of scans, $N_{Ave}$, that are to be included in a particular signal average measurement, will be much greater than the number of scans, $M_{CN}$, that are sufficient to minimize the coherent noise in the final average. In such cases, minimization of the coherent noise in the signal averaged waveform only requires that the number of scans measured with each value of the delay time parameter, $N_{Delay}$, is the same for each value of $N_{Delay}$. This will ensure that all amplitude levels of the coherent noise pattern are sampled equally, and therefore optimally averaged, at each point in the signal waveform. However, even when all amplitude levels of the coherent noise pattern are not sampled exactly equally, at least some substantial reduction of the coherent noise is nevertheless typically achieved according to the present invention. For example, a situation will often occur in which the number of scans in the final averaged waveform, $N_{Ave}$, is not an integral multiple of $M_{CN}$, but where $N_{Ave}$ is nevertheless much greater than $M_{CN}$. In this situation, it is not possible to arrange that the number of scans measured with each value of $N_{Delay}$, from n=0 to n=$(M_{CN}-1)$, will be exactly the same. The best that can be achieved is to arrange for the number of scans that are measured with each of some values of $N_{Delay}$, to be INT($N_{Ave}/M_{CN}$), where INT indicates that number in the parenthesis is to be truncated to an integer number, while the number of scans that are measured with each of the other values of $N_{Delay}$, to be INT($N_{Ave}/M_{CN}$)+1. In this case, some values of $N_{Delay}$ will be used in 1 more scan than some other values of $N_{Delay}$. However, provided that $N_{Ave}$ is much greater than $M_{CN}$, then ($N_{Ave}/M_{CN}$) will be much greater than 1, and the impact on the reduction of the coherent noise, of some values of $N_{Delay}$ having been used in 1 more scan than other values of $N_{Delay}$ will be relatively small.

In situations in which $N_{Ave}$ is not much greater than $M_{CN}$, then the coherent noise will still be reduced, at least to some extent, with the methods and apparatus of the present invention. Nevertheless, in such situations, the coherent noise may be minimized if only the number of scans that are allowed in the average, $N_{Ave}$, is constrained to be an integral multiple of $M_{CN}$. In many situations, such a requirement may not be a serious constraint on the measurement protocol. For example, if $M_{CN}$=16, then a constraint may be placed on the number of scans $N_{Ave}$ that are signal averaged to be an integral multiple of 16. Then, if it were desired to average 1000 scans, the constraint may be that either 992 or 1008 scans per average be specified, either being the closest integral multiple of 16 to 1000, without significant consequences to the measurement process.

In any case, it will be appreciated that the order in which the trigger delay values are varied will make no difference to the effectiveness of the coherent noise reduction according to the devices and methods of the present invention. For example, one viable scheme is that ($N_{Ave}/M_{CN}$) number of scans are signal averaged with a fixed trigger delay value, and then this process is repeated with each of the other $(M_{CN}-1)$ number of trigger delay values in a manner that properly accounts for the trigger delays. Another equally effective scheme is to measure $M_{CN}$ number of scans, each with a different trigger delay, and sum them in a manner that accounts for the trigger delays of each scan; then, this process may be repeated for ($N_{Ave}/M_{CN}$) number of times.

Figure 1:
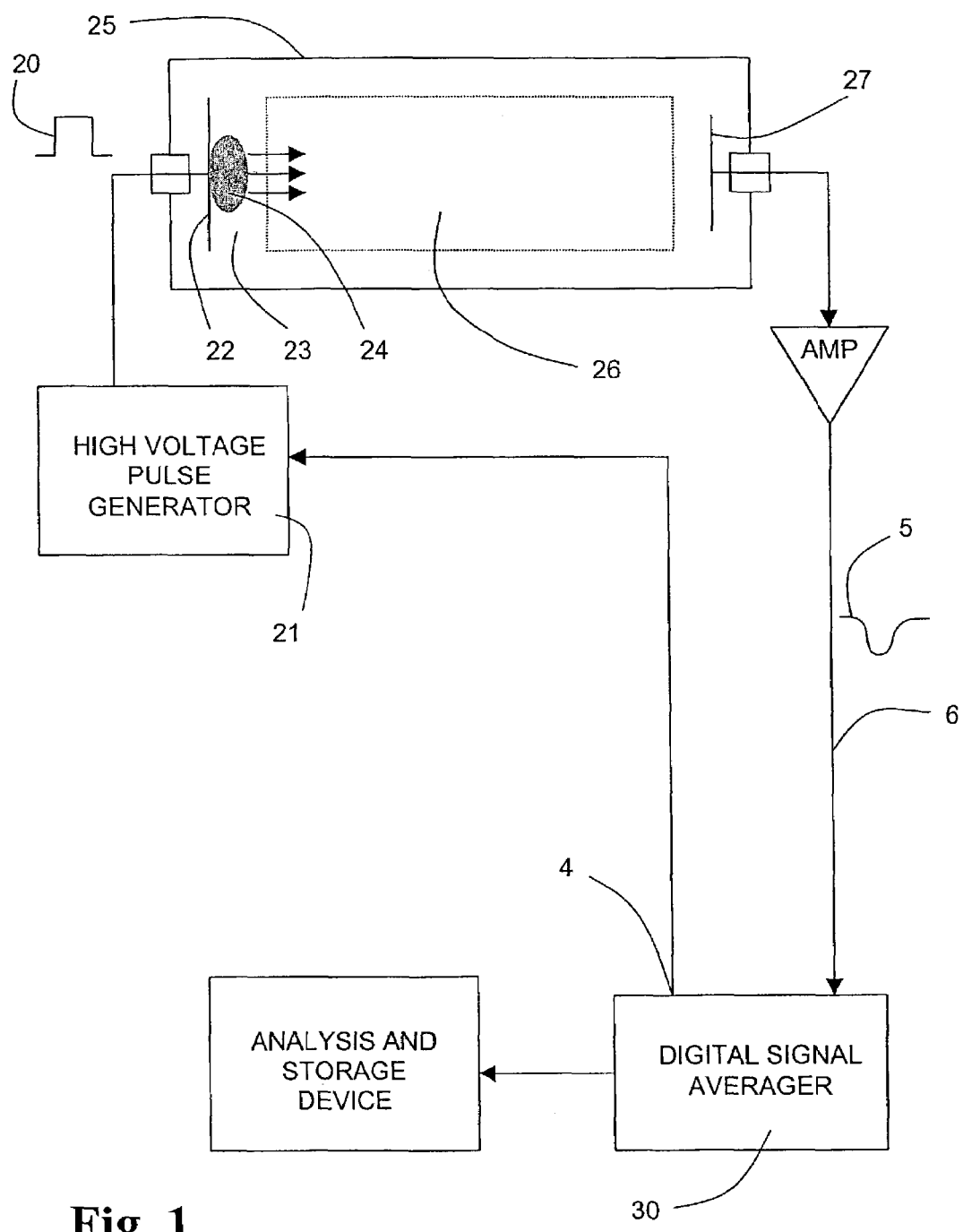
FIG. 1 is a diagram of one example application of a DSA: a time-of-flight mass spectrometer, which utilizes a DSA for signal recording and averaging of time-of-flight mass spectra.
Figure 5:
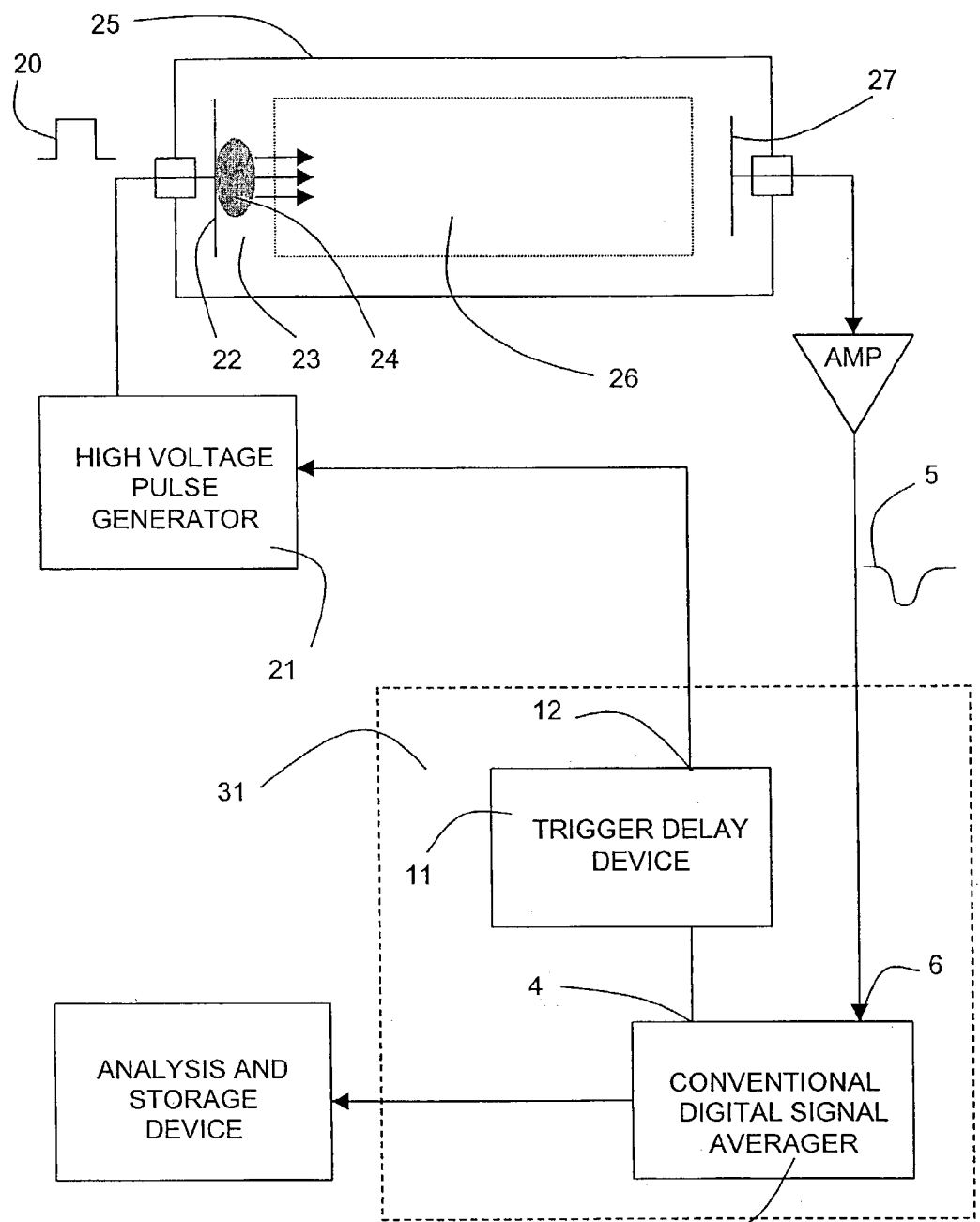
FIG. 5 is a diagram of one example application, the time-of-flight mass spectrometer of FIG. 1, which is configured with a DSA in accordance with essential apparatus and methods of the present invention.

The effectiveness of a DSA configured and operated in accordance with the devices and methods of the present invention may be demonstrated with the experimental arrangement illustrated in FIG. 5, which illustrates the former signal measurement and averaging scheme mentioned in the previous paragraph. Essentially, a programmable time delay device was incorporated into the experimental arrangement that was illustrated in FIG. 1, whereby the trigger signal at trigger output 19 of the conventional DSA is routed to the input 40 of the time delay device, rather than to the time-of-flight mass spectrometer, as in the conventional configuration of FIG. 1. After a programmed delay time, $T_{Delay}$, the time delay device 11 produces a trigger signal at output 12, which is input to the high voltage pulse generator 21. In response to this delayed trigger signal, the high voltage pulse generator 21 produces a voltage pulse 20, which is routed to an electrode 22 that forms one boundary plane the pulsing region 23. In response to this applied voltage pulse, ions are accelerated into the time-of-flight measurement chamber 26, and arrive at a detector 27 with a time dependence that is proportional to the square-root of their mass-to-charge ratio. As ions arrive at the detector 27, a signal 5, related to the number of ions present for each mass-to-charge ratio, is generated, which is introduced, after amplification, to the input 6 of the (conventional) DSA 30 for measurement and recording.

The conventional DSA 30 converts the analog signal 5 to a series of digital values with an ADC interval between conversions $T_{Bin}$ of, for example, 2 nanoseconds with a 500 MHz ADC. A number of such scans are typically signal averaged to improve the signal-to-noise ratio of the measurement. The voltage pulse 20 that begins each time-of-flight spectrum measurement is triggered by a signal at the DSA trigger output 4 in synchronization with the internal clock of the DSA. Therefore, each scan may easily be synchronized with all previous scans, which is necessary to achieve a valid signal average record of all the scans.

Figure 2:
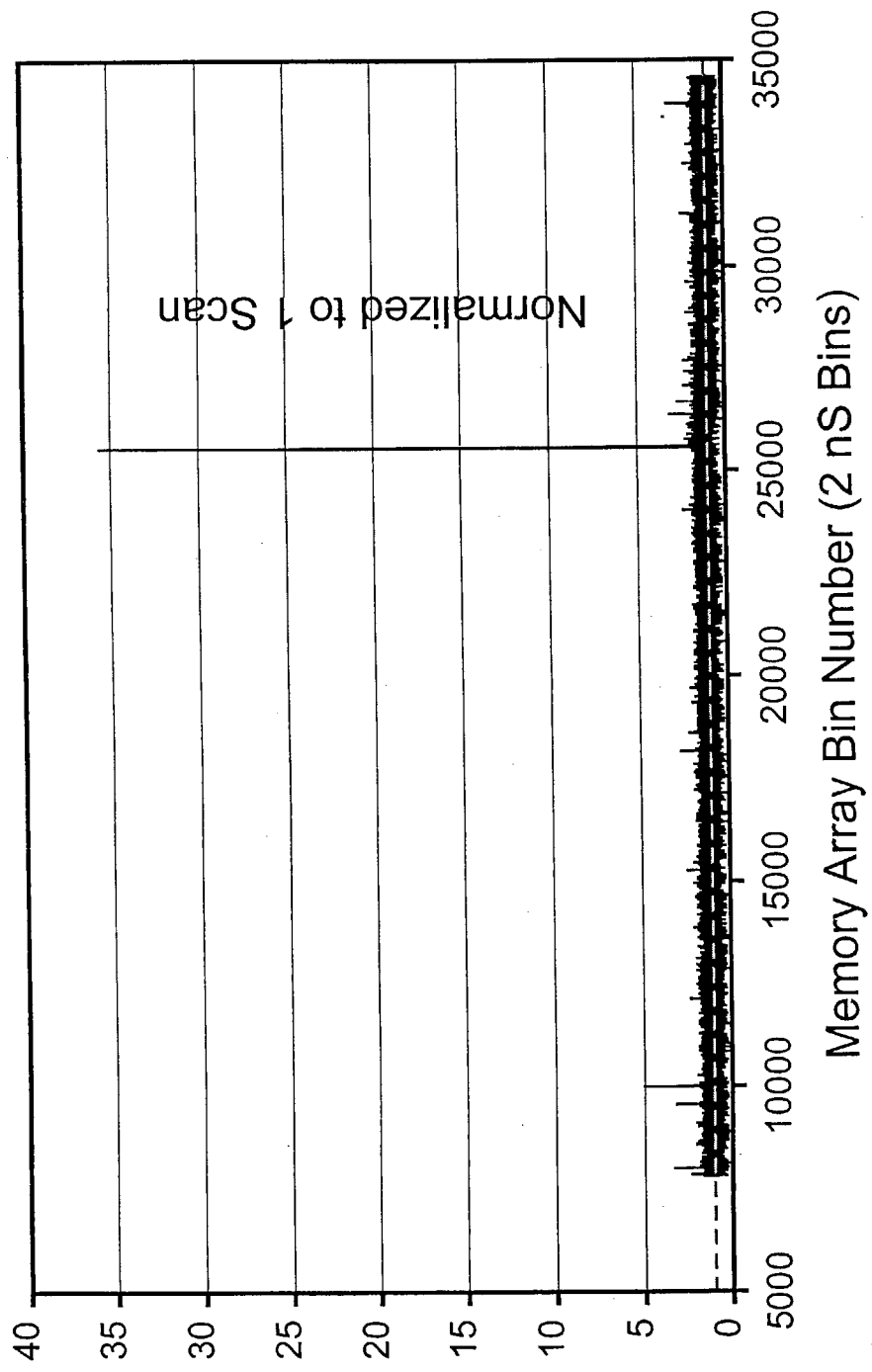
FIG. 2 illustrates a mass spectrum consisting of 10 scans of a signal waveform produced by the time-of-flight mass spectrometer of FIG. 1, using a conventional DSA.

In order to demonstrate the essential aspects of the present invention, a series of spectra, each consisting of an average of 625 scans, were measured with the experimental arrangement illustrated in FIG. 5. The same sample and the same measurement parameters and protocol were used for each as were used for the measurements of FIGS. 2 and 3, except that now, 625 scans are signal averaged per spectrum rather than 10,000, and a trigger delay device 11 is incorporated, which is programmed with a different trigger time delay, $T_{Delay}$'$N_{Delay}$ $T_{Bin}$, for each of the spectra. The ADC interval of the conventional DSA that was used for these measurements is 2 nanoseconds, i.e., $T_{Bin}$=2 nanoseconds; therefore, the trigger delay used for each spectrum is a different integral multiple of 2 nanoseconds.

Figure 3A:
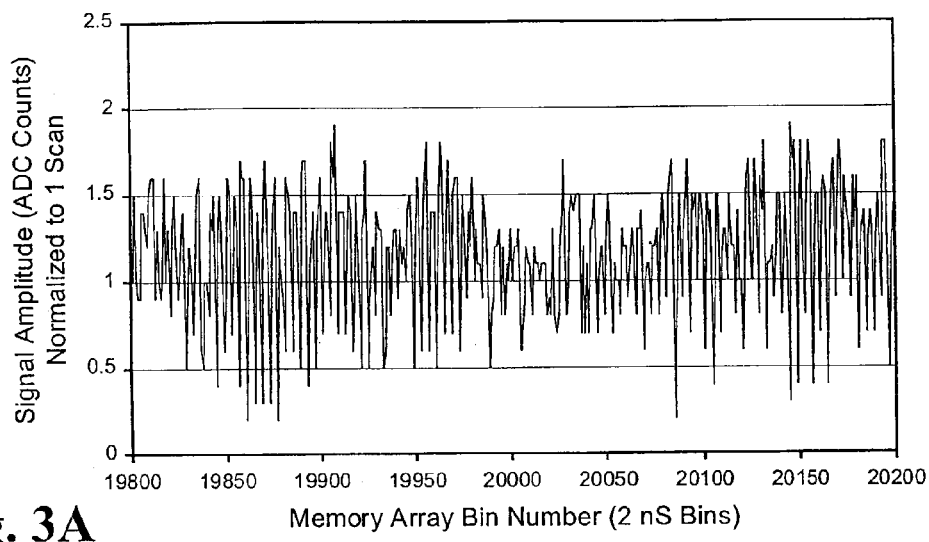
FIG. 3A illustrates an expanded view of a portion of the mass spectrum of FIG. 2, which exhibits noise characteristics that are typical throughout the spectrum.
Figure 3B:
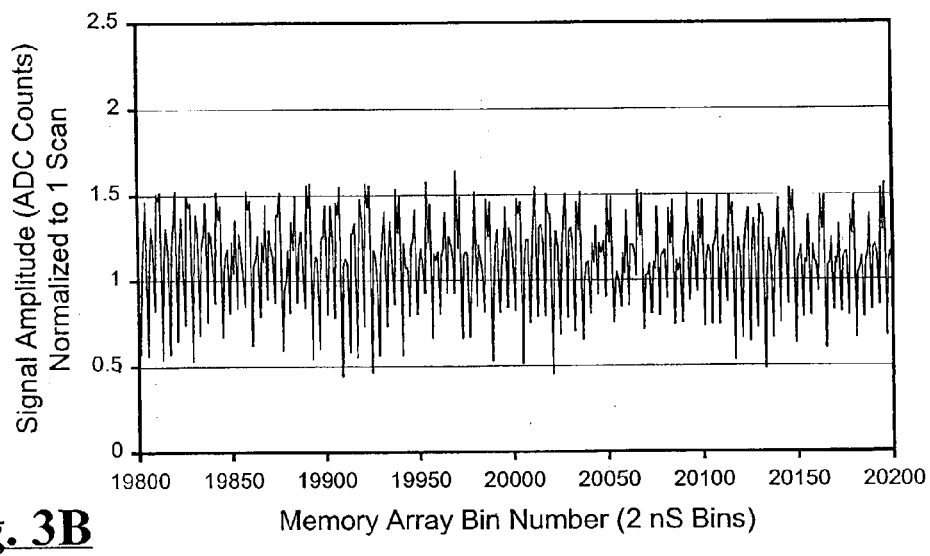
FIG. 3B illustrates an expanded view of the same portion of a mass spectrum as in FIG. 3A resulting from signal averaging 100 scans of the signal waveform of FIG. 2, using a conventional DSA.
Figure 3C:
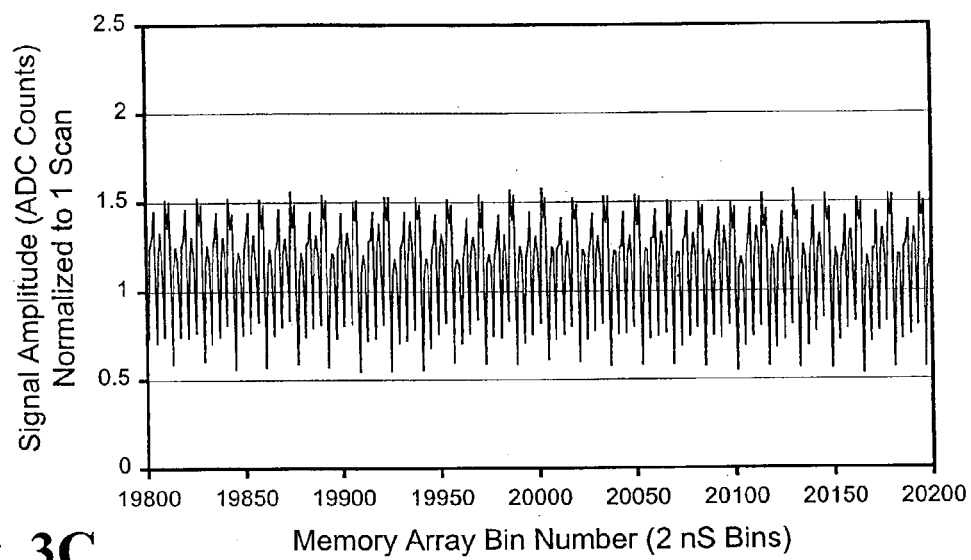
FIG. 3C illustrates an expanded view of the same portion of a mass spectrum as in FIG. 3A resulting from signal averaging 1,000 scans of the signal waveform of FIG. 2, using a conventional DSA.
Figure 3D:
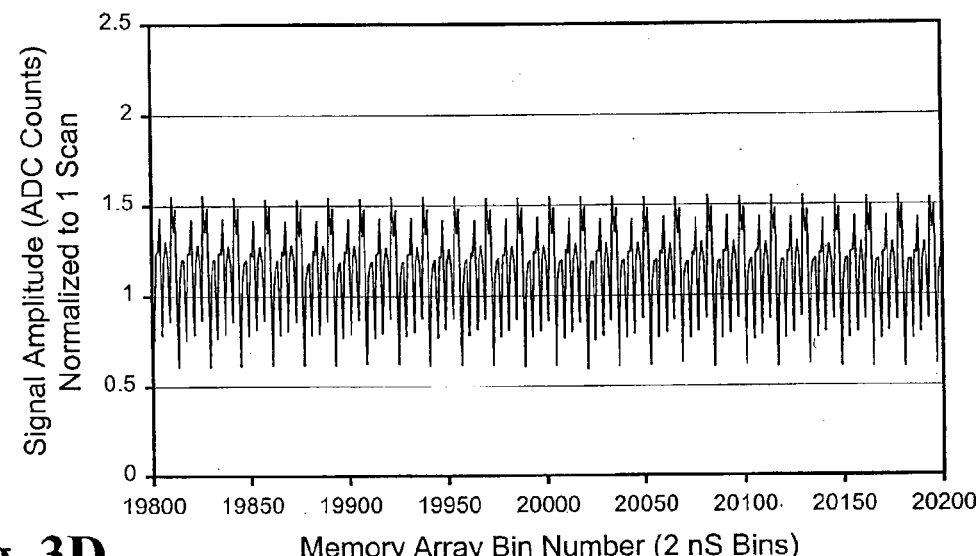
FIG. 3D illustrates an expanded view of the same portion of a mass spectrum as in FIG. 3A resulting from signal averaging 10,000 scans of the signal waveform of FIG. 2, using a conventional DSA.
Figure 6A:
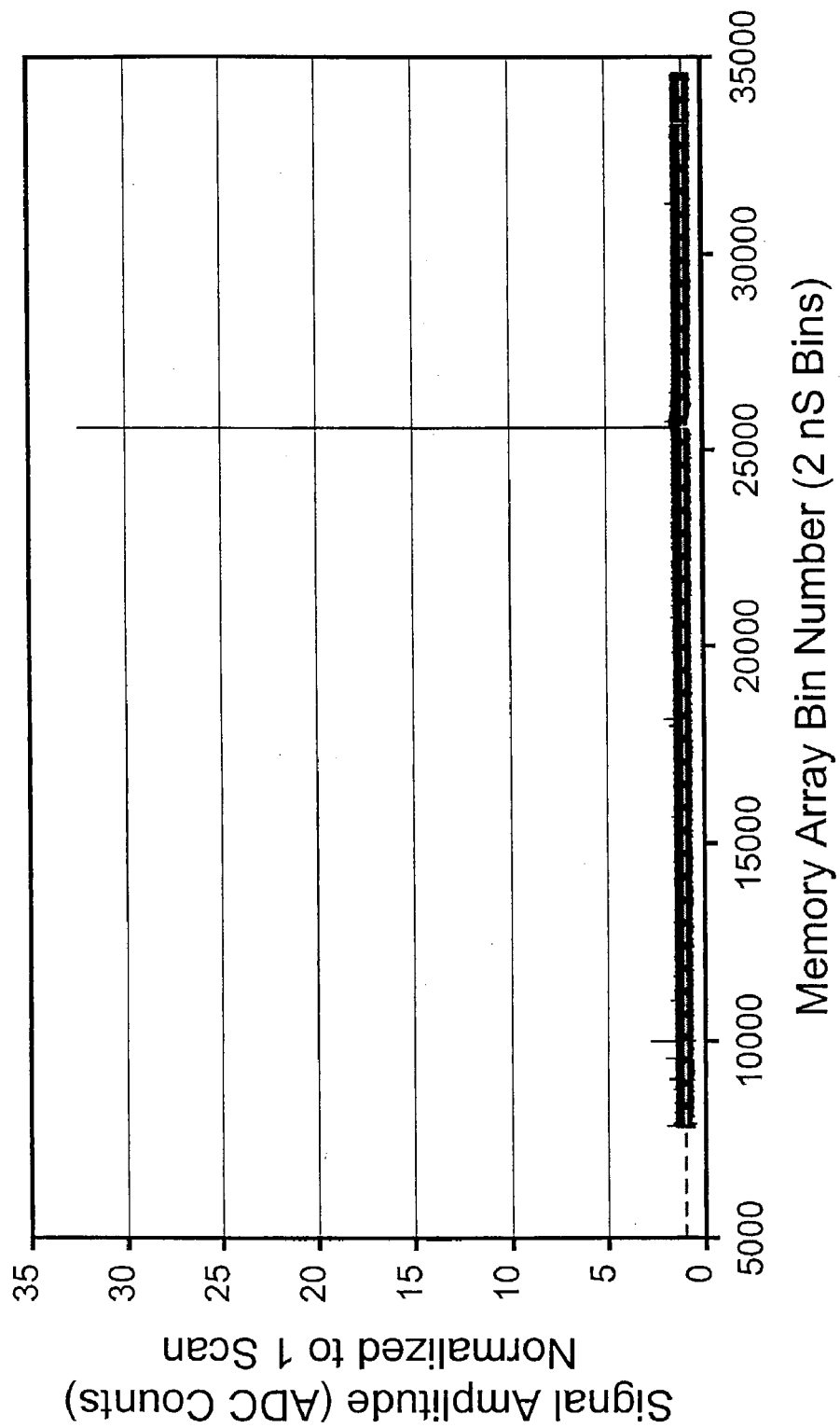
FIG. 6A illustrates a mass spectrum consisting of 625 scans of a signal waveform produced by the time-of-flight mass spectrometer and instrument configuration of FIG. 5, where the trigger delay device is programmed with a trigger delay time of 0 nanoseconds.
Figure 6B:
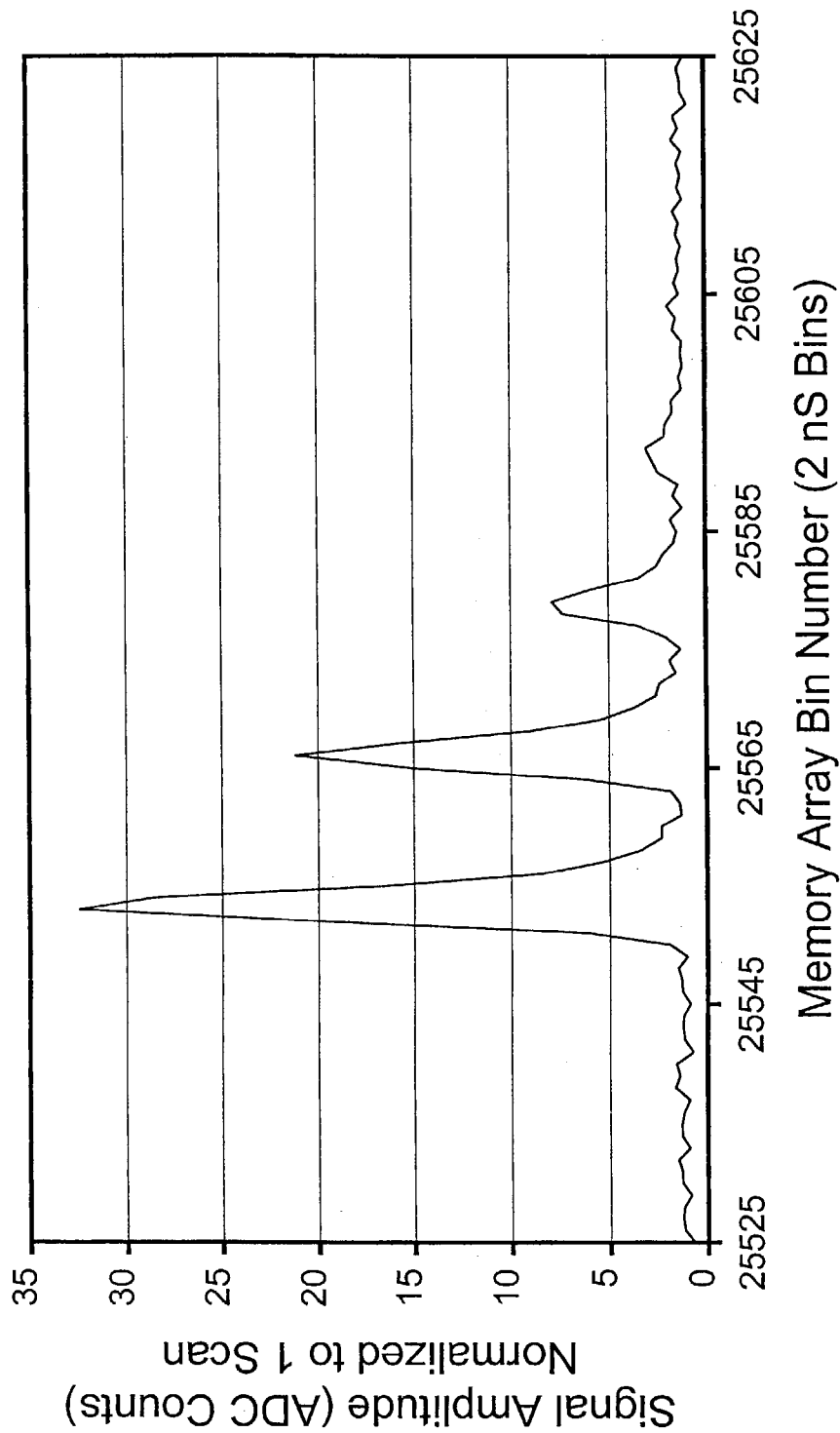
FIG. 6B illustrates an expanded view of a portion of the mass spectrum of FIG. 6A near the largest peak in the spectrum.

An illustration of the coherent noise that is characteristic of this particular DSA was presented in FIG. 3D. It is apparent from an inspection of this measurement data that this coherent noise has a repeat period that corresponds to 32 nanoseconds, or 16 ADC intervals of 2 nanoseconds each. Hence, $M_{CN}$=16 in this case, and, as discussed above, it is only necessary to increment the trigger delay time parameter, $N_{Delay}$, by 1 from 0 to ($M_{CN}$-1)=15 in order that each point on the signal waveform is measured with every value represented in this coherent noise. Consequently, a series of 16 spectra were measured, each with a different trigger delay time corresponding to an integral multiple of 2 nanoseconds from 0 to 30 nanoseconds. The spectrum corresponding to a trigger delay time of 0 nanoseconds is illustrated in FIG. 6A. It is very similar to the spectrum depicted in FIG. 2, as expected. A horizontal expansion of the region surrounding the largest peak in the spectrum is illustrated in FIG. 6B.

Figure 7A:
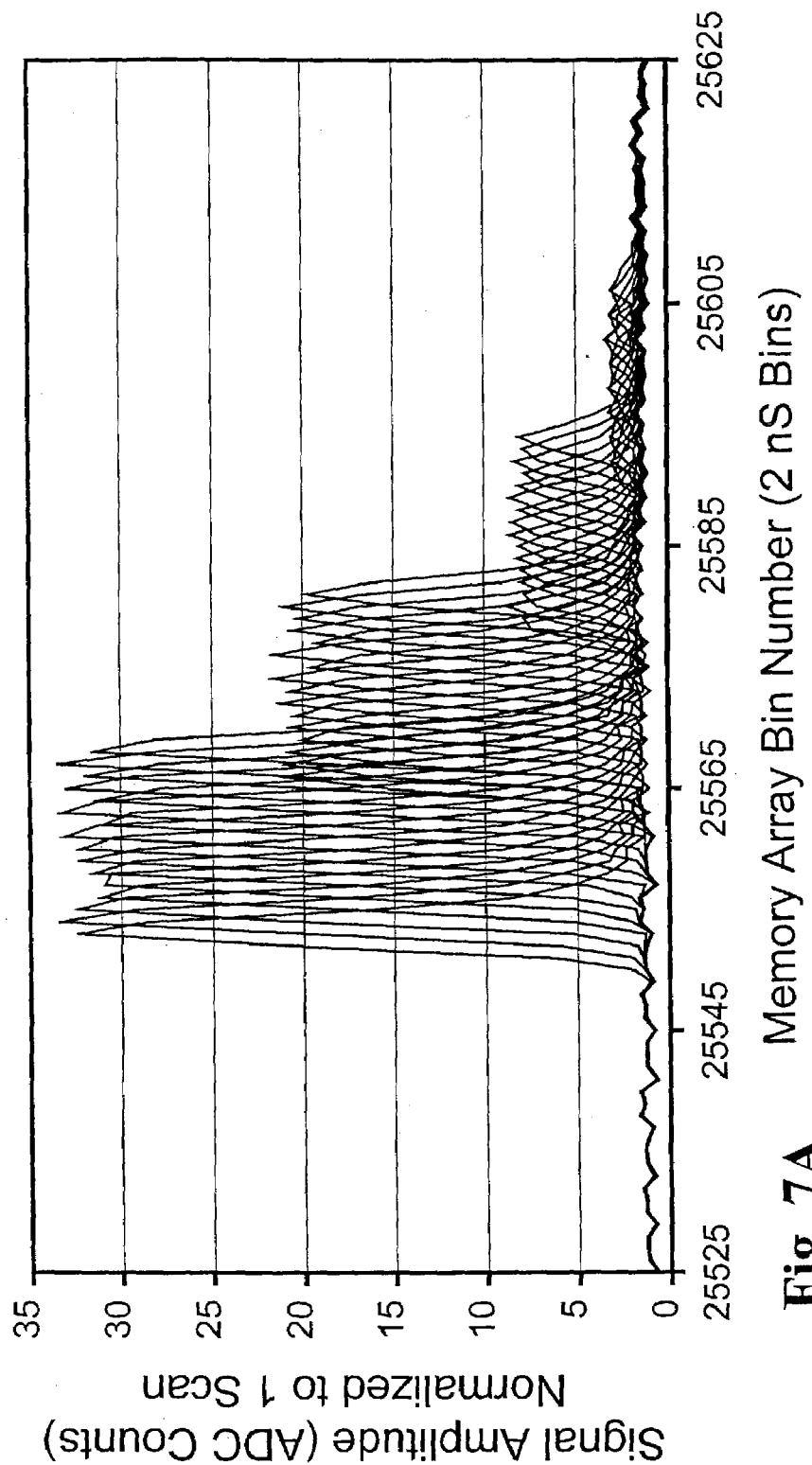
FIG. 7A illustrates an expanded view of the largest peak in the spectrum of FIG. 6 from 16 separate mass spectra, in which each spectra consists of an average of 625 scans, as in FIG. 6, but where each spectra was measured with the trigger delay device programmed with a different delay corresponding to an integral multiple of 2 nanoseconds for each spectrum, from 0 nanoseconds to 30 nanoseconds.

The 'zero' time reference of the time axis of FIG. 6 is defined as the time that the DSA generates the 'start' signal. Each of the 16 spectra were measured by the DSA and recorded relative to this same Start time, regardless of the magnitude of the time delay that the time delay device 11 adds to produce the delayed trigger. All 16 spectra are plotted on this same time axis in FIG. 7A. Each of the 16 spectra are essentially identical except that they are shifted in time, relative to the Start time of the conventional DSA, by the corresponding trigger delay time employed for each spectrum, respectively, as expected. However, it is important to note the noise pattern in the baseline is accurately reproduced from one spectrum to another, that is, the coherent noise is not shifted in time for each spectrum with respect to the DSA Start signal. This indicates that the noise, which is primarily coherent noise, is coherent, or in-phase, with respect to the Start time of the DSA, but not with respect to the signal waveform being measured.

Figure 7B:
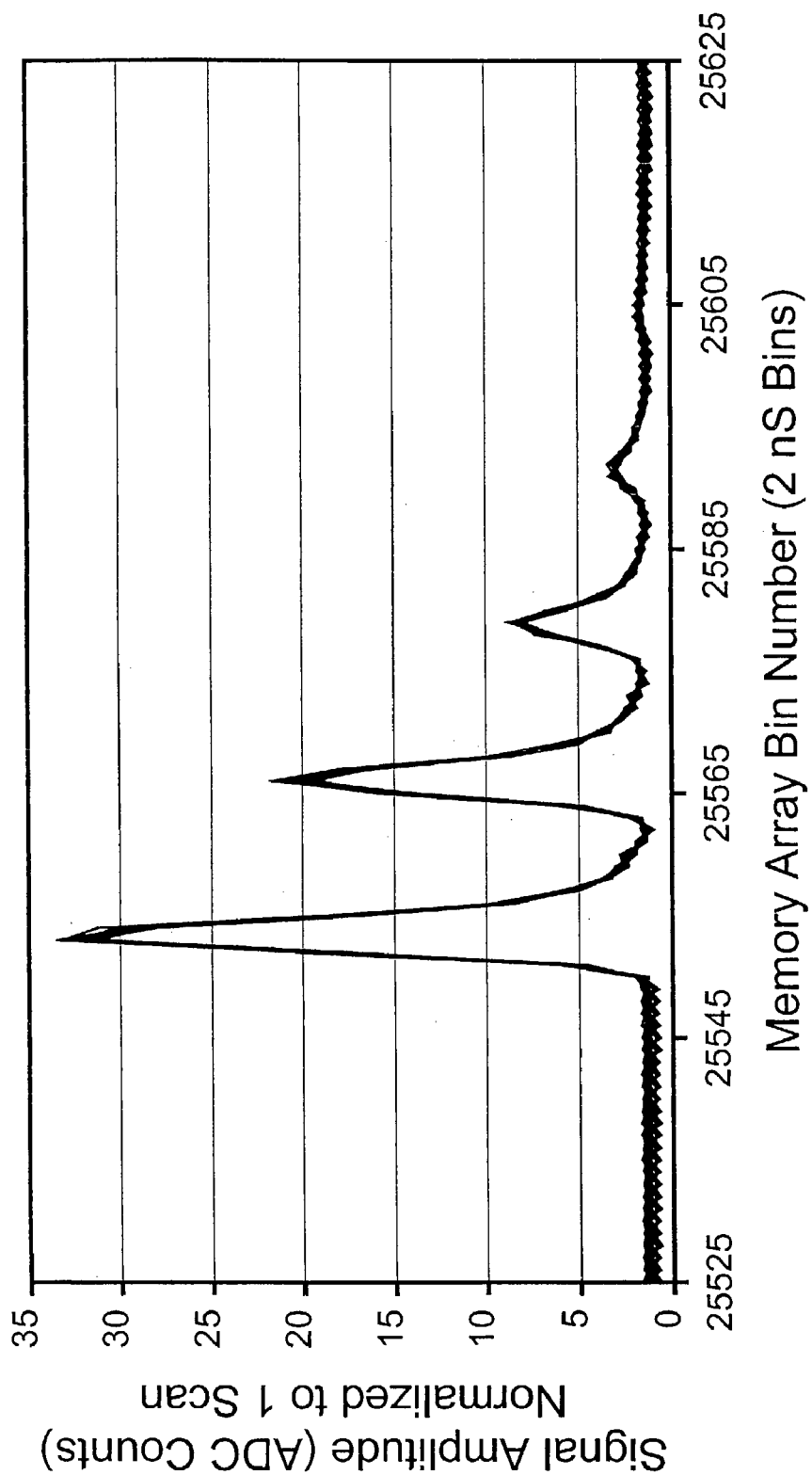
FIG. 7B illustrates the same series of mass spectra of FIG. 7A whereby each spectrum is offset on the time scale by the amount of trigger delay that was employed for each spectrum, respectively.

In order to signal average these 16 spectra according to a preferred method of the present invention, it is necessary that each point on a spectrum is averaged with the points on the other spectra that correspond to the same point in time of the spectrum waveform. This process is straightforward since the spectra are offset in time by their respective trigger delay times, which are known. By accounting for these time shifts and compensating for them, the 16 spectra may be 're-aligned' and signal averaged. The result of such 're-alignment' is illustrated in FIG. 7B, which shows the same 16 spectra after shifting them on the time axis by the amount of their respective trigger delay times. Essentially, the 'zero' time reference is now defined to be 'time zero' associated with the measurement of the signal waveform with a trigger delay time of 0, that is, the 'time zero' of the spectrum of FIG. 6, and each other spectrum is aligned with this 'time zero'. Consequently, the spectrum waveforms are now precisely lined up, or synchronized, with respect to each other, and may then be properly averaged to produce a final signal averaged spectrum. In contrast to the situation portrayed in FIG. 7A, it is important to note that the coherent noise of each spectrum as portrayed in FIG. 7B now appears to be out of phase with each other.

Figure 7C:
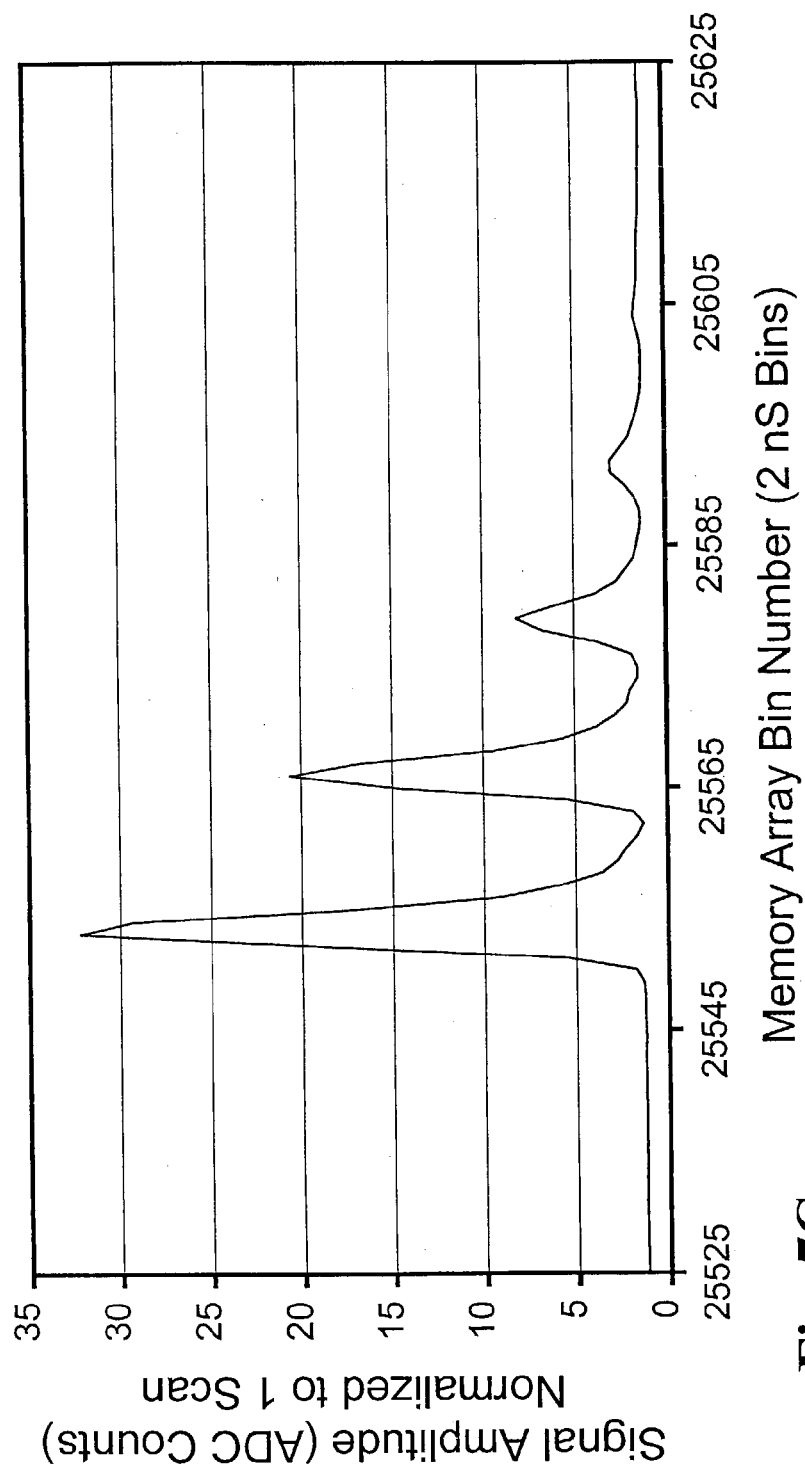
FIG. 7C illustrates the spectrum that results after averaging the 16 spectra as they are depicted in FIG. 7C, that is, after accounting for their respective trigger delay offsets.

The final signal averaged spectrum that results from averaging the 're-aligned' spectra of FIG. 7B is shown in FIG. 7C. This final average spectrum, then, consists of 16×625=10,000 scans of the signal waveform. The coherent noise has been substantially reduced. The region of the spectrum, which was portrayed above in FIG. 3 as being characteristic of the noise, is shown for the spectrum of FIG. 7C in FIG. 7D. The measurements of FIG. 3 and FIG. 7 both represent a signal averaged spectrum of 10,000 scans. However, by signal averaging the 10,000 scans according to the devices and methods of the present invention, as illustrated in FIG. 7D, the coherent noise has clearly been substantially reduced relative to that achieved by conventional signal averaging devices and methods, as represented in FIG. 3D.

Figure 7D:
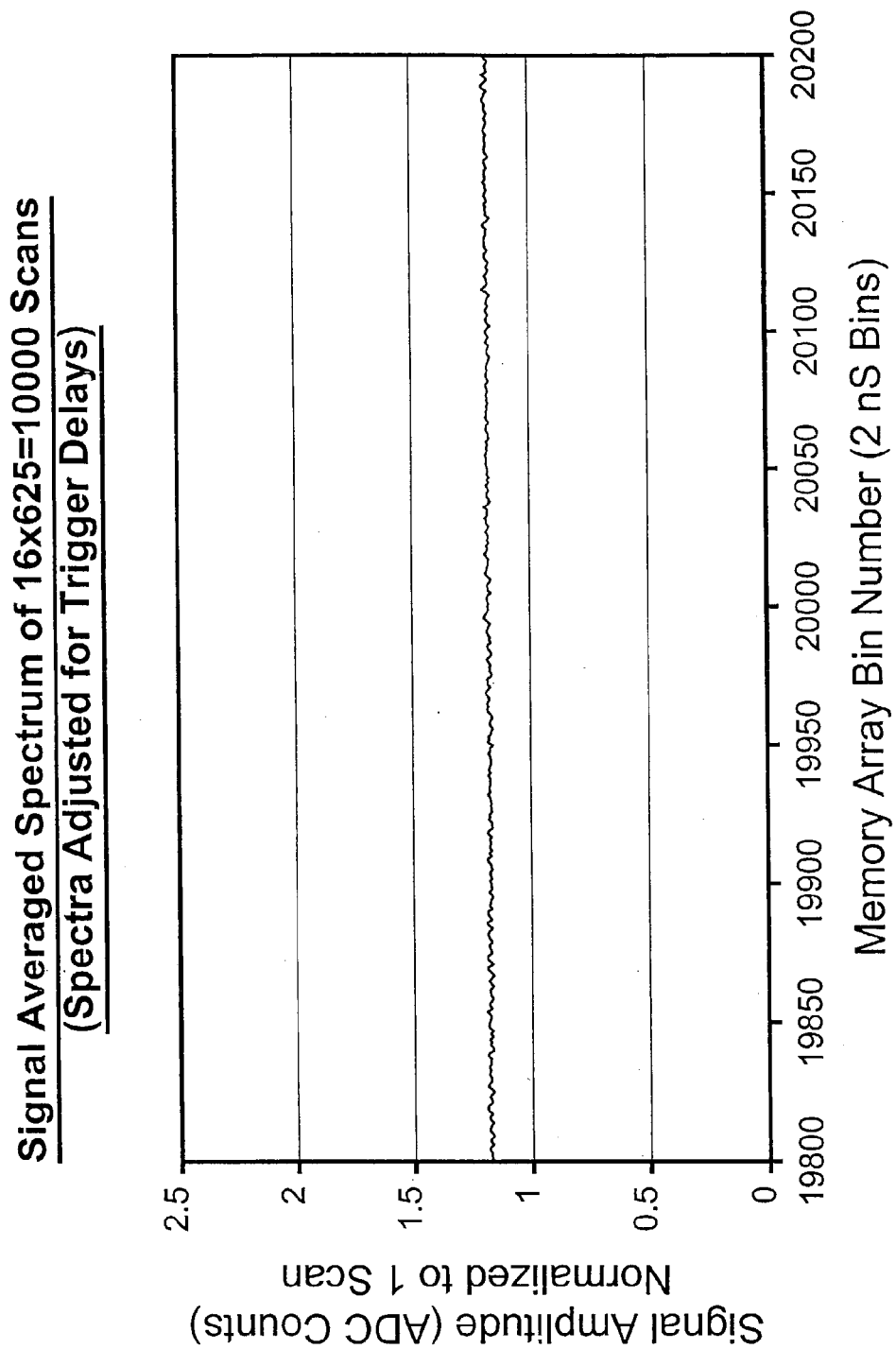
FIG. 7D is an expanded portion of the spectrum illustrated in FIG. 7C corresponding to the region of the spectrum depicted in FIG. 3D, for comparison.
Figure 7E:
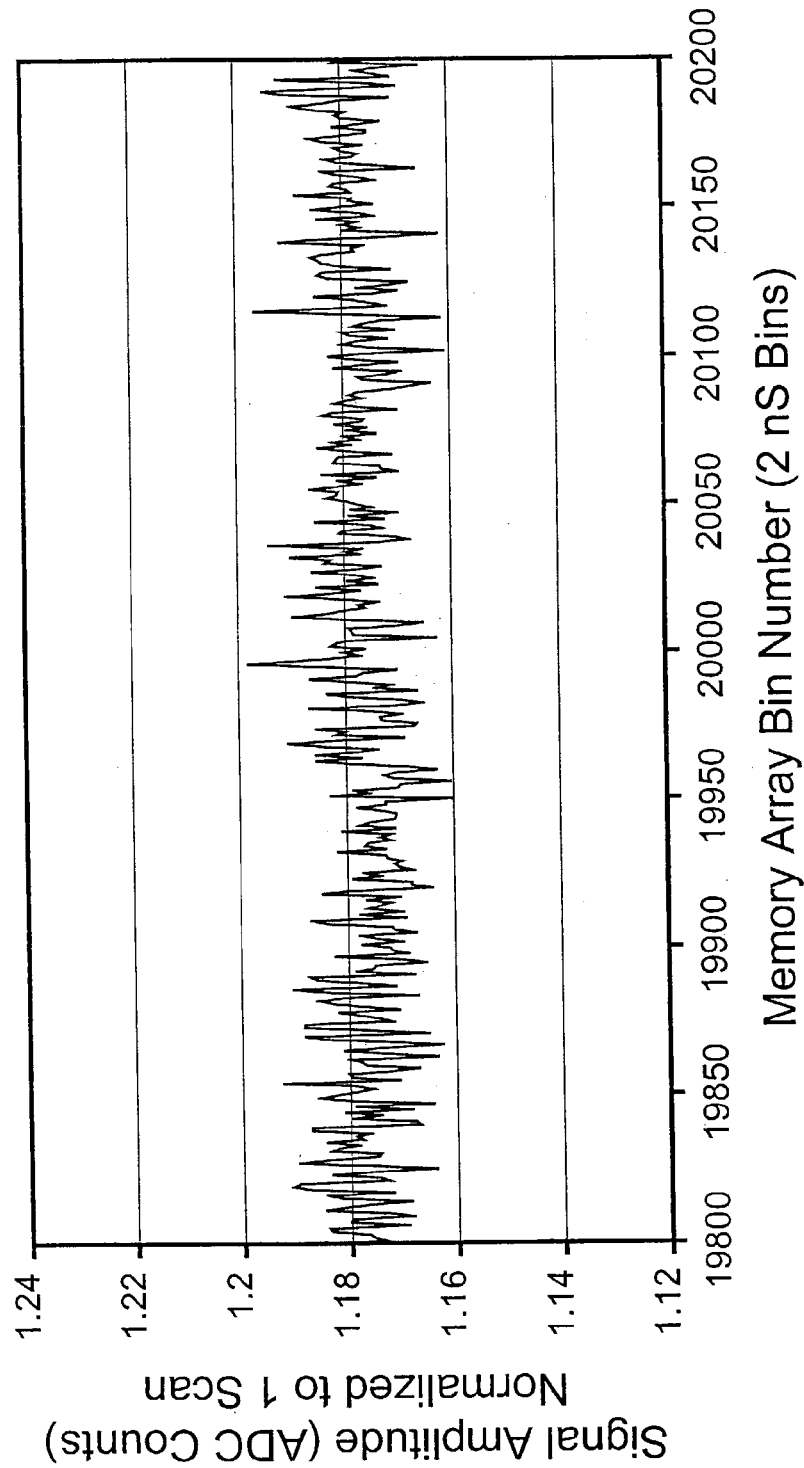
FIG. 7E illustrates the portion of the spectrum presented in FIG. 7D with a vertical scale expanded by a factor of 20 for better visualization.

An expanded view of the noise in FIG. 7D is illustrated in FIG. 7E. Based on the more or less random appearance of the noise, it would seem that the coherent noise has actually been reduced in this demonstration of the devices and methods of the present invention to the extent that the random noise that remains after averaging 10,000 scans becomes dominant. Quantitatively, the devices and methods of the present invention have reduced the RMS value of the noise that remained after conventional signal averaging, as illustrated in FIG. 3D, by a factor of about 40 in this demonstration.

Notwithstanding the dramatic reduction of coherent noise demonstrated above with the devices and methods of the present invention, it may, nevertheless, often be even more advantageous or otherwise desirable to combine the methods and devices of the present invention with one or more conventional approaches to reducing coherent noise. For example, a common conventional approach to minimizing the apparent presence and impact of coherent noise is to incorporate a zero-level offset so that, as discussed above, for regions of the measured signal waveform where the signal amplitude is sufficiently small relative to the ADC digitization increments, the coherent noise amplitude is never, or seldom, large enough to rise above the amplitude level corresponding to 1 LSB of the ADC. This situation may be achieved, for example, if the maximum amplitude of the coherent noise, per scan, is less than the amplitude level of 1 LSB, which is the case for the DSA that was used for the measurements reported herein, and the zero level offset is adjusted to correspond to an ADC amplitude level of 0. Under these conditions, the measurements of FIGS. 3 and 7 were repeated, that is, with the zero level offset adjusted so that the 0 amplitude level of the spectra coincided with the 0 LSB level of the ADC, rather than 1 LSB level, as for the measurements of FIGS. 3 and 7.

Figure 8A:
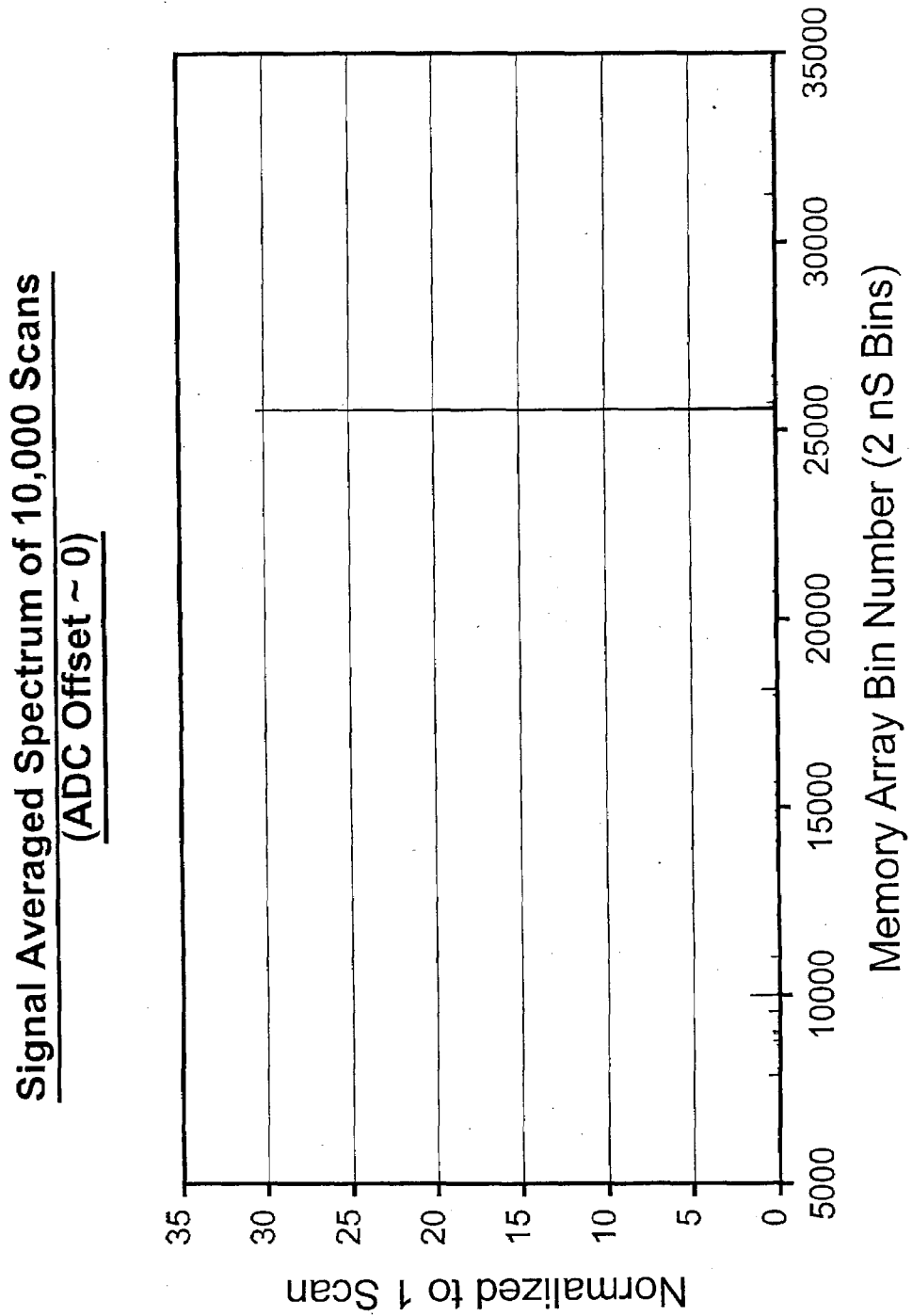
FIG. 8A illustrates a mass spectrum consisting of 10,000 scans of a signal waveform produced by the time-of-flight mass spectrometer and instrument configuration of FIG. 5, where the trigger delay device is programmed with a trigger delay time of 0 nanoseconds in order to represent the measurement characteristics of a conventional signal averaging approach, as in FIG. 6A, but with a signal offset corresponding to 0 on the ADC count scale.
Figure 8B:
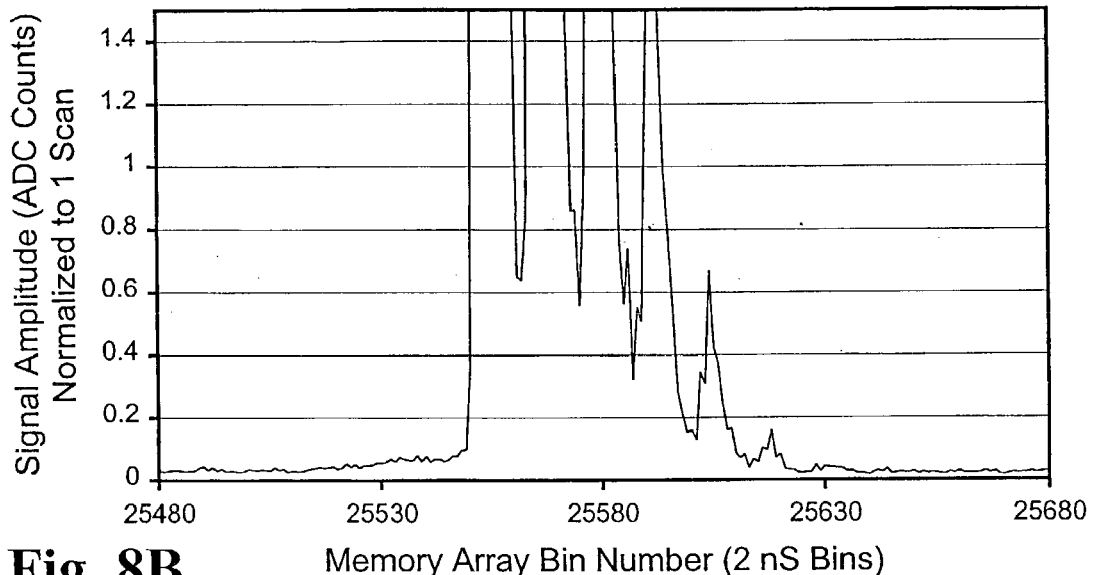
FIG. 8B illustrates an expanded view of a portion of the mass spectrum of FIG. 8A near the largest peak in the spectrum.
Figure 8C:
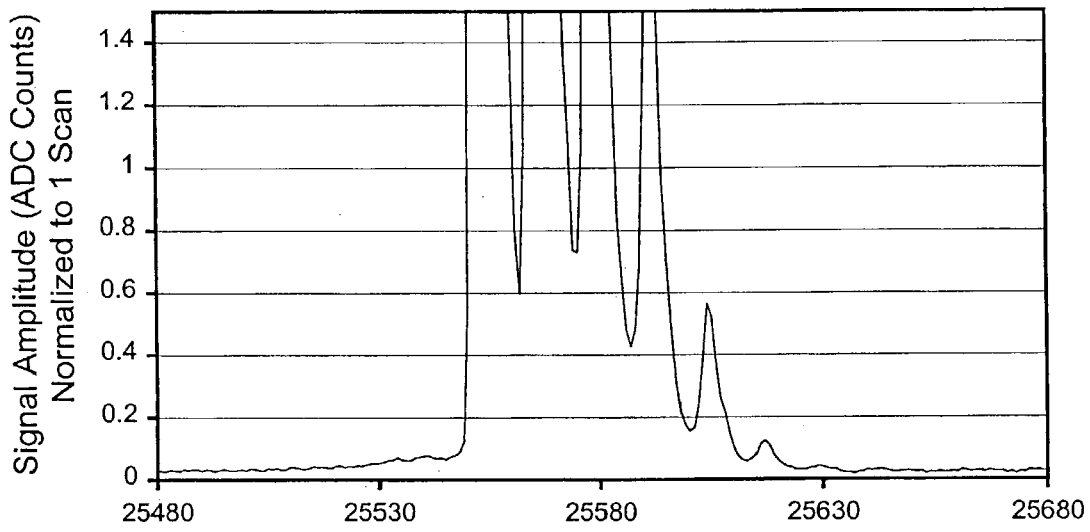
FIG. 8C illustrates an expanded view of the largest peak in a spectrum of the same sample that was used for the measurement of FIG. 8A, but which was measured according to the devices and methods of the present invention in the same manner as the measurements of FIGS. 6 and 7.

A spectrum of 10,000 scans, signal averaged according to conventional averaging methods, and where the zero level offset is adjusted to 0 LSB, is illustrated in FIG. 8A. An expanded portion of this spectrum near the largest peak is shown in FIG. 8B. The same spectrum was then measured, again with a zero level offset corresponding to 0 LSB, but where the signal waveform was measured, and the signal averaging was performed, in the same manner as described above for the spectrum of FIG. 7, that is, in accordance with the devices and methods of the present invention. The portion of the resulting spectrum near the largest peak is shown in FIG. 8C. A comparison of the spectrum of FIG. 8C with that of FIG. 8B demonstrates that the noise in the spectrum is significantly less by employing the devices and methods of the present invention in conjunction with the conventional method of a zero level offset, compared to the noise reduction that can be achieved by employing the conventional zero level offset adjustment and conventional signal averaging methods alone.

In the above demonstration, the repeat period of 32 nanoseconds in the pattern of coherent noise is characteristic of the specific DSA that was used, which was the EG&G FastFlight DSA. Other DSA's may be expected to exhibit different coherent noise characteristics, so that the number of trigger delay times that may be optimum in accordance with the devices and methods of the present invention may be different for other DSA's, in general, from that used in the above example.

While the above measurements and signal averaging procedures demonstrate the fundamental and essential aspects of the present invention, more preferred embodiments of the present invention may be envisioned, for example, in which the functionality of the trigger delay device is implemented into the electronic structure of the timing device of the DSA. Such an integrated implementation also facilitates the automation of the measurement and signal averaging processes according to the present invention. However, in the discussions herein, the functionality of the trigger delay device will be portrayed as a separate block in the illustrated configurations for the sake of clarity.

While the optimum design details may vary depending on the specific electronic architecture and components employed (which therefore may generate different patterns of coherent noise), a specific design may be envisioned, for the sake of definiteness and illustration, which exemplifies the important features of any such implementation of the methods and devices of the present invention. Specifically, modifications to the design of a conventional, commercially available DSA, the EG&G FastFlight, which was employed for the measurements presented above, are described below which represent a particular implementation of the devices and methods of the present invention.

An important aspect to the design of a DSA that incorporates devices and methods of the present invention is that the trigger delay device, the memory array, and signal averaging processor must be synchronized such that real time digital signal averaging of spectra takes proper account of the relative time shifts that occur from one scan to another due to different trigger delay times. This coordination is most beneficial when it is accomplished with minimal changes to the pattern of data transfer, read, add, and write processes, that is, the repetitive sequence of digital operations in the DSA that give rise to a repetitive coherent noise pattern, as spectra are signal averaged.

The relevant aspects of the internal architecture of the EG&G FastFlight DSA are described by Peck, et. al., in U.S. Pat. No. 6,094,627, and by Gedcke, et. al., in U.S. Pat. No. 6,028,543, both of which are incorporated herein by reference. Essentially, in order to achieve a high speed DSA by combining a high speed ADC with a slower memory array, the memory array is configured as two complete and separate memory arrays, where each separate memory array is composed of 8 memory array devices, or chips. The process of signal averaging, or, more precisely, summing, a new data value provided by the ADC with previous summation of data values requires a processor to perform the following operations: read the previous summed data value from the appropriate memory element; add the new data value to the sum; and then write the new summed data value back to the appropriate memory element. While the ADC produces a new data value every 2 nanoseconds, the memory array devices that are used in the EG&G FastFlight have a read or write access time of 16 nanoseconds. That is, up to 16 nanoseconds may be required to read a data value in a memory storage element, and up to 16 nanoseconds may be required to write a data value to a memory storage element. Therefore, without including the time required to perform an 'add' operation in the processor, a read-add-write cycle may require up to 32 ns to complete, which is much longer time period than the time between ADC intervals of 2 nanoseconds.

In order to overcome this bandwidth mismatch, consecutive memory array elements are staggered among a battery of 8 memory chips, so that each of 8 consecutive data values produced by the ADC are associated with a memory array storage element on a different memory array device. The next consecutive 8 data values produced by the ADC repeat this cycle, and so on. Therefore, each memory device is accessed only every $8^{th}$ ADC data value, accounting for 16 nanoseconds of a 32 nanosecond read-add-write summation process. The 16-nanosecond period allows time for the first memory array device element to be read, but not for the new sum data value to be written to this device before the device needs to be read again in order to process the data value that is produced 8 ADC intervals, or 16 nanoseconds, later. Therefore, each new sum data value is written instead to another memory array device of a second group of 8 memory array devices, which is a duplicate of the first group of 8 memory array devices. This second group of 8 memory devices may be referred to as the 'B' group, while the first group of 8 memory devices may be referred to as the 'A' group. This process continues until the current scan is complete. The next scan, then, reads the sum data values from the elements of the 'B' group of 8 memory array devices, and writes new sum data values to the 'A' group of 8 memory array devices. This 'ping-pong' read-add-write process continues until the required number of scans has been measured and summed.

It is believed that the 32-nanosecond read-add-write cycle of this particular DSA is primarily responsible for generating the pattern of coherent noise that is exhibited in the measurements reported herein. Further, it would appear that the coherent noise pattern is produced as a result of addressing the 8 memory devices, regardless of the particular memory element that is being addressed within any one memory device; otherwise, the pattern of coherent noise would not be repetitive, at least with a repeat period as short as 32 nanoseconds. However, it is not certain at the present time whether the same pattern of coherent noise is generated when the 'A' group of memory devices is read from, and the 'B' group of memory devices is written to, as when the 'B' group of memory devices is read from, and the 'A' group of memory devices is written to. The reason for this uncertainty is that each spectrum measured with the current apparatus using the same trigger delay offset consists of a signal averaged measurement of a number of scans, where the read-add-write cycle alternates with each scan between reading from 'A' memory group and writing to the 'B' memory group, and reading from the 'B' group and writing to the 'A' group. Therefore, the summed coherent noise of the composite summed spectrum might conceivably consist of the summation of two different coherent noise patterns: one coherent noise pattern which may be generated by the cycle of reading from the 'A' group and writing to the 'B' group during every other scan; while a different coherent noise pattern may be generated by the cycle of reading from the 'B' group and writing to the 'A' group during the remaining alternate scans.

Figure 9A:
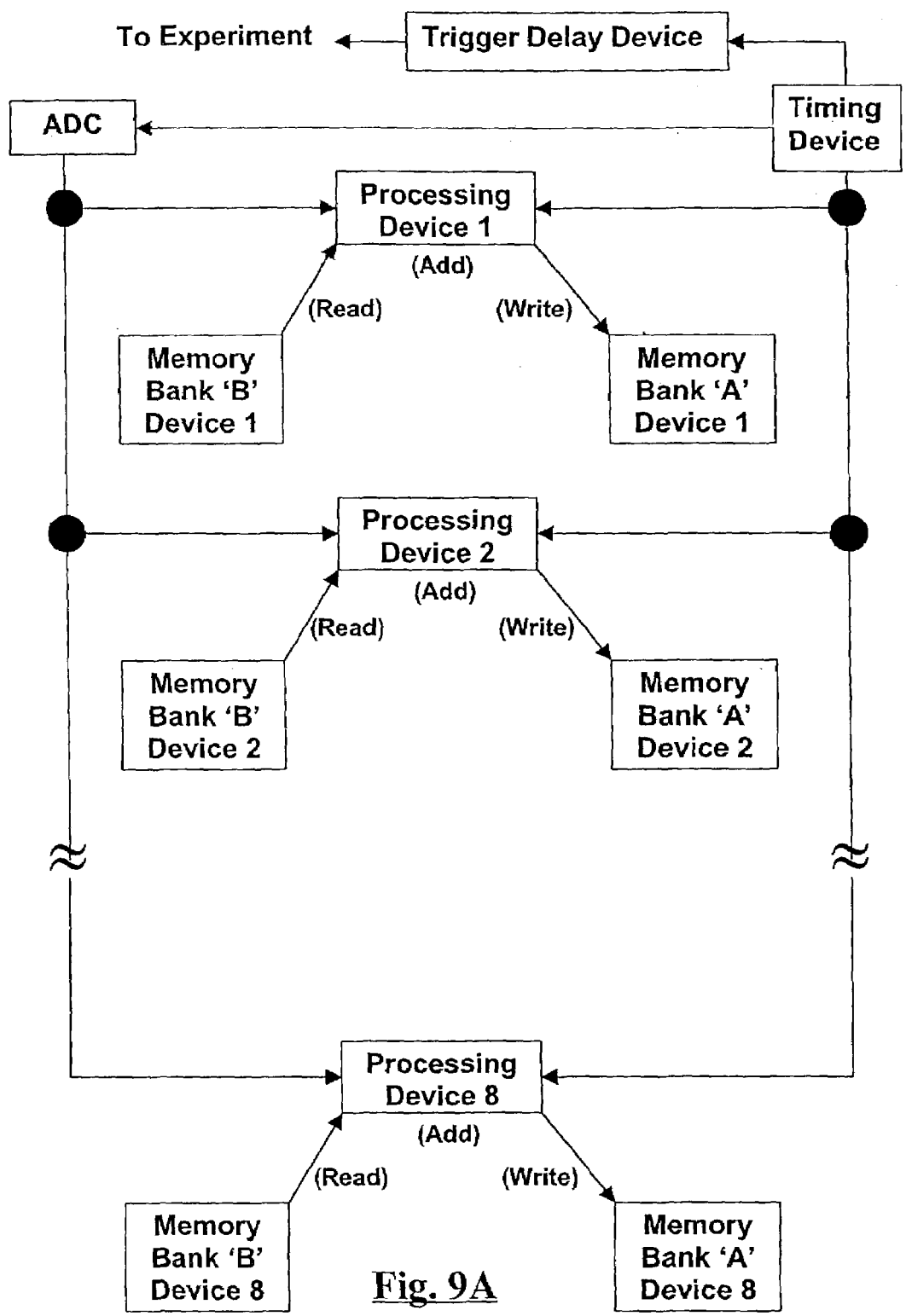
FIG. 9A illustrates a schematic diagram of a DSA showing the parallel-processing memory architecture and the flow of data during a first scan in which previous sum data is read from a first memory array bank, and new sum data is written to a second memory array bank, according to one preferred aspect of the present invention.
Figure 9B:
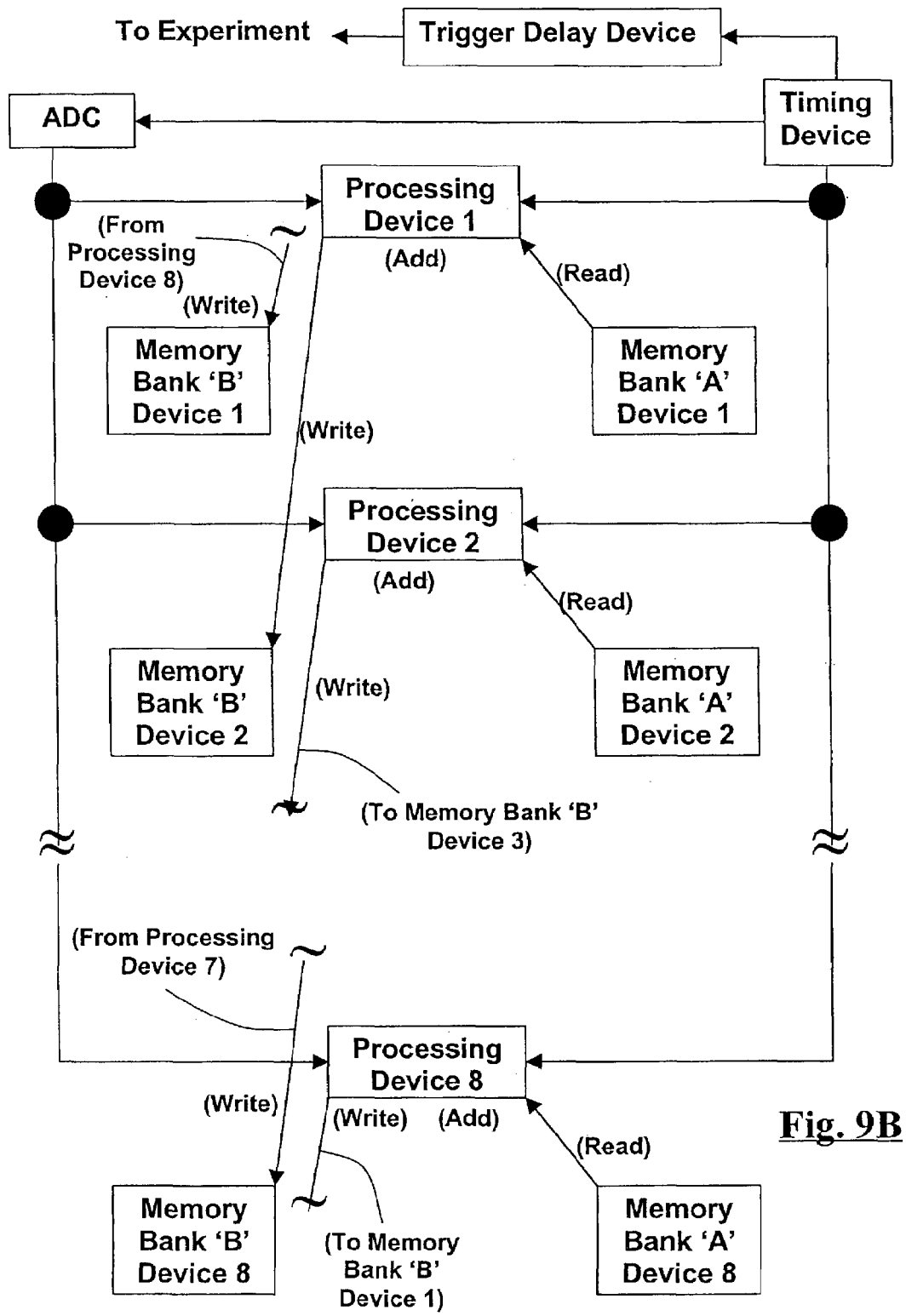
FIG. 9B illustrates a schematic diagram of a DSA showing the parallel-processing memory architecture and the flow of data during a second scan in which previous sum data is read from the second memory array bank of FIG. 9A, and new sum data is written to the first memory array bank of FIG. 9A, according to one preferred aspect of the present invention.

An example of lone implementation of the present invention, then, involves design modifications of the EG&G FastFlight DSA that embodies the essential aspects of the devices and methods of the present invention, that is, the addition of a trigger delay device, and a signal averaging scheme that compensates for the trigger delay of a scan concurrent with the signal averaging process. The objective of the design modifications in accordance with the devices and methods of the present invention is to ensure that each point on the signal waveform is measured in conjunction with each possible value exhibited in the coherent noise pattern during the signal averaging process. A conceptual representation of one possible configuration and mode of operation that accomplishes this objective is illustrated in FIGS. 9 and 10. FIGS. 9A and 9B illustrates a simplified block diagram of the signal averaging architecture, which is similar to that of the EG&G FastFlight DSA, after Peck, et. al., in U.S. Pat. No. 6,094,627. The essential components of the architecture include two banks of 8 memory devices each, the 'A' bank and the 'B' bank, and 8 processors, all of which are interfaced to the ADC and the timing device. FIG. 9A illustrates that, for every other scan, the read-add-write sequence of operations that is performed for each ADC value of each of every other scan proceeds by reading previous sum data from the memory devices of Memory Bank 'B', adding the new ADC values of the current scan in the Processing Devices, and writing the resulting new sum data to the memory devices of Memory Bank 'A'. FIG. 9B illustrates the sequence of operations for the other alternate scans, in which the sum data from the memory devices of Memory Bank 'A' are read, the new ADC values of the current scan are added to these sum data in the Processing Devices, and the resulting new sum data are written to the memory devices of Memory Bank 'A'. However, in contrast to the sequence of operations for the first set of alternate scans illustrated in FIG. 9A, the sequence of operations as illustrated in FIG. 9B for the second set of alternate scans involves writing the resulting sum data to memory devices of Memory Bank 'B' in an order that is different from that with which the previous sum data was read from the memory devices of Memory Bank 'A'. The rational and consequences of this difference will become clear from the discussion that follows.

A timing diagram that demonstrates a method of operating the architecture of FIG. 9 is provided in FIG. 10. The signal averaging process according to this embodiment of the present invention proceeds as follows: Initially, all memory elements are initialized to zero, or at least the memory elements of memory bank 'B', device #1. Then, the first scan is initiated when the Start signal is generated by the timing device, indicated on the timing diagram of FIG. 10A as "Start Scan #1 Out". For the first scan, the trigger delay is programmed to be 0 nanoseconds, so that the trigger to the experiment occurs simultaneously with the 'Start' signal. At some time later (4 ADC intervals in FIG. 10A, but this response time will depend on the details of the experiment that generates the signal waveform), the first point of interest of the signal waveform arrives at the ADC input, and the ADC generates ADC Data #1. At this point in time, Processing Device #1 reads the contents of Memory Bank 'B', Device #1, Element #3, and adds this value (which is 0 for this first scan) to the ADC Data #1 value. These read and add processes are expected to take about 16 nanoseconds, or 8 ADC intervals. The Processing Device #1 then writes the sum data value to Memory Bank 'A', Device #1, Element #1. This write process takes about another 16 nanoseconds. Meanwhile, 2 nanoseconds (1 ADC interval) after ADC Data #1 was generated, the second ADC value, ADC Data #2, is generated. At this point in time, Processing Device #2 reads the contents of Memory Bank 'B', Device #2, Element #3, adds this value (which is 0 for this first scan) to the ADC Data #2 value, and writes the sum to Memory Bank 'A', Device #2, Element #1. This sequence continues for ADC Data #3 through ADC Data #8, involving Processing Devices #3 through #8; Memory Bank 'B', Device #3, Element #3 through Device #8, Element #3; and Memory Bank 'A', Device #3, Element #1 through Device #8, Element #1, in a similar fashion, as illustrated in FIGS. 9A and 10A.

Figure 10A:
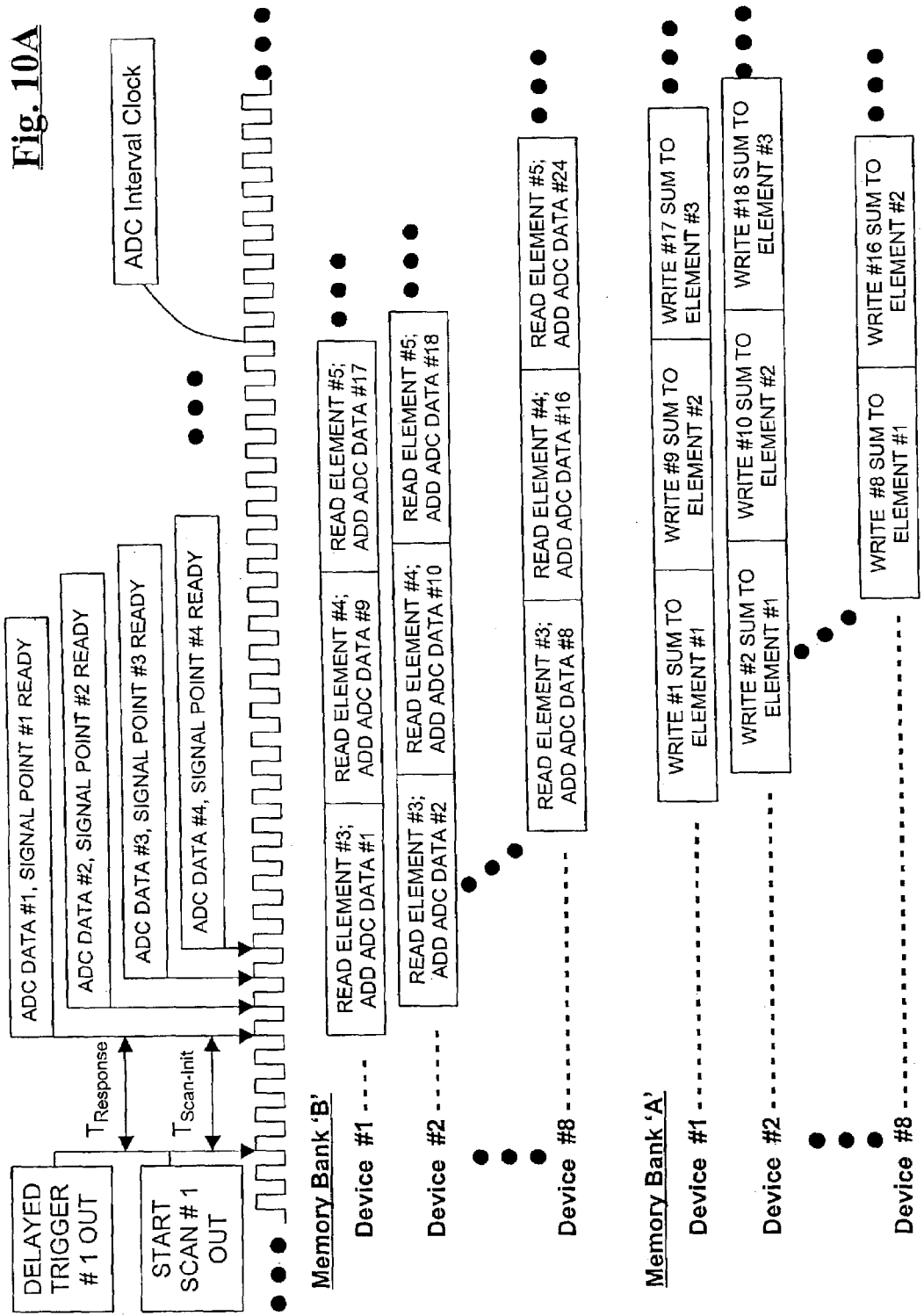
FIG. 10A illustrates a timing diagram associated with one preferred method of operating a particular embodiment of a DSA of the present invention, for the first scan of a signal averaging measurement.

By the time that ADC Data #9 is generated, 16 nanoseconds has past since the last read operation was performed on Memory Bank 'B', Device #1, and this device is again ready to perform a second read operation, specifically of the contents of the next sequential memory location, Element #4, in order to add this value with the ADC Data #9 value. This process continues for each new ADC Data value until the first scan is complete, as illustrated in FIGS. 9A and 10A.

Figure 10B:
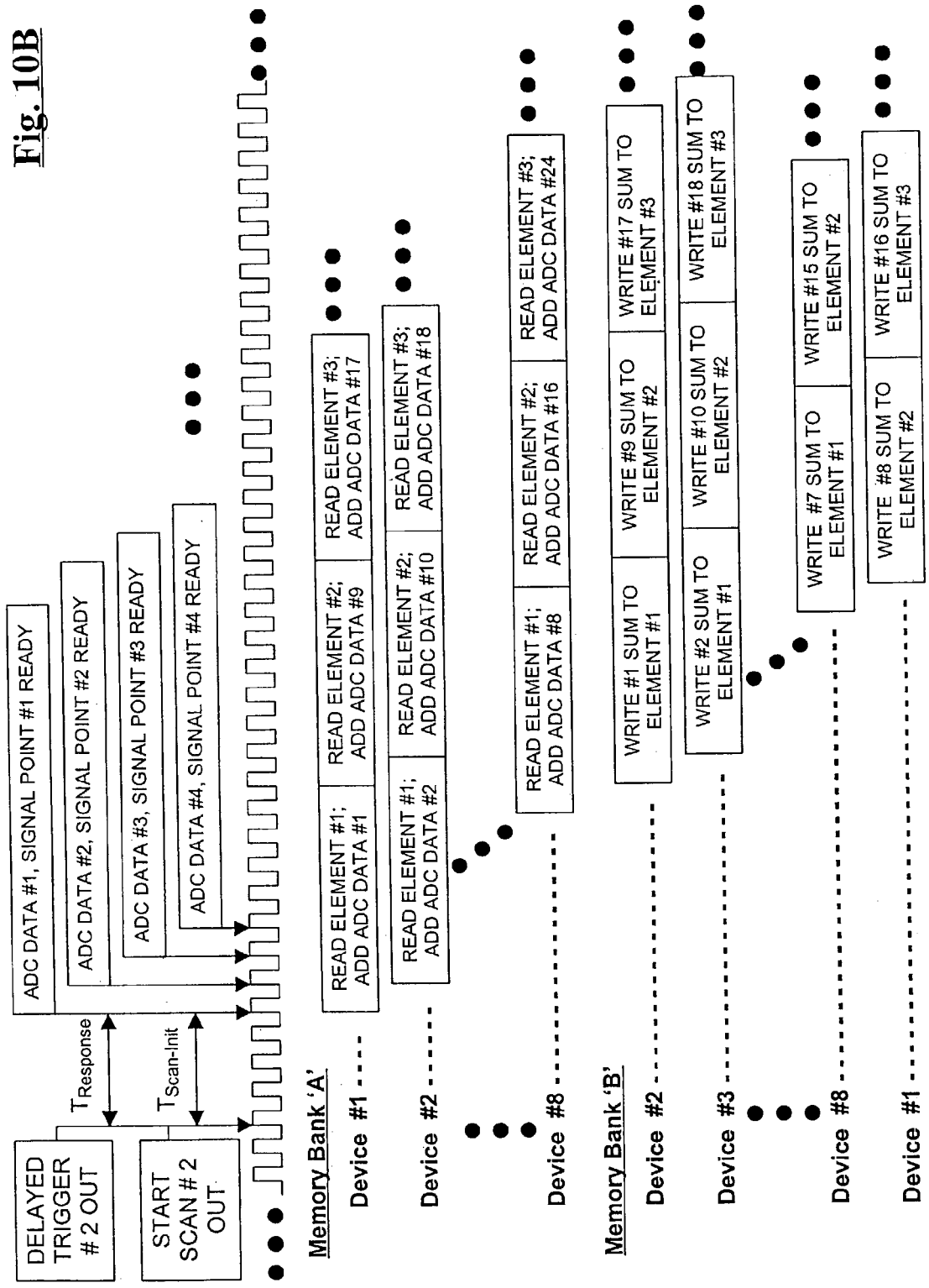
FIG. 10B illustrates a timing diagram associated with one preferred method of operating a particular embodiment of a DSA of the present invention, for the second scan of a signal averaging measurement.

After the first scan is completed, the second scan commences. For this second scan, as illustrated in FIGS. 9B and 10B, a Start signal is generated by the timing device, the trigger delay device is programmed with 0 trigger delay, which generates a trigger signal to the experiment that is simultaneous with the Start signal, and the experiment produces a signal waveform that is a replica, more or less, of the first signal waveform. However, in contrast to the order of operations described above for the first scan, for this second scan, the Memory Devices 'A' are read from, the new ADC Data values are added to these contents, and the sums are written to the Memory Devices 'B'. When ADC Data #1 is generated, the data value in Memory Bank 'A', Device #1, Element #1 is read, and added to ADC Data #1 in Processing Device #1. The resulting sum is written to Memory Bank 'B', Device #2, Element #1. Note that the sum is written to Memory Device #2 of Memory Bank 'B', while the stored data value that was added to the ADC Data #1 resided in Memory Device #1 of Memory Bank 'A'. This process continues, as illustrated in FIGS. 9B and 10B, for subsequent ADC Data values, until, when ADC Data #8 is generated, this data is added to the contents of Memory Bank 'A', Device #8, Element #1, and the resulting sum is written to Memory Bank 'B', Device #1, Element #2. The ninth ADC value, ADC Data #9, is added to the contents of Memory Bank 'A', Device #1, Element #2, and the resulting sum is written to Memory Bank 'B', Device #2, Element #2, and so on. In other words, for this second scan, each new summed data value is always written to the memory element that would have been written to, according to the sequence of the first scan, during the processing of the next ADC Data value, rather than the current ADC Data value. Therefore, the summed signal waveform data is re-aligned, at the end of this second scan, with the memory array elements to correspond with a shift of the data by one ADC interval later.

Figure 10C:
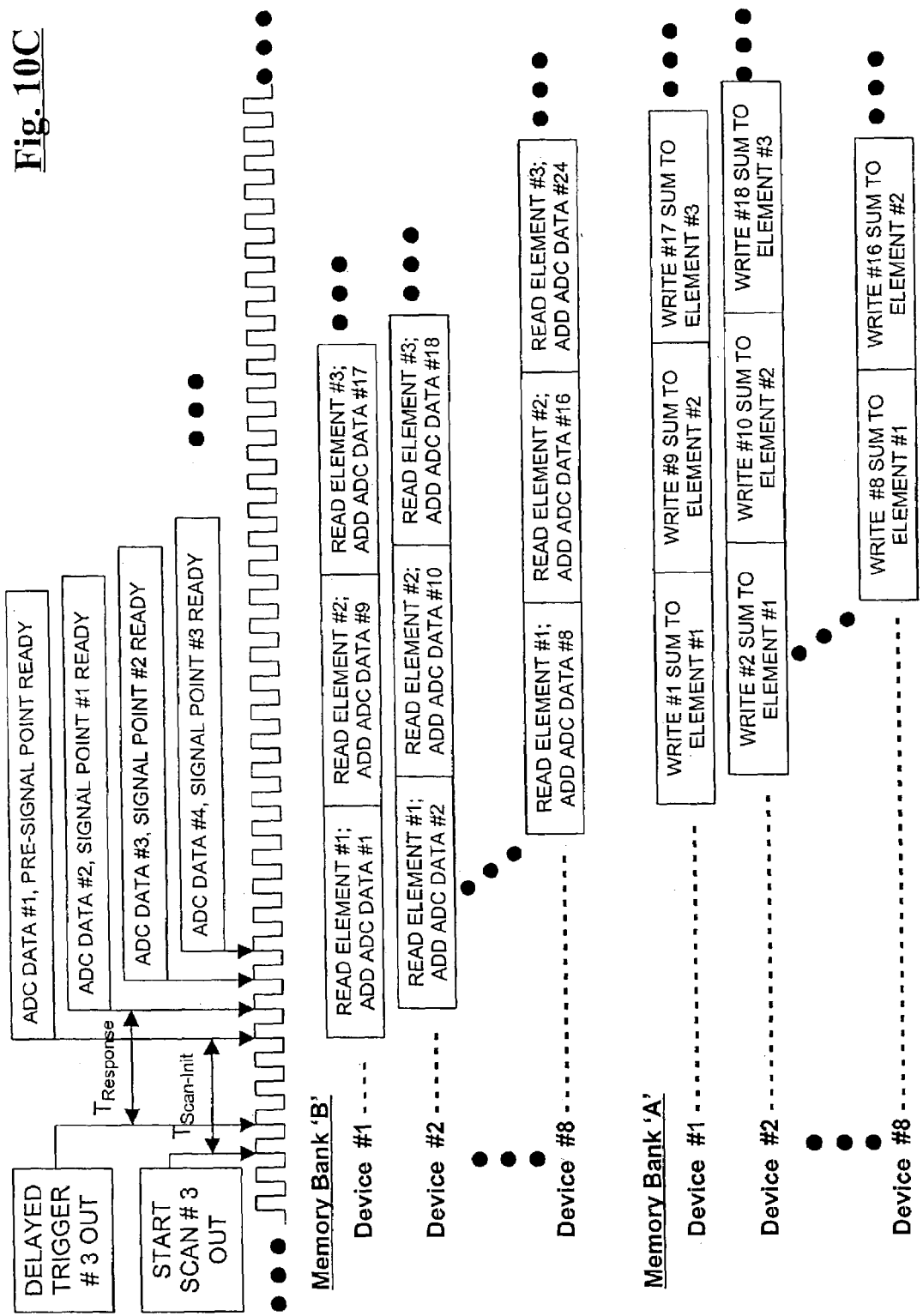
FIG. 10C illustrates a timing diagram associated with one preferred method of operating a particular embodiment of a DSA of the present invention, for the third scan of a signal averaging measurement.

The timing sequence for the third scan is portrayed in FIG. 10C. This sequence is similar to that of the first scan, with two major differences: first, a trigger delay of 1 ADC interval (2 nanoseconds) is programmed into the trigger delay device, rather than 0 as for the first scan; and second, the sequence of read operations from the Memory Bank 'B' devices begins with Element #1 for each memory device, in contrast to the first scan, which began the read operations with Element #3 from each memory device. The reason for this (that is, for the fact that Element #3 was the element written to during the first and second scans, while Element #1 is the element written to for the subsequent 30 scans) will become clear from the discussion below. The trigger delay of 1 ADC interval results in the signal waveform being delayed by 1 ADC interval relative to the Start signal, while the processing of the ADC data values begins at the same point in time relative to the Start signal, which time is designated $T_{Scan-Init}$, as for all other scans. This means that the signal waveform is now properly aligned with the previously shifted summed signal waveform data, allowing a proper summation of new data with previous sum data using the sequence of read, add, and write operations illustrated in FIG. 10C.

For the fourth scan, a trigger delay of 1 ADC interval is maintained, and the sequence of operations is identical to that portrayed for the second scan in FIG. 10B. This sequence is reproduced in FIG. 10D, the only difference from the second scan in FIG. 10B being that the trigger delay time is 1 ADC interval in FIG. 10D, in contrast to a trigger delay of 0 ADC intervals in FIG. 10B. In both FIGS. 10C and 10D, the trigger delay of 1 ADC interval shifts the signal waveform by 1 ADC interval later with respect to the time at which the first ADC Data #1 value is generated. Hence, this first ADC Data #1 value is ultimately ignored; this data value is designated as a "Pre-Signal Point" in FIGS. 10C and 10D.

The processes described above for Scan #3 and Scan #4 are repeated for subsequent pairs of scans, where the trigger delay is programmed to be 1 more ADC interval for each subsequent pair of scans. This process continues until 16 different trigger delay times have been employed, from a trigger delay of 0 for Scan #1 and Scan #2, to a trigger delay of 15 ADC intervals for Scan #31 and Scan #32. Again, the reason that two consecutive scans are summed in this fashion with the same trigger delay offset is to ensure that, if two different coherent noise patterns are present, one from the sequence of reading from the Memory Bank 'A' and writing to the Memory Bank 'B' during even (or odd) numbered scans, and other from reading from Memory Bank 'B' and writing to Memory Bank 'A' during odd (or even) numbered scans, both coherent noise patterns will be included in the coherent noise averaging process. Because two scans were measured for each different trigger delay value, the complete process requires 32 scans to measure each signal waveform point in the presence of all possible contributions of the coherent noise pattern.

Figure 10D:
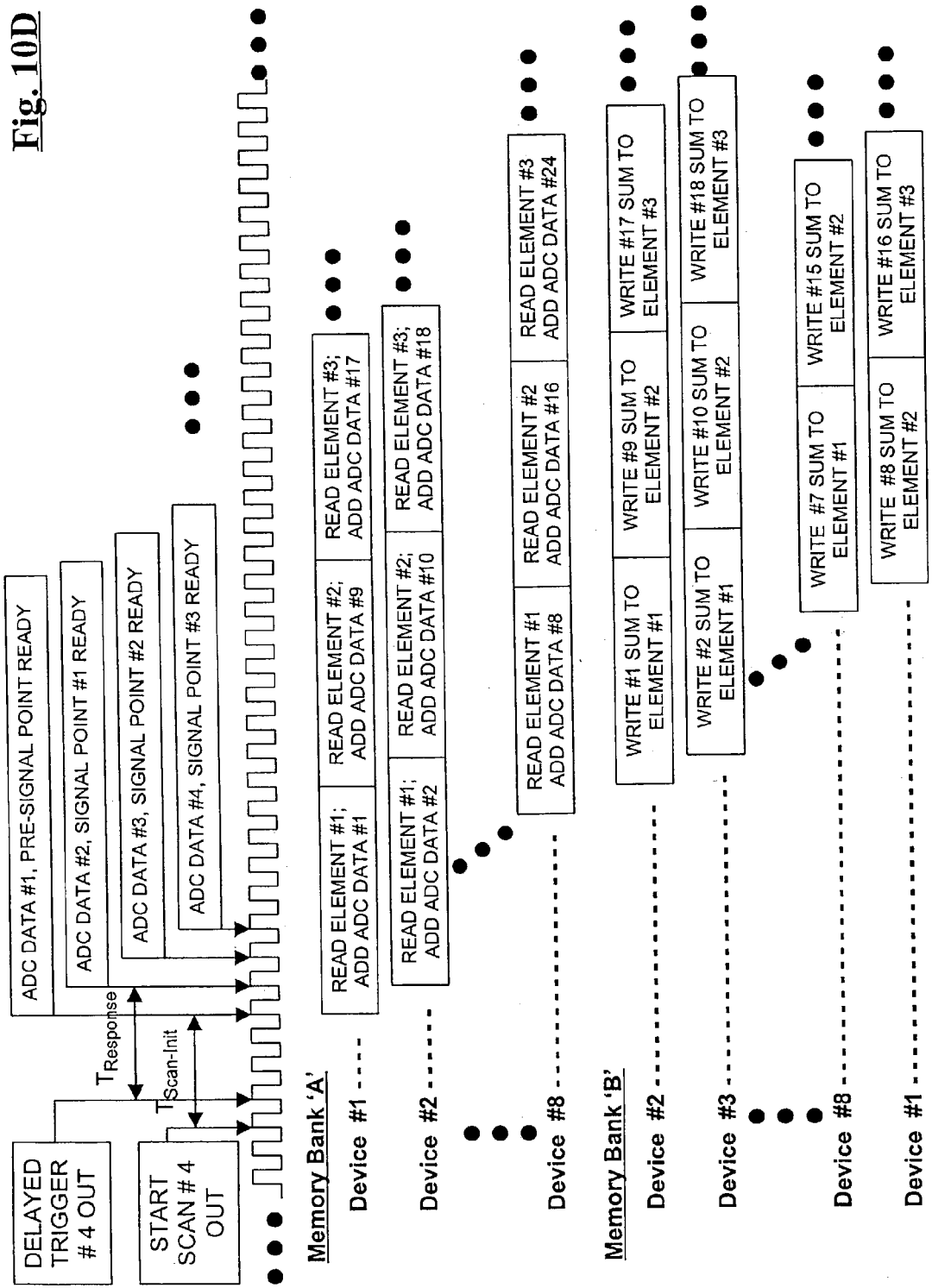
FIG. 10D illustrates a timing diagram associated with one preferred method of operating a particular embodiment of a DSA of the present invention, for the fourth scan of a signal averaging measurement.
Figure 10E:
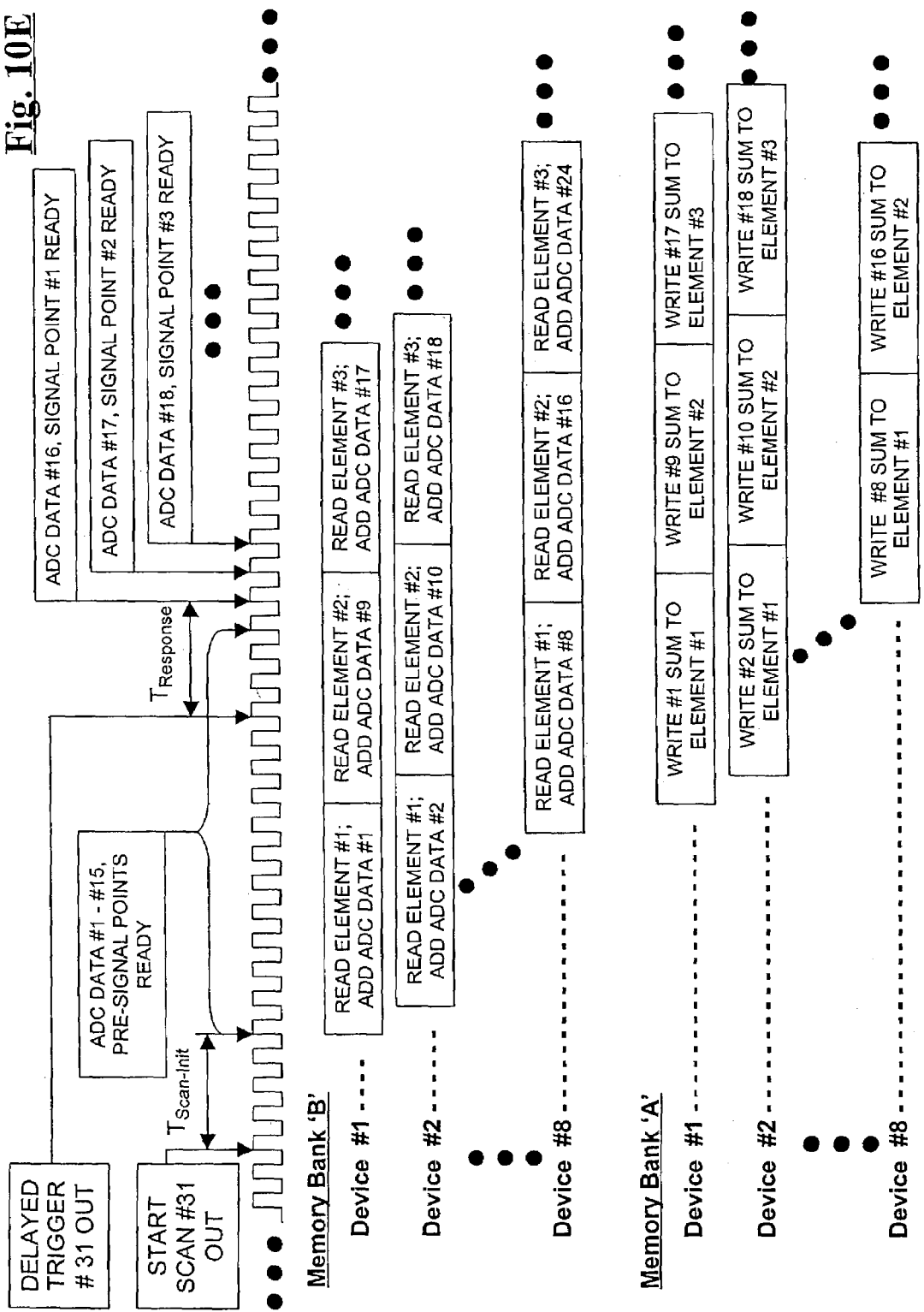
FIG. 10E illustrates a timing diagram associated with one preferred method of operating a particular embodiment of a DSA of the present invention, for the $31^{st}$ scan of a signal averaging measurement.
Figure 10F:
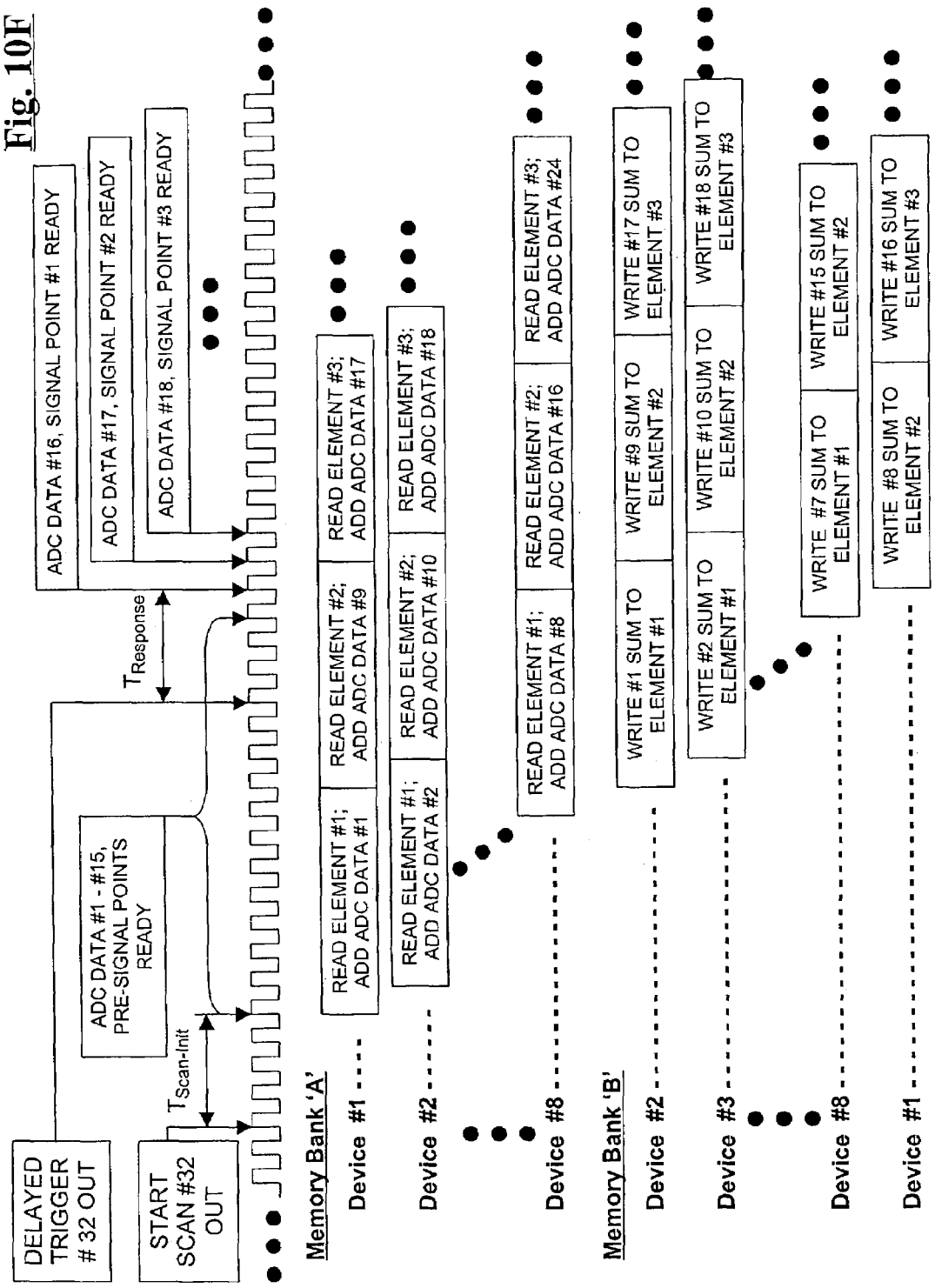
FIG. 10F illustrates a timing diagram associated with one preferred method of operating a particular embodiment of a DSA of the present invention, for the $32^{nd}$ scan of a signal averaging measurement.

The timing diagrams for scans #31 and #32, with trigger delay of 15 ADC intervals, is illustrated in FIGS. 10E and 10F, respectively. Upon completing the scan #32, the trigger delay is reset to 0 for scan #33, and the entire process, as illustrated in FIGS. 10A and 10B for 0 trigger delay, and in FIGS. 10C and 10D for the remaining 15 trigger delays, repeats. Note that after scan #32 is complete, the first point of interest in the summed signal waveform is contained in Memory Bank 'B', Device #1, Element #3. This is the reason that the first scan of each group of 32 scans, such as scan #1, scan #33, scan #65, etc., begins the process of reading previous sum data values with Memory Bank 'B', Device #1, Element #3, as illustrated in FIG. 10A, rather than with Element #1, as with all other scans, as illustrated in FIGS. 10B, 10C, and 10D. In any case, it is expected that this difference in the read, add, write sequence for scans #1 and #2 compared to that of all other scans will result in only negligible, if any, differences in the pattern of coherent noise that is produced, since, for all scans, the same memory devices are addressed, and the results obtained so far indicate that it is the addressing of the memory devices, rather than the addressing of any particular element within a memory device, that generates the coherent noise pattern.

Figure 11A:
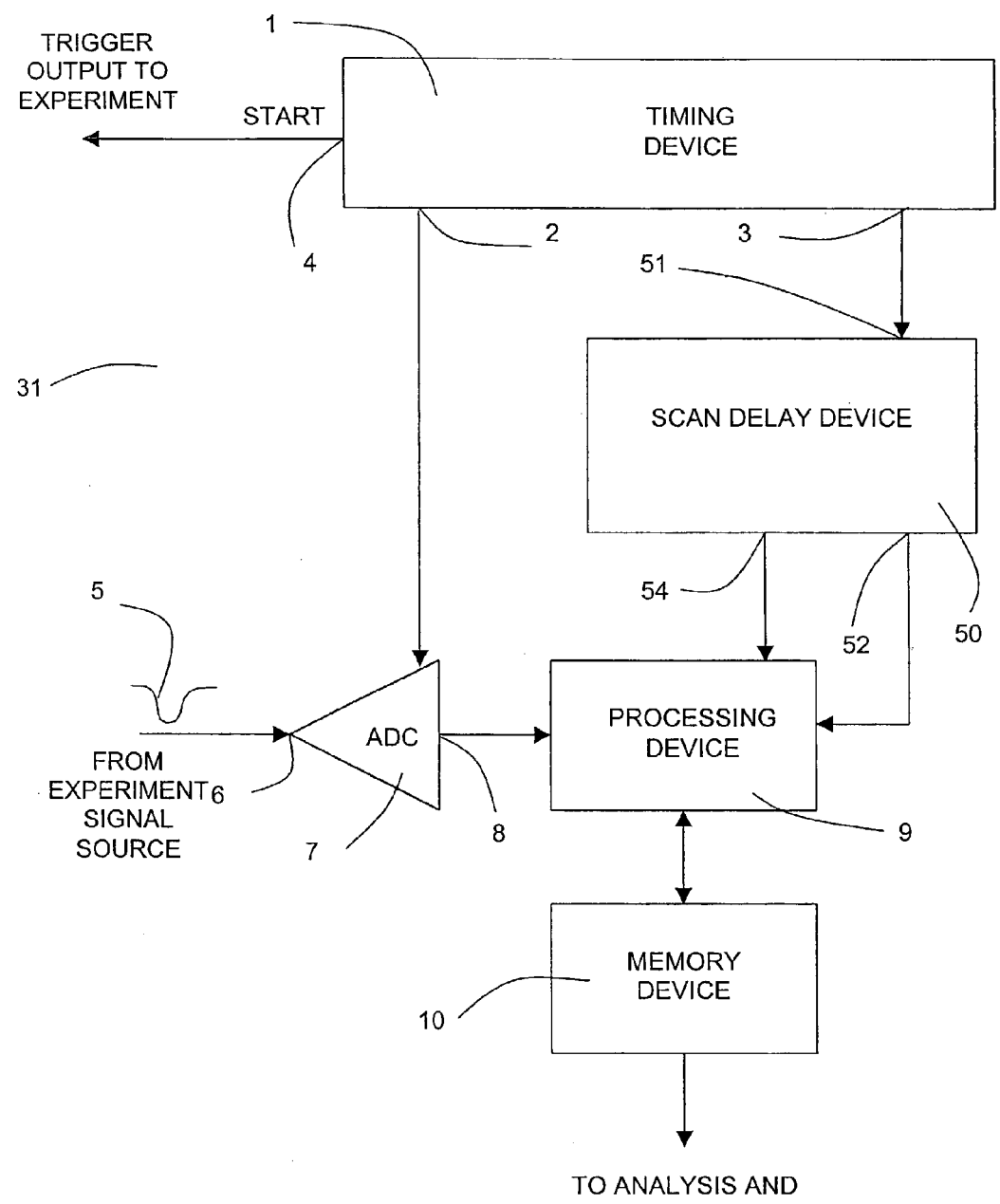
FIG. 11A is a diagram of a DSA according to one preferred embodiment of the present invention.

In another preferred embodiment of the present invention, a digital signal averager may be configured as shown schematically in FIG. 11A. This embodiment of the present invention consists essentially of an ADC 7, a timing device 1, a processing device 9, a memory device 10, and a scan delay device 50.

The timing device 1 includes a precision clock and auxiliary timing circuitry. One function of timing device 1 is to provide a timing signal at output 2 to control the time interval, $T_{Bin}$, between consecutive analog-to-digital conversions by the ADC 7.

A second function of timing device 1 is to provide a Start signal at output 4 that is synchronized with the ADC digitization cycle. This Start signal is generated at the initiation of a new scan measurement sequence and is output to the external experiment to trigger the experiment to generate a signal waveform 5 that is to be measured. The Start signal at output 4 of timing device 1 is also routed to the input 53 of the scan delay device 50.

A third function of timing device 1 is to provide timing signals at output 3, which control the timing of the initiation and subsequent sequence of data transfer, summation, and storage processes that are executed during each scan by the processing device 9. These timing signals at output 3 of timing device 1 are first routed to input 51 of the scan delay device 50. After a time delay, as governed by the scan delay device 50, these timing signals are then routed via output 52 of scan delay device 50 through to the processing device 9. These timing signals are delayed relative to the Start signal by a time delay, $T_{Scan-Delay}$, that is constrained to be an integral number of ADC digitization intervals, that is, $T_{Scan-Delay}$, $=N_{Scan-Delay} T_{Bin}$, where $N_{Scan-Delay}$ is an integer, which may be different for each scan. These timing signals are initiated by timing device 1, generally, after a period of time, $T_{Scan-Init-0}$, relative to the time of the Start signal at output 4 of timing device 1, but before the arrival of the signal waveform of interest 5. The timing signals at output 3 of timing device 1 are then delayed in reaching the processing device 9 by a scan delay time, $T_{Scan-Delay}$. The value of $N_{Scan-Delay}$ is routed to output 54 of scan delay device 50 to the processing device 9 with each scan, so that the processing device 9 may account for the scan delay time in order to properly signal average multiple scans measured with different scan delay times. In this embodiment of the present invention, $T_{Scan-Init-0}$ is defined so as to begin recording a scan prior to the point in time when the signal waveform of interest arrives at the ADC input. The amount of such 'pre-signal' scan recording that is required is given by the maximum scan delay time, $T_{Scan-Delay-Max}$, that will be used during any scan of a signal averaging measurement, in order that the signal waveform of interest is always included in any scan, including the scans recorded with the maximum scan delay time. The data values that result from these operations are stored in memory storage elements of memory array device 10.

Figure 11B:
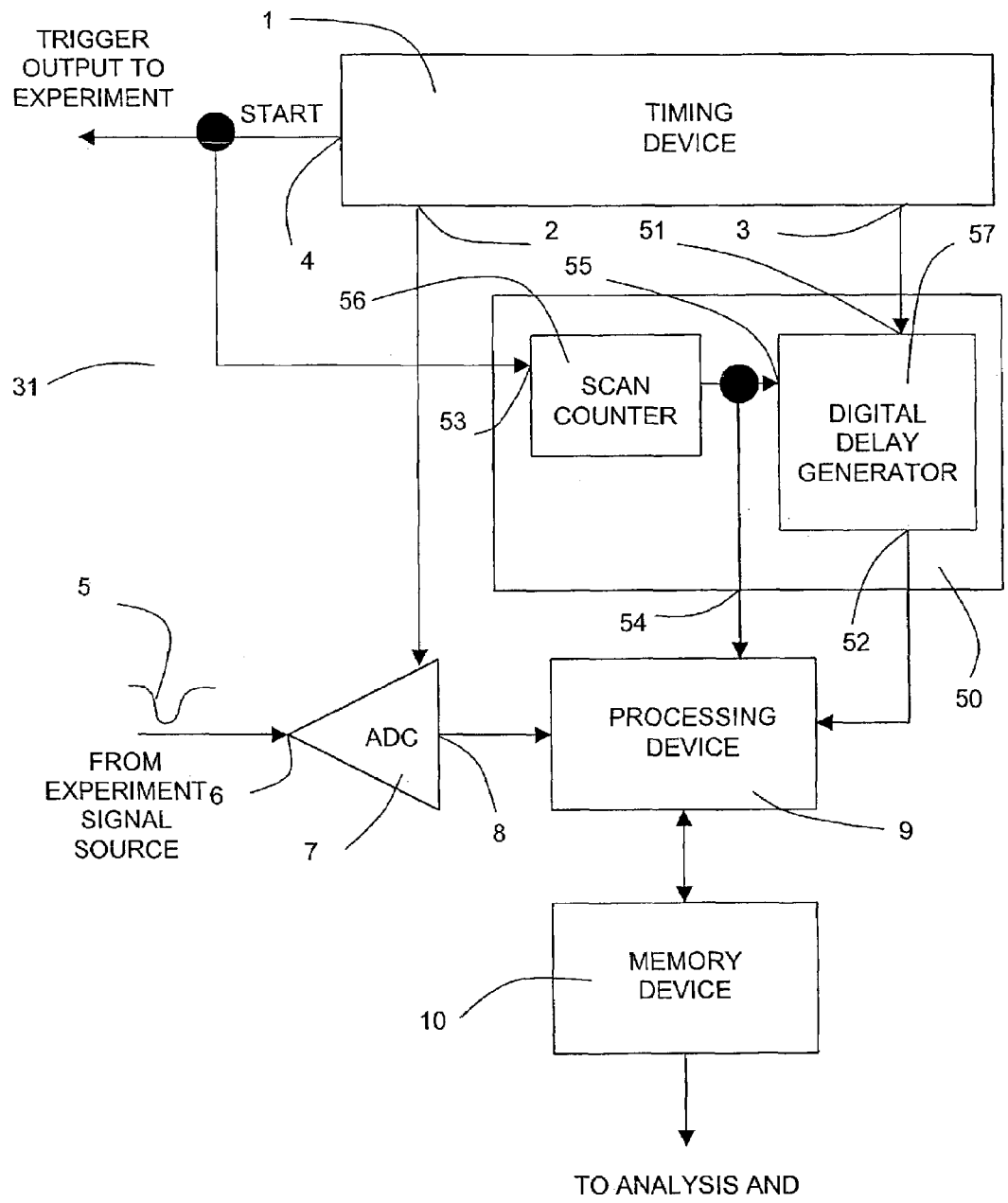
FIG. 11B is a diagram of a DSA according to one preferred embodiment of the present invention, illustrating one possible electronic arrangement that provides a variable scan delay time offset for each scan, starting from 0 nanoseconds and incrementing the trigger delay by 1 ADC interval, in this particular design example, with each subsequent scan.

Because the scan delay time is constrained to be an integral number of ADC intervals, a convenient protocol for varying the scan delay time from one scan to the next is to increment the scan delay time by 1 ADC interval from a minimum number of ADC intervals to some maximum number of ADC intervals, as required by the repeat period of the coherent noise pattern. (An alternate, but equivalent, approach is to decrement the scan delay time by 1 ADC interval from some maximum value to a minimum value of ADC intervals, as required by the repeat period of the coherent noise pattern.) With respect to the former approach, one example implementation of a scan delay device 50, according to one aspect of this embodiment of the present invention, is illustrated conceptually in FIG. 11B. As shown in FIG. 11B, the scan delay device 50 may be configured essentially with a scan counter 56, and a digital delay generator 57. The scan counter 56 is initialized to 0 counts prior to the Start signal at output 4 of timing device 1 for the first scan of a signal averaging measurement. The scan counter 56 is then incremented by 1 after every Start signal that begins each scan. Prior to the Start signal at output 4 of timing device 1 for each scan, the content of scan counter 56 is routed to input 51 of digital delay generator 57. This value determines the amount of delay time by which the digital delay generator delays the timing signals from output 3 of timing device 1, in terms of the number of ADC intervals. For the first scan, then, there is essentially 0 delay between the time when the timing signals are output to output 3 of timing device 1 and the time when such timing signals are provided to the processing device 9 in order to time the data transfer, summation and storage operations of each scan. For each subsequent scan, the scan interval counter is incremented by one, resulting in a delay, by 1 more ADC interval relative to the previous scan, in the routing of the timing signals from output 3 of timing device 1 to the processing device 9, and therefore, an equivalent delay in the time that the scan measurement process is initiated with respect to the Start signal at output 3 of timing device 1.

Again, this is but one specific conceptual implementation according to the methods and devices of the present invention, and those skilled in the art will recognize that many variations of this arrangement will be possible with which to accomplish the same result. For instance, for a particular DSA, it may be advantageous to increment the scan counter 56 by 1 count every other scan, rather than every scan, in order that the scan delay time delay remain the same for each pair of consecutive scans. This scheme may be advantageous in those situations where the pattern of coherent noise is a composite of two different patterns, each pattern possibly produced alternately with every other scan (as discussed below). This is easily accomplished, for example, by routing the 2's digit output of the scan counter 56 to the 1's digit input of the digital delay generator 57, routing the 4's digit output of the scan counter 44 to the 2's digit input of the digital delay generator 57, etc.

The number of scans that are optimum to sum before the scan delay returns to 0 (or whatever the minimum scan delay time is used) to begin the cycle again, depends on the details of the coherent noise pattern that is manifest in a particular DSA. For example, it may be only necessary, for maximum reduction in coherent noise, to sum 16 scans, each with different scan delay value, which would be appropriate for coherent noise that has a period corresponding to 16 ADC intervals, before repeating the cycle. In this case, the scan counter may be configured as a 4-bit counter, which counts from 0 to 15 before returning to 0 on the next count, in response to the $16^{th}$ Start signal at output 4 of timing device 1. In another example, where two different patterns of coherent noise are produced alternately with every other scan, it may be necessary to double the number of scans that would otherwise be required if only a single pattern of coherent noise was produced. In this case, if the repeat pattern for either of the coherent noise patterns is 16 ADC intervals, then the trigger delay would need to vary by 1 ADC interval from 0 to 15 ADC intervals, but the trigger delay may only be incremented every other scan, so that 32 scans would be required for maximum reduction in the coherent noise. The scan counter would then need to reset to 0 every $32^{nd}$ scan. In this case, the scan counter may be configured as a 5-bit counter, which counts from 0 to 31 (for a total of 32 scans) before returning to 0 on the next count (the $32^{nd}$ scan), in response to the $32^{nd}$ Start signal at output 4 of timing device 1.

Now, in one preferred method of operation of this embodiment of the present invention, a signal averaging measurement sequence may begin by loading zeros into all memory storage locations. For the first scan, $N_{Scan\text{-}Delay}$ is set equal to a first integer value, which may arbitrarily be 0 for the sake of simplicity, in which case, for this first scan, the timing signals at output 3 of timing device 1 are not delayed at all by the scan delay device 50 in reaching the input of the processing device 9. In response to the Start signal at output 4 of timing device 1, the external experiment generates a response signal waveform, which is routed to the input 6 of the ADC 7. Generally, the portion of the response signal waveform that is of interest 5 will arrive at the input 6 of the ADC7 a period of time, $T_{Response}$, following the receipt of the Start signal by the experiment. Therefore, the timing signals at output 3 of timing device 1 are generated at a time, $T_{Scan\text{-}Ini\text{-}0}$, after the Start signal that is less than or equal to $T_{Response}$. However, the timing signals from output 4 of timing device 1 will be delayed by a maximum time delay of $T_{Scan\text{-}Delay\text{-}Max}$ for some of the scans in the signal average measurement. Therefore, in order to ensure that the portion of the digitized response signal waveform that is of interest is included in every scan, $T_{Scan\text{-}Init\text{-}0}$ is required to be less than the difference between this experiment response time and the maximum time delay, i.e., $T_{Scan\text{-}Init\text{-}0}$ $T_{Response}$-$T_{Scan\text{-}Delay\text{-}Max}$. The value that is chosen for $T_{Scan\text{-}Init\text{-}0}$ is kept constant for all scans of the signal average measurement.

For the second scan, $N_{Scan\text{-}Delay}$ may be set equal to an integer value that is different from that of the first scan. For example, $N_{Scan\text{-}Delay}$ may be incremented by 1, in which case, for this second scan, the timing signals at output 3 of timing device 1 are delayed by 1 more ADC interval relative to the Start signal, than for the first scan. Therefore, as discussed above, the sequence of data transfer, summation, and storage operations is commenced for this second scan at a point in time relative to the Start signal that is 1 ADC interval later than for the first scan. However, the response signal waveform 5 is generated at the input 6 of the ADC 7 at the same time relative to the Start signal in this second scan as in the first scan. Hence, the first digitized value of the signal waveform of interest occurs 1 data point earlier in the scan measurement of this second scan than in that of the first scan. Similarly, the second digitized value of the signal waveform of interest occurs 1 data point earlier in the scan measurement of this second scan than in that of the first scan, and so on for all data values of the second scan.

In order to properly sum the second scan with the first scan, according to one aspect of the present invention, the processing device takes the relative time shift between the scans into account when summing each new ADC data value in the second scan with the data value of the first scan that corresponds to the same point in time on the signal waveform as the new data value of the second scan. This may be accomplished in a number of ways. For example, according to one aspect of this embodiment of the present invention, as illustrated in FIG. 11, the scan delay device provides at output 54 the value of each current scan delay that is being used in the current scan, and this information is transferred to an input of the processing device, which then compensates for the scan delay time as the spectrum is summed with previously measured spectra.

In another preferred aspect of this embodiment, a fixed protocol may be established whereby the initial scan delay time for the first scan of each signal average measurement is always the same, such as 0, with subsequent scan delays being incremented by a fixed number of ADC intervals, such as by 1 interval, in subsequent scans. Such a fixed protocol alleviates the requirement to communicate the value for the scan delay in any particular scan by the trigger delay device to the processing device, since the processing device only needs to keep track of the scan number of the current signal averaging measurement to ascertain the current trigger delay. Other protocols may be envisioned that accomplish the same result of properly accounting for the time shifts between scans during the signal averaging process.

For the third and any subsequent scans, $N_{Scan-Delay}$ may similarly be set equal to an integer value that is different from that of the previous scans. For example, $N_{Scan-Delay}$ may be incremented by 1 for each subsequent scan, in which case, for each such subsequent scan, the timing signals from output 3 of timing device 1 are delayed by 1 more ADC interval relative to the Start signal, than for the previous scan. Therefore, the scan measurement process is shifted by one ADO interval for each scan compared to the previous scan, relative to the Start signal, and therefore, relative to the signal waveform of interest. As a new data value is processed during any particular scan, then, according to one aspect of this embodiment of the present invention, the processing device compensates for the time shift of the scan measurement process, relative to the Start signal, for that particular scan, due to the delayed scan value that was used for that scan, in order to properly sum the new data value with the sum of previous scan data values that correspond to the same point in time on the signal waveform.

Because the sequence of data transfer, summation, and storage operations is repeated with the same relative phase with respect to every other scan of the signal average measurement, the noise that is generated by this sequence of operations is repeated in each scan. However, due to the different scan delay times that are used for each scan, with respect to the Start signal, and, therefore, with respect to the signal waveform, each point on the signal waveform is digitized for different scans during a correspondingly different phase of this coherent noise pattern. Therefore, after accounting for the different scan delay times as each scan is signal averaged with previous scans, the level of the coherent noise that is present in any particular point on the averaged signal waveform will tend to be an average of a number of coherent noise levels, where the number of coherent noise levels that are 'sampled', in general, corresponds to the number of different scan delay times that were employed in the signal averaging process, according to the devices and methods of the present invention. As this number increases, therefore, this averaging process reduces the coherent noise in the signal waveform accordingly.

Now, as indicated in a previous discussions, the pattern of coherent noise that is generated by the repetitive sequence of digitization, data transfer, summation, and storage processes will often have a repeat period that is much less than the time duration of a scan. Specifically, it will often be the case that the pattern of coherent noise repeats within the course of a scan every $M_{CN}$ number of sequential ADC digitization intervals, where $M_{CN}$ is much less than $M_{Scan}$, the number of sequential ADC digitization intervals comprising a scan. Therefore, in such cases, it is only necessary to increment the scan delay time parameter, $N_{Scan-Delay}$, by 1 from 0 to $(M_{CN}-1)$, in order to minimize coherent noise in the signal averaged waveform record. From another perspective, $M_{CN}$ represents the number of discrete amplitude levels of coherent noise that are present at any particular value of the waveform signal level. Therefore, by incrementing the scan delay time parameter, $N_{Scan-Delay}$, by 1 from 0 to $(M_{CN}-1)$, each point on the signal waveform is digitized with every value of the coherent noise that is possible for the signal level at that point in the signal waveform. In this case, the coherent noise is minimized at each point in the signal waveform.

Furthermore, it will be appreciated that, frequently, the number of scans, $N_{Ave}$, that are to be included in a particular signal average measurement, will be much greater than the number of scans, $M_{CN}$, that are sufficient to minimize the coherent noise in the final average. In such cases, minimization of the coherent noise in the signal averaged waveform only requires that the number of scans measured with each value of the scan delay time parameter, $N_{Scan-Delay}$ is the same for each value of $N_{Scan-Delay}$. This will ensure that all amplitude levels of the coherent noise pattern are sampled equally, and therefore optimally averaged, at each point in the signal waveform. However, even when all amplitude levels of the coherent noise pattern are not sampled exactly equally, at least some substantial reduction of the coherent noise is nevertheless typically achieved according to the present invention. For example, a situation will often occur in which the number of scans in the final averaged waveform, $N_{Ave}$, is not an integral multiple of $M_{CN}$, but where $N_{Avg}$ is nevertheless much greater than $M_{CN}$. In this situation, it is not possible to arrange that the number of scans measured with each value of $N_{Scan-Delay}$ from n=0 to n=$(M_{CN}-1)$, will be exactly the same. The best that can be achieved is to arrange for the number of scans that are measured with each of some values of $N_{Scan-Delay}$, to be INT$(N_{Ave}/M_{CN})$, where INT indicates that number in the parenthesis is to be truncated to an integer number, while the number of scans that are measured with each of the other values of $N_{Scan-Delay}$, to be INT$(N_{Ave}/M_{CN})+1$. In this case, some values of $N_{Scan-Delay}$ will be used in 1 more scan than some other values of $N_{Scan-Delay}$. However, provided that $N_{Ave}$ is much greater than $M_{CN}$, then $(N_{Ave}/M_{CN})$ will be much greater than 1, and the impact on the reduction of the coherent noise, of some values of $N_{Scan-Delay}$ having been used in 1 more scan than other values of $N_{Scan-Delay}$, will be relatively small.

In situations in which $N_{Ave}$ is not much greater than $M_{CN}$, then the coherent noise will still be reduced, at least to some extent, with the methods and apparatus of the present invention. Nevertheless, in such situations, the coherent noise may be minimized if only the number of scans that are allowed in the average, $N_{Ave}$, is constrained to be an integral multiple of $M_{CN}$. In many situations, such a requirement may not be a serious constraint on the measurement protocol. For example, if $M_{CN}=16$, then a constraint may be placed on the number of scans NAVE that are signal averaged to be an integral multiple of 16. Then, if it were desired to average 1000 scans, the constraint may be that either 992 or 1008 scans per average be specified, either being the closest integral multiple of 16 to 1000, without significant consequences to the measurement process.

In any case, it will be appreciated that the order in which the scan delay values are varied will make no difference to the effectiveness of the coherent noise reduction according to the devices and methods of the present invention. For example, one viable scheme is that $(N_{Ave}/M_{CN})$ number of scans are signal averaged with a fixed scan delay value, and then this process is repeated with each of the other $(M_{CN}-1)$ number of scan delay values in a manner that properly accounts for the scan delays. Another equally effective scheme is to measure $M_{CN}$ number of scans, each with a different scan delay time, and sum them in a manner that accounts for the scan delays of each scan; then, this process may be repeated for $(N_{Ave}/M_{CN})$ number of times.

Figure 12A:
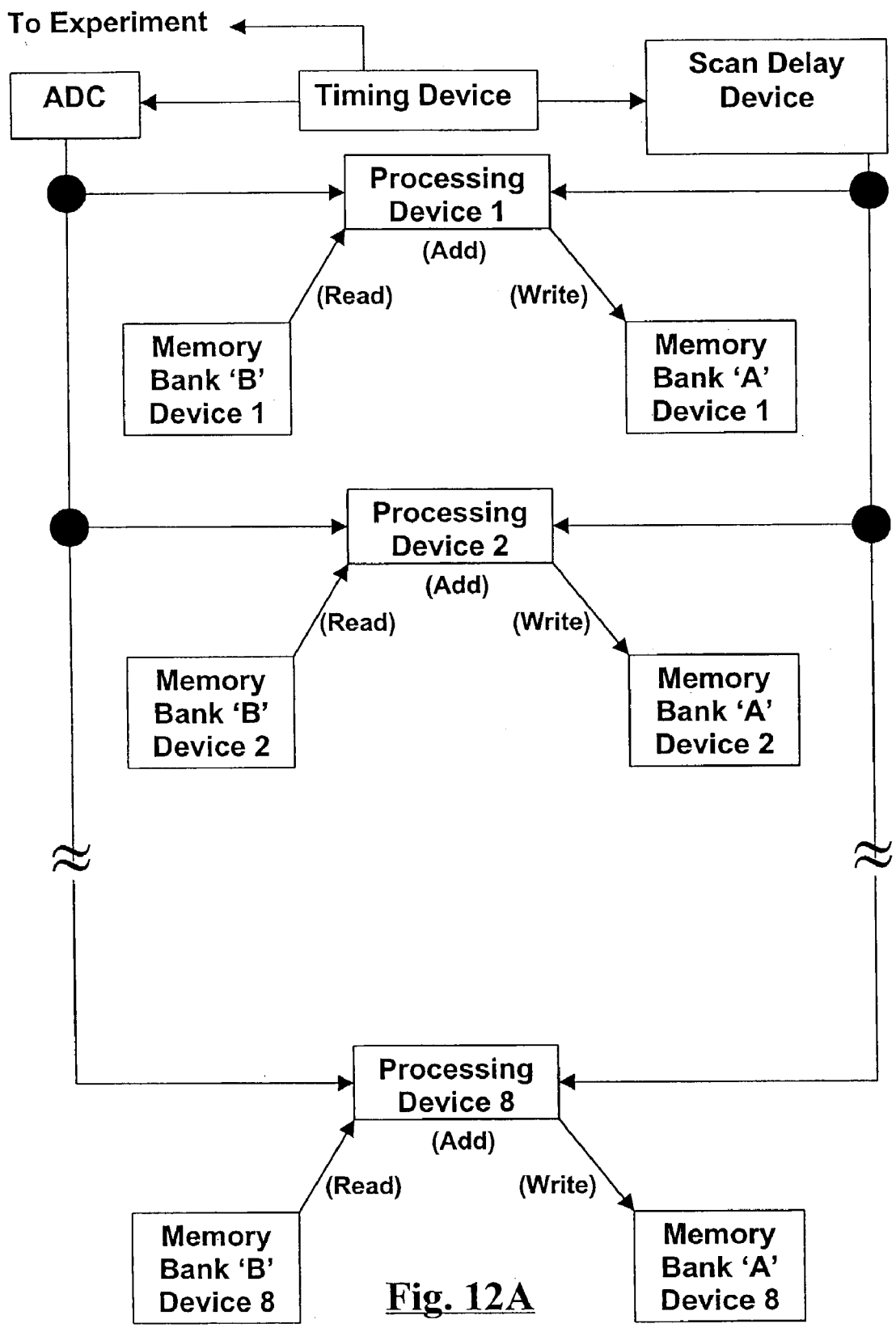
FIG. 12A illustrates a schematic diagram of a DSA showing the parallel-processing memory architecture and the flow of data during a first scan in which previous sum data is read from a first memory array bank, and new sum data is written to a second memory array bank, according to one preferred aspect of the present invention.
Figure 12B:
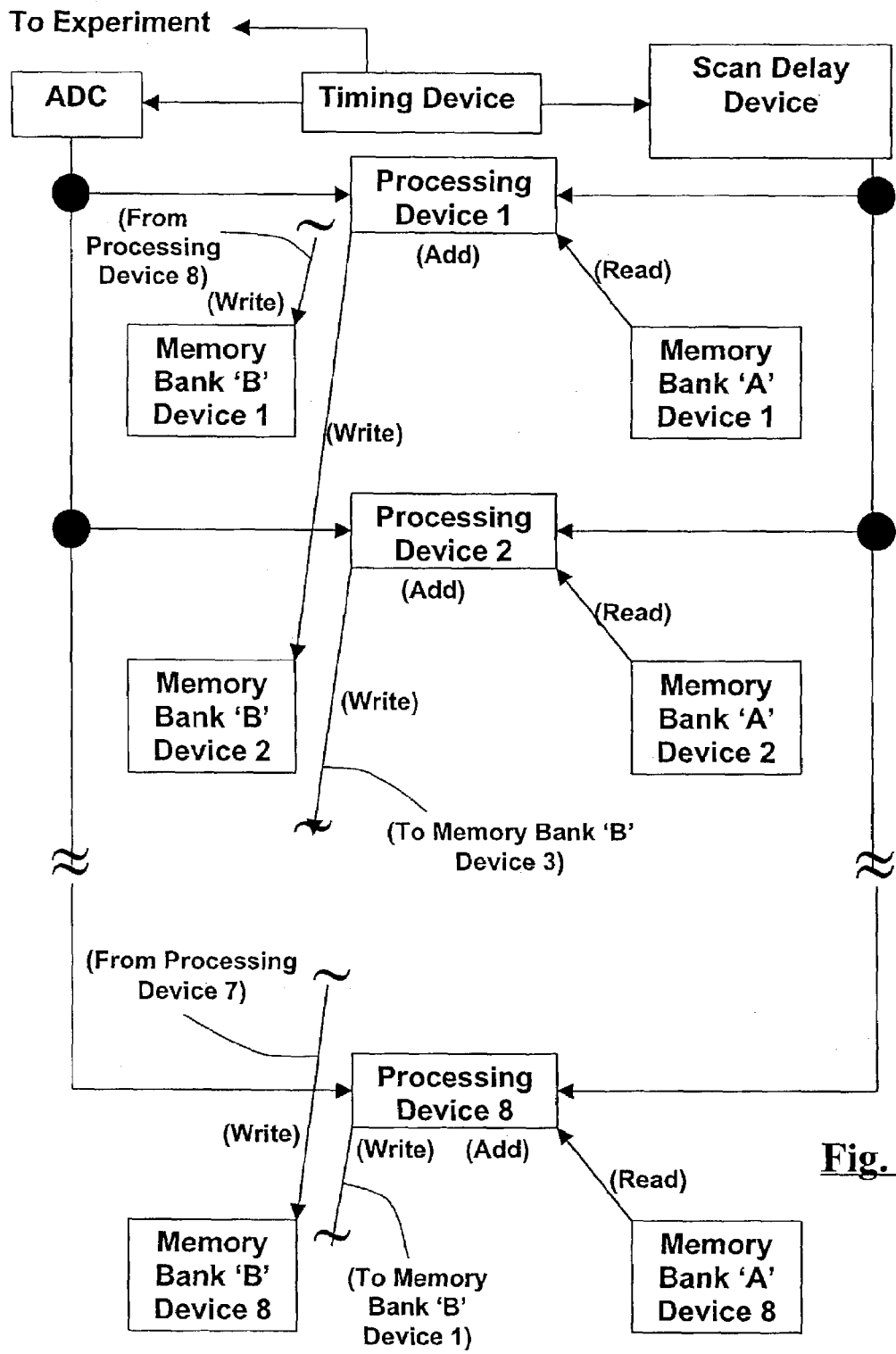
FIG. 12B illustrates a schematic, diagram of a DSA showing the parallel-processing memory architecture and the flow of data during a second scan in which previous sum data is read from the second memory array bank of FIG. 12A, and new sum data is written to the first memory array bank of FIG. 12A, according to one preferred aspect of the present invention.

One preferred embodiment of this approach, as applied to the exemplary EG&G FastFlight DSA, is illustrated in FIGS. 12A and 12B. It will be recognized that the memory array architecture of this embodiment is identical to that of the previously discussed approach as applied to the EG&G FastFlight DSA, as illustrated in FIGS. 9A and 9B. This stems from the fact that, it makes no difference with respect to the ability afforded by the present invention to reduce coherent noise, whether the signal waveform is shifted in time relative to a fixed coherent noise pattern, as in the first preferred embodiment of the present invention discussed above, or whether the coherent noise pattern is shifted in time relative to the signal waveform, as in the second preferred embodiment of the present invention discussed above.

In the implementation illustrated in FIGS. 12A and 12B, the coherent noise pattern is shifted relative to the Start signal by varying the time, relative to the Start signal, at which the scan measurement process begins. The timing device illustrated in FIGS. 12A and 12B functions as in a conventional DSA, that is, by generating the timing signals that begin a scan measurement process after a time period, $T_{Scan-Init-0}$, following the Start signal, which time period is the same for all scans of a signal average measurement. Then the time that the scan measurement process begins is varied from one scan to another by varying the amount by which these timing signals from the timing device are delayed, as given by $T_{Scan-Delay}$, between the Start signal, and the initiation of the sequence of ADC conversion, read, add, and write operations that constitute a scan, for each scan. The timing diagrams that illustrate the sequence of operations according to this embodiment of the present invention are provided in FIGS. 13A through 13F. Again, it will be recognized that the timing diagrams of FIGS. 13A–13F are similar to those of FIGS. 10A–10F. In fact, the read, add, and write operations are identical in both these embodiments, a consequence of the fact that, again, it makes no difference whether the signal waveform is shifted in time relative to a fixed coherent noise pattern, as in FIGS. 10A–10F, or whether the coherent noise pattern is shifted in time relative to the signal waveform, as in FIGS. 13A–13F.

Figure 13A:
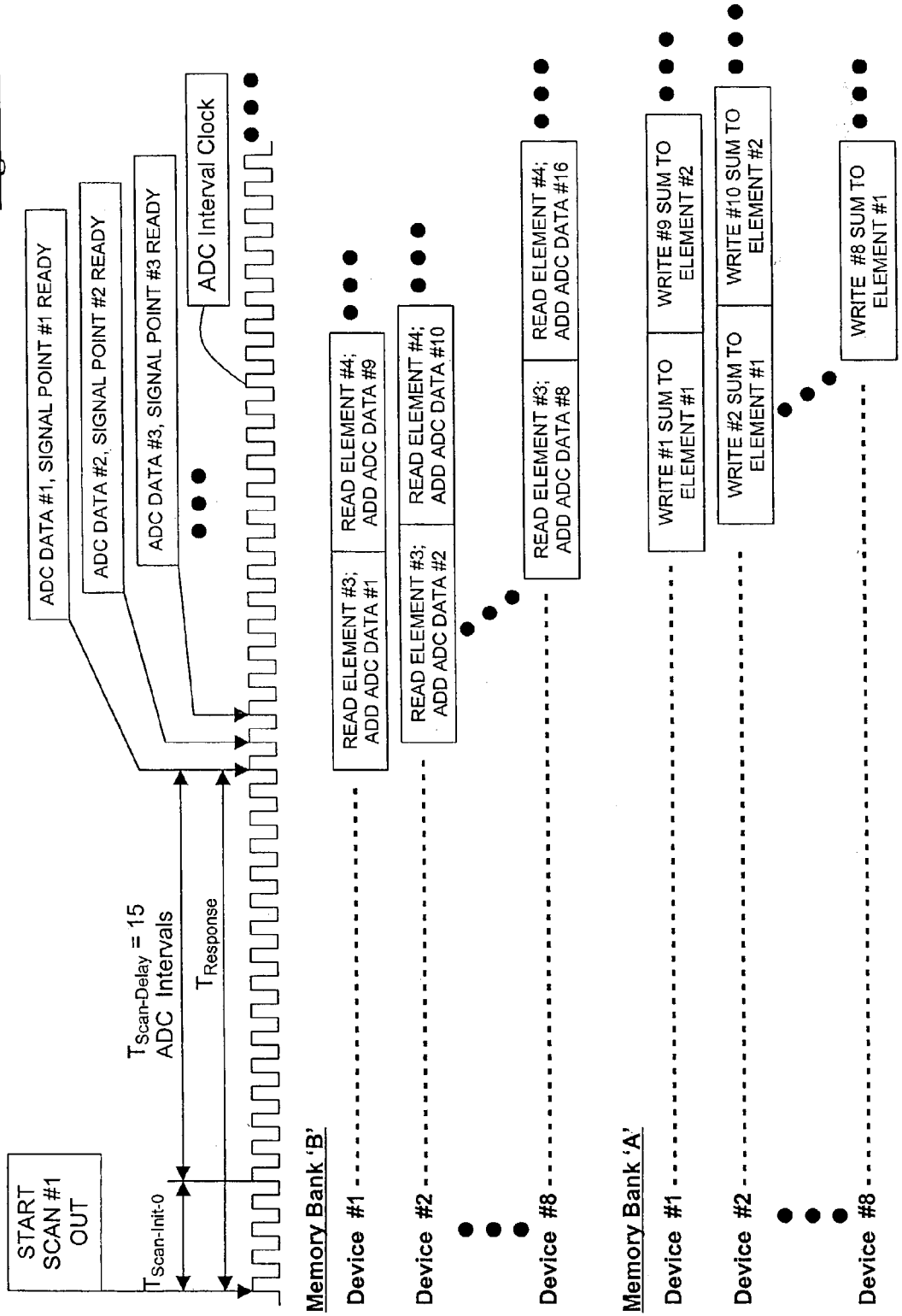
FIG. 13A illustrates a timing diagram associated with one preferred method of operating a particular embodiment of a DSA of the present invention, for the first scan of a signal averaging measurement.

As discussed previously, the EG&G FastFlight DSA exhibits a coherent noise pattern that is periodic with a period of 16 ADC intervals. Therefore, a variation in the scan delay time from 0 to 15 ADC intervals for different scans is adequate to average the coherent noise over all coherent noise values. For purposes of illustration, it is convenient to vary the scan delay time from the maximum value of 15 ADC intervals by decreasing the scan delay time by 1 ADC interval with each subsequent scan until the scan delay time is the minimum of 0. The signal averaging process according to this embodiment of the present invention, then, proceeds as follows: Initially, all memory elements are initialized to zero, or at least the memory elements of memory bank 'B', device #1, and the scan delay counter 56 in FIG. 11B is initialized to 15, the maximum number of ADV intervals that is required to achieve maximum reduction of the coherent noise. Then, the first scan is initiated when the Start signal is generated by the timing device, as indicated on the timing diagram of FIG. 13A as "Start Scan #1 Out", which is output to the experiment to stimulate the generation of the response signal waveform 5. At a point in time 15 ADC intervals prior to the arrival of the response signal waveform at the ADC input, which is the same point in time that is $T_{Scan-Init-0}$ after the Start signal, the timing device begins generating the timing signals that begin the scan recording and signal averaging operation sequence for this first scan. However, due to the scan delay device, these timing signals are delayed by 15 ADC intervals until they actually reach the processor and memory devices. By this time, however, the signal waveform of interest is just arriving at the ADC input, and the first ADC value, ADC Data #1, that is processed in the first scan corresponds to the first point of the signal waveform of interest. At this point in time, Processing Device #1 reads the contents of Memory Bank 'B', Device #1, Element #3, and adds this value (which is 0 for this first scan) to the ADC Data #1 value. These read and add processes are expected to take about 16 nanoseconds, or 8 ADC intervals. The Processing Device #1 then writes the sum data value to Memory Bank 'A', Device #1, Element #1. This write process takes about another 16 nanoseconds. Meanwhile, 2 nanoseconds (1 ADC interval) after ADC Data #1 was generated, the second ADC value, ADC Data #2, is generated. At this point in time, Processing Device #2 reads the contents of Memory Bank 'B', Device #2, Element #3, adds this value (which is 0 for this first scan) to the ADC Data #2 value, and writes the sum to Memory Bank 'A', Device #2, Element #1. This sequence continues for ADC Data #3 through ADC Data #8, involving Processing Devices #3 through #8; Memory Bank 'B', Device #3, Element #3 through Device #8, Element #3; and Memory Bank 'A', Device #3, Element #1 through Device #8, Element #1, in a similar fashion, as illustrated in FIGS. 12A and 13A.

By the time that ADC Data #9 is generated, 16 nanoseconds has past since the last read operation was performed on Memory Bank 'B', Device #1, and this device is again ready to perform a second read operation, specifically of the contents of the next sequential memory location, Element #4, in order to add this value with the ADC Data #9 value. This process continues for each new ADC Data value until the first scan is complete, as illustrated in FIGS. 9A and 10A.

Figure 13B:
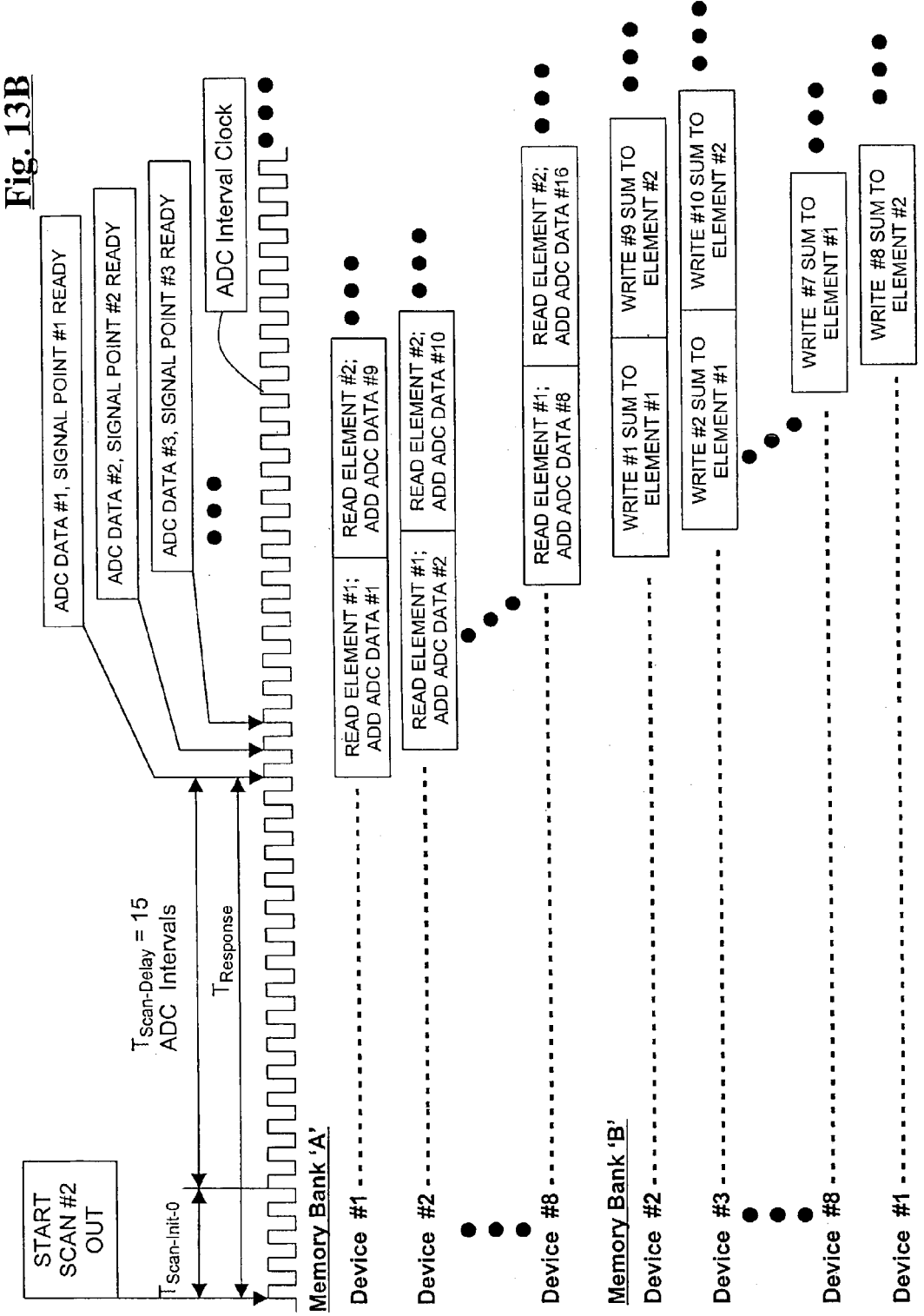
FIG. 13B illustrates a timing diagram associated with one preferred method of operating a particular embodiment of a DSA of the present invention, for the second scan of a signal averaging measurement.

After the first scan is completed, the second scan commences. For this second scan, as illustrated in FIGS. 12B and 13B, a Start signal is generated by the timing device, the scan delay device is kept at 15, and the experiment produces a signal waveform that is a replica, more or less, of the first signal waveform. However, in contrast to the order of operations described above for the first scan, for this second scan, the Memory Devices 'A' are read from, the new ADC Data values are added to these contents, and the sums are written to the Memory Devices 'B'. When ADC Data #1 is generated, the data value in Memory Bank 'A', Device #1, Element #1 is read, and added to ADC Data #1 in Processing Device #1. The resulting sum is written to Memory Bank 'B', Device #2, Element #1. Note that the sum is written to Memory Device #2 of Memory Bank 'B', while the stored data value that was added to the ADC Data #1 resided in Memory Device #1 of Memory Bank 'A'. This process continues, as illustrated in FIGS. 12B and 13B, for subsequent ADC Data values, until, when ADC Data #8 is generated, this data is added to the contents of Memory Bank 'A', Device #8, Element #1, and the resulting sum is written to Memory Bank 'B', Device #1, Element #2. The ninth ADC value, ADC Data #9, is added to the contents of Memory Bank 'A', Device #1, Element #2, and the resulting sum is written to Memory Bank 'B', Device #2, Element #2, and so on. In other words, for this second scan, each new summed data value is always written to the memory element that would have been written to, according to the sequence of the first scan, during the processing of the next ADC Data value, rather than the current ADC Data value. Therefore, the summed signal waveform data is re-aligned, at the end of this second scan, with the memory array elements to correspond with a shift of the data by one ADC interval later in the memory array.

Figure 13C:
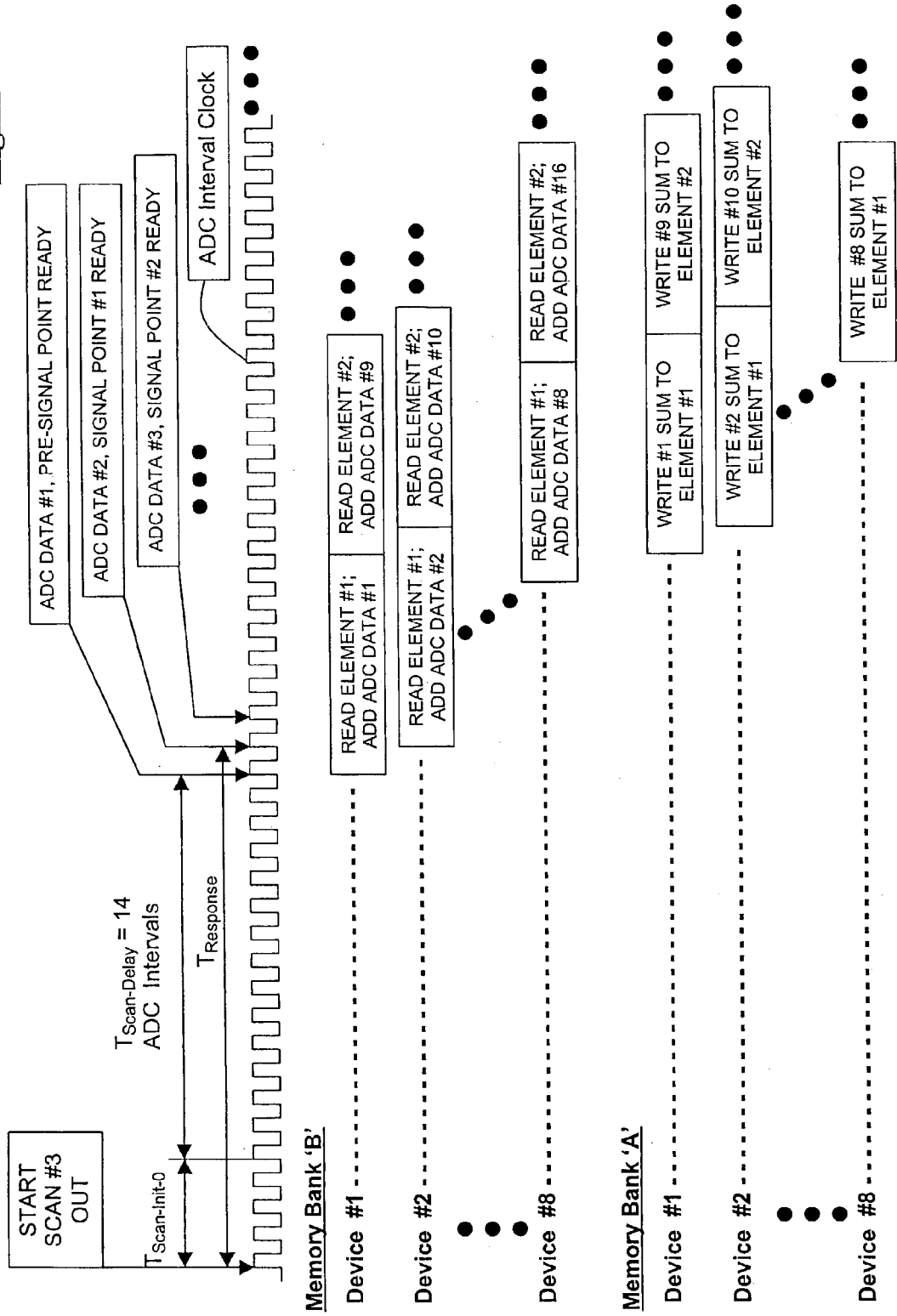
FIG. 13C illustrates a timing diagram associated with one preferred method of operating a particular embodiment of a DSA of the present invention, for the third scan of a signal averaging measurement.

The timing sequence for the third scan is portrayed in FIG. 13C. This sequence is similar to that of the first scan, with two major differences: first, a scan delay of 14 ADC intervals is programmed into the scan delay device, rather than 15 as for the first scan; and second, the sequence of read operations from the Memory Bank 'B' devices begins with Element #1 for each memory device, in contrast to the first scan, which began the read operations with Element #3 from each memory device. The reason for this (that is, for the fact that Element #3 was the element written to during the first and second scans, while Element #1 is the element written to for the subsequent 30 scans) will become clear from the discussion below. The scan delay of 1 less ADC interval results in the scan measurement sequence beginning 1 ADC interval earlier than in the first scan, relative to the Start signal, while the signal waveform arrives at the ADC input at the same time, relative to the Start signal, as for all other scans. From another perspective, the signal waveform as measured in the second scan is shifted by 1 ADC interval later with respect to the beginning of the scan, as compared to that in the first scan. This means that the signal waveform is now properly aligned with the previously shifted summed signal waveform data, allowing a proper summation of new data with previous sum data using the sequence of read, add, and write operations illustrated in FIG. 13C.

For the fourth scan, a scan delay of 1 ADC interval is maintained, and the sequence of operations is identical to that portrayed for the second scan in FIG. 13B. This sequence is reproduced in FIG. 13D, the only difference from the second scan in FIG. 13B being that the scan delay time is 14 ADC intervals in FIG. 13D, in contrast to a scan delay of 15 ADC intervals in FIG. 13B. In both FIGS. 13C and 13D, the scan delay of 14 ADC intervals shifts the signal waveform by 1 ADC interval later with respect to the time at which the first ADC Data #1 value is generated. Hence, these first ADC Data #1 values of Scans #3 and #4 are ultimately ignored; these data values are designated as a "Pre-Signal Point" in FIGS. 13C and 13D.

The processes described above for Scan #3 and Scan #4 are repeated for subsequent pairs of scans, where the scan delay is programmed to be 1 less ADC interval for each subsequent pair of scans. This process continues until 16 different scan delay times have been employed, from a scan delay of 15 ADC intervals for Scan # 1 and Scan #2, to a scan delay of 0 for Scan #31 and Scan #32. Again, the reason that two consecutive scans are summed in this fashion with the same scan delay offset is to ensure that, if two different coherent noise patterns are present, one from the sequence of reading from the Memory Bank 'A' and writing to the Memory Bank 'B' during even (or odd) numbered scans, and other from reading from Memory Bank 'B' and writing to Memory Bank 'A' during odd (or even) numbered scans, both coherent noise patterns will be included in the coherent noise averaging process. Because two scans were measured for each different trigger delay value, the complete process requires 32 scans to measure each signal waveform point in the presence of all possible contributions of the coherent noise pattern.

Figure 13D:
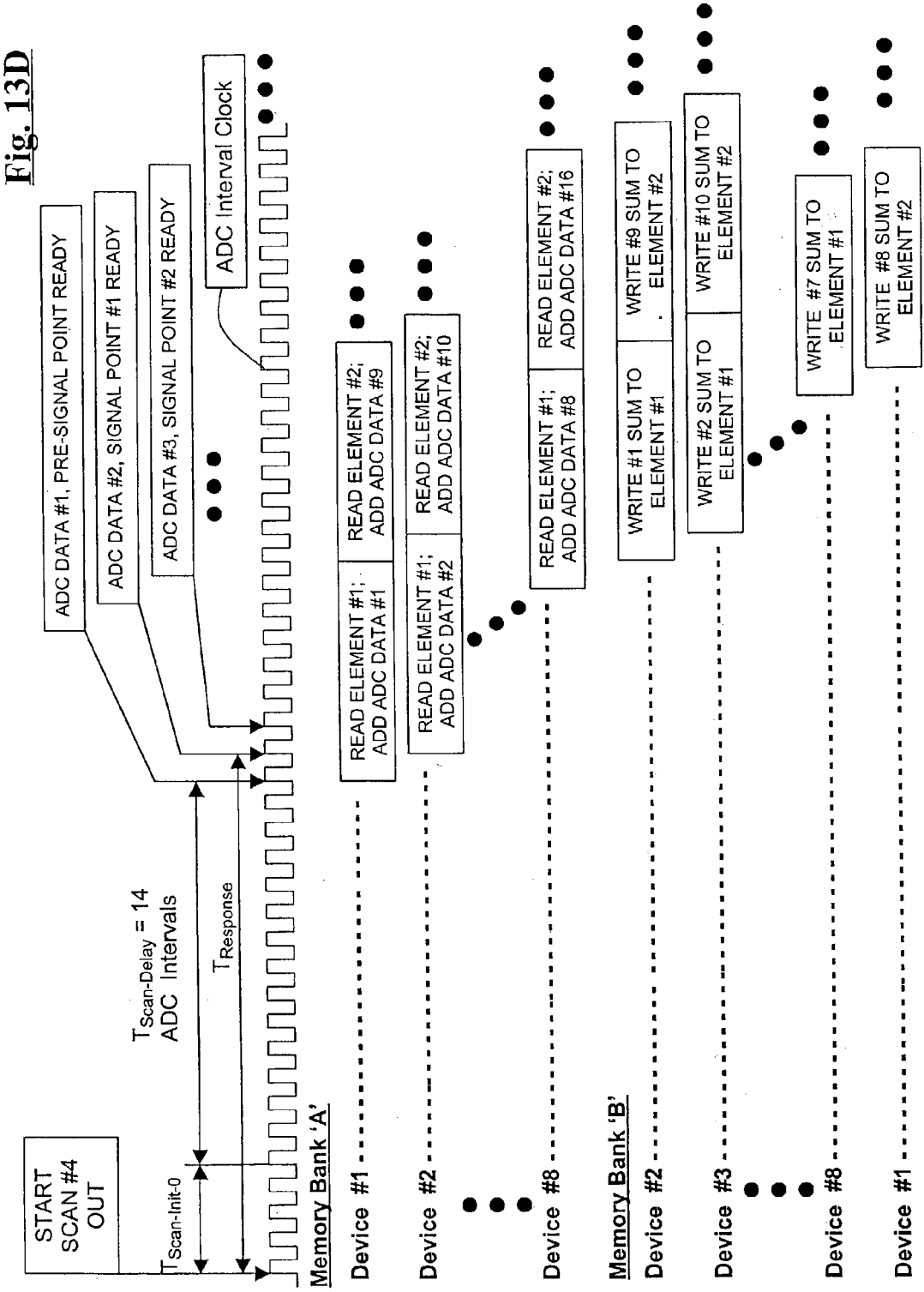
FIG. 13D illustrates a timing diagram associated with one preferred method of operating a particular embodiment of a DSA of the present invention, for the fourth scan of a signal averaging measurement.
Figure 13E:
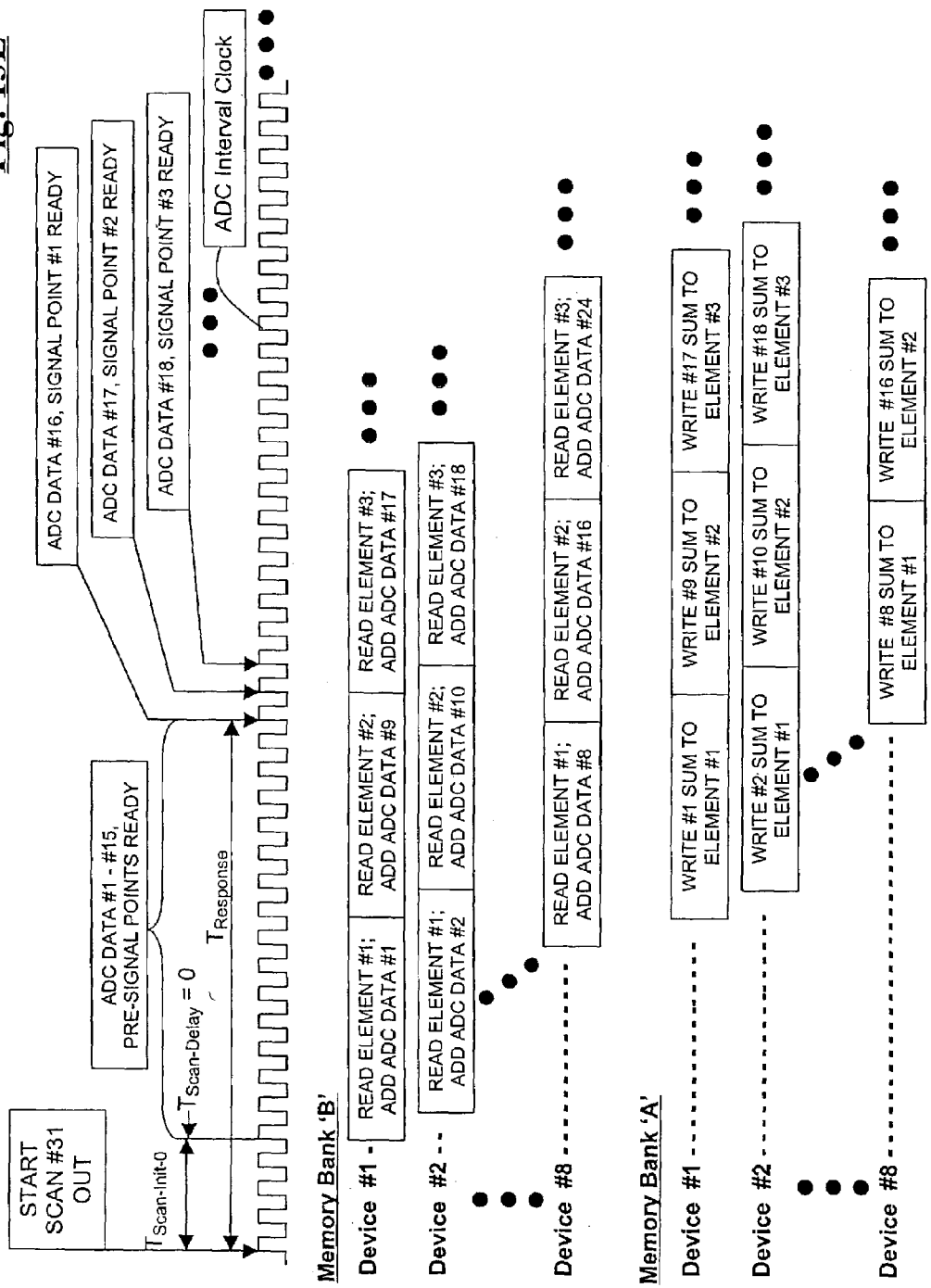
FIG. 13E illustrates a timing diagram associated with one preferred method of operating a particular embodiment of a DSA of the present invention, for the $31^{st}$ scan of a signal averaging measurement.

The timing diagrams for scans #31 and #32, with trigger delay of 0, is illustrated in FIGS. 13E and 13F, respectively. Upon completing the scan #32, the scan delay is reset to 15 for scan #33, and the entire process, as illustrated in FIGS. 13A and 13B for a scan delay of 15 ADC intervals, and in FIGS. 13C and 13D for the remaining 15 scan delays, repeats. Note that after scan #32 is complete, the first point of interest in the summed signal waveform is contained in Memory Bank 'B', Device #1, Element #3. This is the reason that the first scan of each group of 32 scans, such as scan #1, scan #33, scan #65, etc., begins the process of reading previous sum data values with Memory Bank 'B', Device #1, Element #3, as illustrated in FIG. 13A, rather than with Element #1, as with all other scans, as illustrated in FIGS. 13B, 13C, and 13D. In any case, it is expected that this difference in the read, add, write sequence for scans #1 and #2 compared to that of all other scans will result in only negligible, if any, differences in the pattern of coherent noise that is produced, since, for all scans, the same memory devices are addressed, and the results obtained so far indicate that it is the addressing of the memory devices, rather than the addressing of any particular element within a memory device, that generates the coherent noise pattern.

The foregoing discussions of all preferred embodiments have tended to emphasize time delays, such as the delay of the signal generation relative to the data acquisition processes and the delay of the data acquisition processes relative to the generation of the signal, that are integral multiples of the ADC sampling interval. However, as alluded to previously, it should be understood that reduction of coherent noise is also realized, and it is within the scope of the present invention, when such time delays are not integral multiples of the ADC sampling interval, but may be integral multiples of some other time interval, or even random in nature.

It should also be further understood that, while the foregoing discussions have tended to emphasize embodiments of the present invention in which the generation of a repetitive signal waveform is stimulated in response to a trigger signal from the DSA, the apparatus and methods of the present invention also results in reduction of coherent noise in measurements of repetitive signal waveforms that are not generated in response to a trigger signal from the DSA, as alluded to previously. In such cases, the DSA typically detects a particular feature in the repetitive signal waveform to be signal averaged and a scan measurement and summation cycle is initiated in response to this detection. Reduction of coherent noise is realized within the scope of the present invention if the devices of the DSA, which are accessed in the processes of digitization, summation and data transfer associated with each scan, are changed from one scan to another, similar to the approach described above in conjunction with FIGS. 12 and 13.

The preceding examples of implementations of the devices and methods of the present invention serve to demonstrate that the specific details of any such implementation will depend on the particular timing and memory array architecture employed in a particular DSA. Other DSA's may be designed with different architectures, and design details required to implement the devices and methods of the present invention into any such different architecture will be apparent to those skilled in the art. Any such implementation is considered within the scope of the present invention.

It is also within the scope of the present invention to combine the devices and methods of the present invention with other DSA improvements that have been invented or otherwise developed or established. Specifically, the devices and methods of the present invention may be combined with the "precision enhancement" functionality that has been described by Gedcke, et. al., in U.S. Pat. No. 6,028,543. The devices and methods of the present invention may also be combined with the "interleaved sampling" functionality to improve the time resolution of the DSA, which has been described by Peck, et. al., in U.S. Pat. No. 6,094,627. With both of these enhancements, the maximum reduction of coherent noise requires that each scan, which is measured with a different amplitude offset in the case of "precision enhancement", and/or with a different interleave time offset in the case of "interleaved sampling", is repeated while signal averaging is performed according to the present invention. For example, with the EG&G FastFlight DSA, it is possible to perform "interleaved sampling", whereby each scan is repeated 4 times with an interleaved time delay difference between scans of 0.5 nanoseconds. The composite scan constructed by combining these 4 scans, then, exhibits an effective sampling rate of 2 Gigahertz, or 0.5 nanoseconds time resolution, while each scan is measured with a sampling rate of 2 nanoseconds per ADC interval. The coherent noise may be is minimized, then, if each of these 4 scans is measured, in turn, 32 times using the coherent noise reduction devices and methods of the present invention as described above. The composite interleaved scan may then be constructed in the conventional manner as before. Alternatively, the 4 scans may be measured in an interleaved fashion, in the conventional manner, to produce a composite interleaved scan of 4 scans offset by 0.5 nanoseconds. This process may then be repeated 32 times according to the devices and methods of the present invention, as described above, to produce a final signal averaged measurement with minimized coherent noise and a time resolution of 0.5 nanoseconds.

While the foregoing specification describes a digital signal averager with coherent noise reducing capabilities in conjunction with a time-of-flight mass spectrometer, one skilled in the art will recognize that the high performance digital signal averager 31 can be used in conjunction with an analog signal source from other apparatus.

From the foregoing descriptions, it will be recognized by those skilled in the art that a digital signal averager offering advantages over prior art has been provided. Specifically, the digital signal averager of the present invention provides devices and methods for measuring repetitive signal waveforms with reduced coherent noise due to internally-generated noise signals, which leads to improved signal-to-noise ratio characteristics and therefore improved dynamic range and sensitivity, without significant impact on cost or complexity relative to conventional hardware.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

What is claimed is:

1. A digital signal averager for averaging a plurality of scans, wherein each of said scans comprises digital signal data measured from an analog signal, said digital signal averager comprising:
   (a) a timing device for generating a start pulse and a first plurality of timing pulses for each of said scans;
   (b) a time delay device for generating a trigger pulse following said start pulse by a variable time delay, whereby said trigger pulse stimulates an analog signal source to generate said analog signal;
   (c) means for controlling the magnitude of said variable time delay for each of said scans;
   (d) an analog-to-digital converter for converting said analog signal to digital signal data in response to a second plurality of timing pulses;
   (e) said second plurality of timing pulses comprising a subset of said first plurality of timing pulses; and
   (f) means for averaging said plurality of scans whereby said variable time delay is corrected for each of said scans such that the same point in the phase of said analog signal is averaged using scans measured with different time delays in the averaging process to average out the internal noise that is coherent with the scanning process.

2. An apparatus according to claim 1 wherein said analog signal source comprises a time-of-flight mass spectrometer.

3. An apparatus according to claim 1 wherein said means for averaging said plurality of scans operates synchronously with said first plurality of timing pulses.

4. An apparatus according to claim 1 wherein said means for averaging said plurality of scans operates independent of said first plurality of timing pulses.

5. An apparatus according to claim 1 wherein means for controlling the magnitude of said variable time delay comprises a counting device that increments with each of said scans.

6. An apparatus according to claim 1 wherein means for controlling the magnitude of said variable time delay comprises a programmable register that may be programmed with a different value for the time delay with each of said scans.

7. An apparatus according to claim 1 wherein means for controlling the magnitude of said variable time delay comprises a random number generator that may generate a different random value for the time delay with each of said scans.

8. An apparatus according to claim 1 further comprising means for adjusting the signal amplitude offset prior to the input of said analog-to-digital converter.

9. An apparatus according to claim 1 further comprising means for filtering noise from said digital signal data.

10. An apparatus according to claim 1, wherein said first and second plurality of timing pulses are identical.

11. An apparatus according to claim 1 wherein consecutive timing pulses of said plurality of timing pulses are separated by a substantially constant time interval.

12. An apparatus according to claim 11 wherein said variable time delay may be an integral multiple of said substantially constant time interval.

13. An apparatus according to claim 1 wherein said means for averaging said plurality of scans comprises at least one processing device for summing said digital signal data and at least one memory device for storage of summed digital signal data.

14. An apparatus according to claim 13 wherein said at least one processing device comprises a plurality of gate array devices.

15. An apparatus according to claim 13 wherein said at least one processing device comprises at least one computer central processing unit.

16. An apparatus according to claim 13 further comprising means for filtering noise from said summed digital signal data.

17. An apparatus according to claim 13 further comprising means for subtraction of summed digital background signal data, comprising coherent noise, from said summed digital signal data.

18. A digital signal averager for averaging a plurality of scans, wherein each of said scans comprises digital signal data measured from an analog signal, said digital signal averager comprising:
- (a) a timing device for generating a start pulse and a first plurality of timing pulses for each of said scans, whereby said start pulse stimulates an analog signal source to generate said analog signal;
- (b) a time delay device for generating a variable time delay between said start pulse and said timing pulses for each of said scans;
- (c) means for controlling the magnitude of said variable time delay for each of said scans;
- (d) an analog-to-digital converter for converting said analog signal to digital signal data in response to a second plurality of timing pulses;
- (e) said second plurality of timing pulses comprising a subset of said first plurality of timing pulses; and
- (f) means for averaging said plurality of scans whereby said variable time delay is corrected for each of said scans such that the same point in the phase of said analog signal is averaged using scans measured with different time delays in the averaging process to average out the internal noise that is coherent with the scanning process.

19. An apparatus according to claim 18 wherein said analog signal source comprises a time-of-flight mass spectrometer.

20. An apparatus according to claim 18 wherein said means for averaging said plurality of scans operates synchronously with said first plurality of timing pulses.

21. An apparatus according to claim 18 wherein said means for averaging said plurality of scans operates independent of said first plurality of timing pulses.

22. An apparatus according to claim 18 wherein means for controlling the magnitude of said variable time delay comprises a counting device that increments with each of said scans.

23. An apparatus according to claim 18 wherein means for controlling the magnitude of said variable time delay comprises a programmable register that may be programmed with a different value for the time delay with each of said scans.

24. An apparatus according to claim 18 wherein means for controlling the magnitude of said variable time delay comprises a random number generator that may generate a different random value for the time delay with each of said scans.

25. An apparatus according to claim 18 further comprising means for adjusting the signal amplitude offset prior to the input of said analog-to-digital converter.

26. An apparatus according to claim 18 further comprising means for filtering noise from said digital signal data.

27. An apparatus according to claim 18, wherein said first and second plurality of timing pulses are identical.

28. An apparatus according to claim 18 wherein consecutive timing pulses of said first plurality of timing pulses are separated by a substantially constant time interval.

29. An apparatus according to claim 28 wherein said variable time delay may be an integral multiple of said substantially constant time interval.

30. An apparatus according to claim 18 wherein said means for averaging said plurality of scans comprises at least one processing device for summing said digital signal data and at least one memory device for storage of summed digital signal data.

31. An apparatus according to claim 30 wherein said at least one processing device comprises a plurality of gate array devices.

32. An apparatus according to claim 30 wherein said at least one processing device comprises at least one computer central processing unit.

33. An apparatus according to claim 30 further comprising means for filtering noise from said summed digital signal data.

34. An apparatus according to claim 30 further comprising means for subtraction of summed digital background signal data, comprising coherent noise, from said summed digital signal data.

35. A digital signal averager for averaging a plurality of scans, wherein each of said scans comprises digital signal data measured from an analog signal, said digital signal averager comprising:
- (g) means for detection of a particular feature of a repetitive analog signal;
- (h) means for generating a trigger signal in response to said detection;
- (i) means for generating a first plurality of timing pulses substantially synchronous with said trigger signal for each of said scans;
- (j) an analog-to-digital converter for converting said analog signal to digital signal data in response to a second plurality of timing pulses;
- (k) said second plurality of timing pulses comprising a subset of said first plurality of timing pulses;
- (l) an averaging device for averaging said digital signal data, said averaging device comprising a plurality of processing devices for summing said digital signal data and a plurality of memory devices for storage of summed digital signal data; and,
- (m) means for selecting the sequence in which a plurality of processing devices for summing said digital signal data and memory devices for storage of summed digital data are utilized during each of said scans.

36. An apparatus according to claim 35 wherein said analog signal source comprises a time-of-flight mass spectrometer.

37. An apparatus according to claim 35 wherein consecutive timing pulses of said first plurality of timing pulses are separated by a substantially constant time interval.

38. An apparatus according to claim 35 wherein said plurality of processing devices comprises a plurality of gate array devices.

39. An apparatus according to claim 35 wherein said plurality of processing devices comprises at least one computer central processing unit.

40. An apparatus according to claim 35 wherein said means for averaging said plurality of scans operates synchronously with said first plurality of timing pulses.

41. An apparatus according to claim 35 wherein said means for averaging said plurality of scans operates independent of said first plurality of timing pulses.

42. An apparatus according to claim 35 further comprising means for adjusting the signal amplitude offset prior to the input of said analog-to-digital converter.

43. An apparatus according to claim 35 further comprising means for filtering noise from said digital signal data.

44. An apparatus according to claim 35 further comprising means for filtering noise from said summed digital signal data.

45. An apparatus according to claim 35 further comprising means for subtraction of summed digital background signal data, comprising coherent noise, from said summed digital signal data.

46. An apparatus according to claim 35, wherein said first and second plurality of timing pulses are identical.

47. A method for averaging digital signal data generated from a plurality of scans of an analog signal, said method comprising:
  (a) setting a first time delay in a time delay device;
  (b) generating a start pulse with a timing device;
  (c) generating a trigger pulse with said time delay device following said start pulse by said first time delay, whereby said trigger pulse stimulates an analog signal source to generate an analog signal;
  (d) generating timing pulses with said timing device;
  (e) converting said analog signal to digital signal data with an analog-to-digital converter in response to each of at least a subset of said timing pulses;
  (f) summing each of said digital signal data with the sum of digital signal data, acquired from any previous scans with at least one time delay that is different from said first time delay, that corresponds to the same phase of said analog signal;
  (g) repeating steps (a) through (f) wherein said first time delay may be changed to a different time delay for each of said scans.

48. A method for averaging digital signal data generated from a plurality of scans of an analog signal, said method comprising:
  (a) setting a first time delay in a time delay device;
  (b) generating a start pulse with a timing device, whereby said start pulse stimulates an analog signal source to generate an analog signal;
  (c) generating timing pulses with said timing device;
  (d) converting said analog signal to digital signal data with an analog-to-digital converter, in response to each of at least a subset of said timing pulses, whereby commencement of said converting follows said start pulse by said first time delay;
  (e) summing each of said digital signal data with the sum of digital signal data, acquired from any previous scans with least one time delay that is different from said first time delay, that corresponds to the same phase of said analog signal;
  (f) repeating steps (a) through (e) wherein said first time delay may be changed to a different time delay for each of said scans.

49. A method for averaging digital signal data generated from a plurality of scans of an analog signal, said method comprising:
  (n) programming a first sequence for utilizing summation and storage devices comprising an averaging device for averaging said digital signal data;
  (O) detecting of a particular feature of a repetitive analog signal;
  (p) generating a trigger signal in response to said detection;
  (q) generating timing pulses substantially synchronous with said trigger signal for each of said scans;
  (r) converting said analog signal to digital signal data with an analog-to-digital converter, in response to each of at least a subset of said timing pulses;
  (s) summing each of said digital signal data with the sum of digital signal data, acquired from any previous scans, that corresponds to the same phase of said analog signal, according to said first sequence; and
  (t) repeating steps (a) through (f) wherein said first sequence may be changed to a different sequence for each of said scans.

* * * * *